United States Patent
Lee et al.

(10) Patent No.: US 11,476,426 B2
(45) Date of Patent: Oct. 18, 2022

(54) ORGANIC LIGHT EMITTING COMPOUNDS AND ORGANIC LIGHT EMITTING DEVICES INCLUDING THE SAME

(71) Applicant: SFC CO., LTD., Cheongju-si (KR)

(72) Inventors: Se-jin Lee, Daejeon (KR); Taejung Yu, Yongin-si (KR); Seok-bae Park, Chungcheongnam-do (KR); Byung-sun Yang, Namwon-si (KR); Su-Jin Lee, Busan (KR); Bong-Hyang Lee, Busan (KR); Yeongtae Choi, Yongin-si (KR)

(73) Assignee: SFC CO., LTD., Cheongju-si (KR)

( * ) Notice: Subject to any disclaimer, the term of this patent is extended or adjusted under 35 U.S.C. 154(b) by 286 days.

(21) Appl. No.: 15/416,693

(22) Filed: Jan. 26, 2017

(65) Prior Publication Data
US 2017/0222160 A1    Aug. 3, 2017

(30) Foreign Application Priority Data

Feb. 3, 2016 (KR) ......................... 10-2016-0013509
Dec. 27, 2016 (KR) ......................... 10-2016-0180084

(51) Int. Cl.
*H01L 51/54* (2006.01)
*H01L 51/00* (2006.01)
*H05B 33/20* (2006.01)
*C07D 209/86* (2006.01)
*C07D 251/24* (2006.01)
(Continued)

(52) U.S. Cl.
CPC ........ *H01L 51/0072* (2013.01); *C07D 209/86* (2013.01); *C07D 251/24* (2013.01); *C07D 405/10* (2013.01); *C09K 11/025* (2013.01); *C09K 11/06* (2013.01); *H01L 51/0054* (2013.01); *H01L 51/0067* (2013.01); *H01L 51/0073* (2013.01); *H05B 33/20* (2013.01); *C09K 2211/1007* (2013.01); *C09K 2211/1029* (2013.01); *C09K 2211/185* (2013.01); *H01L 51/0052* (2013.01); *H01L 51/0085* (2013.01); *H01L 51/504* (2013.01); *H01L 51/5016* (2013.01); *H01L 51/5056* (2013.01); *H01L 51/5072* (2013.01); *H01L 51/5088* (2013.01); *H01L 51/5096* (2013.01); *H01L 2251/5384* (2013.01)

(58) Field of Classification Search
CPC ...... H05B 33/20; C09K 11/025; C09K 11/06; C09K 2211/00; C09K 2211/10; C09K 2211/1007; C09K 2211/1011; C09K 2211/1029; C09K 2211/185; C07D 209/86; C07D 405/00; C07D 405/10; C07D 251/24; H01L 51/0032; H01L 51/005; H01L 51/0052; H01L 51/0054; H01L 51/0067; H01L 51/0072; H01L 51/0073; H01L 51/0071; H01L 51/50; H01L 51/5012; H01L 51/5016; H01L 51/0085; H01L 51/5056; H01L 51/5072; H01L 51/5088; H01L 51/5096; H01L 51/504; H01L 2251/5384
USPC ....... 428/690, 691, 917, 411.4, 336; 427/58, 427/66; 313/500–512; 257/40, 88–104, 257/51.001, 51.052; 252/301.16–301.35
See application file for complete search history.

(56) References Cited

U.S. PATENT DOCUMENTS

2010/0001636 A1* 1/2010 Yabunouchi ........ H01L 51/0061
                                                    313/504
2012/0068170 A1* 3/2012 Pflumm ............... C07D 413/04
                                                    257/40
(Continued)

FOREIGN PATENT DOCUMENTS

KR    20120029751 A  *  3/2012
KR    20120078301 A  *  7/2012
(Continued)

OTHER PUBLICATIONS

Machine translation of KR2012-0029751. (Year: 2012).*
(Continued)

*Primary Examiner* — Andrew K Bohaty
(74) *Attorney, Agent, or Firm* — NSIP Law

(57) ABSTRACT

Disclosed is an organic light emitting device including a first electrode, a second electrode opposite to the first electrode, and at least one organic layer interposed between the first and second electrodes. The organic layer includes first and second compounds represented by Formulae A and B, respectively:

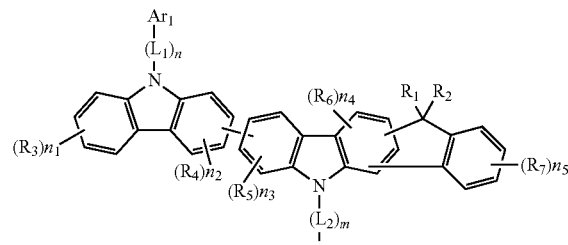

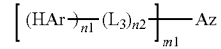

The organic light emitting device exhibits low driving voltage, high efficiency, and long life. Due to these advantages, the organic light emitting device is useful in a variety of industrial applications, including displays and lighting systems.

15 Claims, No Drawings

(51) Int. Cl.
*C07D 405/10* (2006.01)
*C09K 11/02* (2006.01)
*C09K 11/06* (2006.01)
*H01L 51/50* (2006.01)

(56) References Cited

U.S. PATENT DOCUMENTS

| | | | |
|---|---|---|---|
| 2014/0225046 A1* | 8/2014 | Jatsch | C07D 405/14 |
| | | | 252/519.3 |
| 2014/0231769 A1* | 8/2014 | Nishimura | H01L 51/0073 |
| | | | 257/40 |
| 2016/0126472 A1* | 5/2016 | Oh | C07D 405/04 |
| | | | 257/40 |
| 2017/0222157 A1 | 8/2017 | Jatsch et al. | |

FOREIGN PATENT DOCUMENTS

| | | | |
|---|---|---|---|
| KR | 10-2013-0112342 A | | 10/2013 |
| KR | 20140141951 A | * | 12/2014 |
| KR | 10-2015-0045809 A | | 4/2015 |
| KR | 10-2016-0011036 A | | 1/2016 |
| KR | 10-2016-0056298 A | | 5/2016 |
| KR | 10-2018-0031766 A | | 3/2018 |
| WO | WO 2014/204464 A1 | | 12/2014 |
| WO | WO-2015034125 A1 | * | 3/2015 ........... C07D 409/04 |
| WO | WO 2015/053575 A1 | | 4/2015 |
| WO | WO 2015/156587 A1 | | 10/2015 |
| WO | WO 2015/165563 A1 | | 11/2015 |
| WO | WO 2015/170882 A1 | | 11/2015 |
| WO | WO 2016/012075 A1 | | 1/2016 |

OTHER PUBLICATIONS

Machine translation of KR2014-0141951. (Year: 2014).*
Chinese Office Action dated Nov. 26, 2018 in corresponding Chinese Patent Application No. 201710063394.9 (10 pages in English, 6 pages in Chinese).
Chinese Office Action dated Nov. 26, 2018 in counterpart Chinese Patent Application No. 201710063394.9 (10 pages in English and 6 pages in Chinese).
Korean Office Action dated Mar. 10, 2021 in counterpart Korean Patent Application No. 10-2016-0180084 (16 pages in Korean).

* cited by examiner

ORGANIC LIGHT EMITTING COMPOUNDS AND ORGANIC LIGHT EMITTING DEVICES INCLUDING THE SAME

CROSS-REFERENCE TO RELATED APPLICATIONS

This application claims priority from Korean Patent Application No. 10-2016-0013509, filed on Feb. 3, 2016, and Korean Patent Application No. 10-2016-0180084, filed on Dec. 27, 2016, each of which is incorporated by reference herein in its entirety.

BACKGROUND OF THE INVENTION

1. Field of the Invention

The present invention relates to organic light emitting devices with low driving voltage, high efficiency, and long life.

2. Description of the Related Art

Organic light emitting diodes are self-luminous devices and have the advantages of large viewing angle, high contrast, short response time, high luminance, low driving voltage, and excellent response speed characteristics. Another advantage of organic light emitting diodes is their ability to produce multiple colors.

The most important factor determining the luminescent properties (e.g., luminous efficiency) of an organic light emitting diode is a light emitting material. When a light emitting layer of an organic light emitting device uses a single light emitting material, intermolecular interaction or luminescence quenching occurs. The intermolecular interaction shifts the maximum emission to a longer wavelength and causes low color purity. The luminescence quenching leads to poor device efficiency. In an attempt to solve these problems, a host/dopant system was proposed. The two light emitting materials are co-deposited to form a light emitting layer with high color purity. In addition, the light emitting layer exhibits high luminous efficiency through energy transfer. If needed, two or more materials may be co-deposited to form a light emitting layer.

Fluorescent materials are widely used at present as materials for light emitting layers but extensive research is being conducted to develop phosphorescent materials, which are known to achieve improved luminous efficiency theoretically by a factor of up to 4 compared to fluorescent materials, based on the luminescence mechanism of organic light emitting layers.

For phosphorescent materials with high efficiency, however, stable host and dopant compounds are difficult to synthesize. Further, the application of phosphorescent materials to light emitting layers causes many problems associated with instability resulting from high energy barriers at the interfaces with the light emitting layers. Particularly, phosphorescent materials have high current efficiency but their high driving voltage leads to low power efficiency and considerably short device life. Phosphorescent materials cause. Under these circumstances, there is an urgent need to find a solution to the problems of phosphorescent materials.

SUMMARY OF THE INVENTION

Therefore, the present invention has been made in an effort to solve the above problems and is directed to providing organic light emitting compounds that ensure high efficiency, low driving voltage, and improved life characteristics of organic light emitting devices. The present invention is also directed to providing organic light emitting devices including the organic light emitting compounds.

The present invention provides an organic light emitting device including a first electrode, a second electrode opposite to the first electrode, and at least one organic layer interposed between the first and second electrodes wherein the organic layer includes first and second compounds represented by Formulae A and B, respectively:

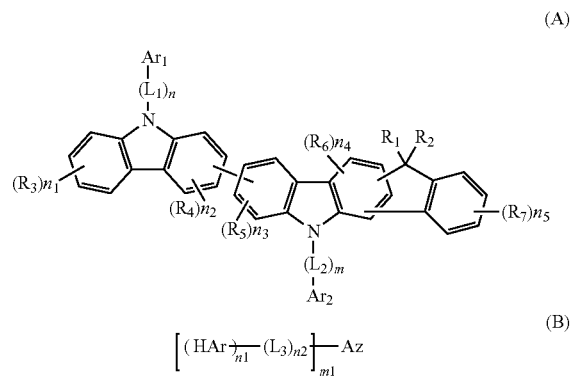

(A)

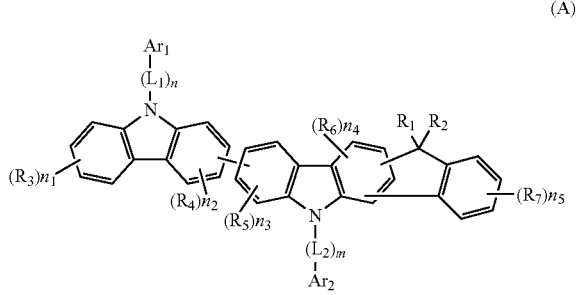

(B)

Specific structures of the first compound represented by Formula A and the second compound represented by Formula B are described below.

The organic light emitting device of the present invention exhibits low driving voltage, high efficiency, and long life. Due to these advantages, the organic light emitting device of the present invention is useful in a variety of industrial applications, including displays and lighting systems.

DETAILED DESCRIPTION OF THE INVENTION

The present invention will now be described in more detail.

An organic light emitting device of the present invention includes a first electrode, a second electrode opposite to the first electrode, and at least one organic layer (preferably a light emitting layer) interposed between the first and second electrodes wherein the organic layer includes a first compound represented by Formula A:

(A)

wherein $L_1$ and $L_2$ are identical to or different from each other and are each independently a single bond or a linker selected from substituted or unsubstituted $C_1$-$C_{60}$ alkylene groups, substituted or unsubstituted $C_2$-$C_{60}$ alkenylene groups, substituted or unsubstituted $C_2$-$C_{60}$ alkynylene groups, substituted or unsubstituted $C_3$-$C_{60}$ cycloalkylene groups, substituted or unsubstituted $C_2$-$C_{60}$ heterocycloalkylene groups, substituted or unsubstituted $C_6$-$C_{60}$ arylene groups, and substituted or unsubstituted $C_2$-$C_{60}$ heteroarylene groups, n and m are each independently an integer from 0 to 3, $Ar_1$ and $Ar_2$ and $R_1$ to $R_7$ are identical to or different from each other and are each independently selected from hydrogen, deuterium, substituted or unsubstituted $C_1$-$C_{30}$ alkyl groups, substituted or unsubstituted $C_2$-$C_{30}$ alkenyl groups, substituted or unsubstituted $C_3$-$C_{30}$ cycloalkyl groups, substituted or unsubstituted $C_5$-$C_{30}$ cycloalkenyl groups, substituted or unsubstituted $C_1$-$C_{30}$ alkoxy groups, substituted or unsubstituted $C_6$-$C_{30}$ aryloxy groups, substituted or unsubstituted $C_1$-$C_{30}$ alkylthioxy groups, substituted or unsubstituted $C_5$-$C_{30}$ arylthioxy groups, substituted or unsubstituted $C_1$-$C_{30}$ alkylamine groups, substituted or unsubstituted $C_5$-$C_{30}$ arylamine groups, substituted or unsubstituted $C_6$-$C_{50}$ aryl groups, substituted or unsubstituted $C_3$-$C_{50}$ heteroaryl groups containing O, N or S as a heteroatom, substituted or unsubstituted silyl groups, substituted or unsubstituted germanium groups, substituted or unsubstituted boron groups, substituted or unsubstituted aluminum groups, a carbonyl group, a phosphoryl group, an amino group, a nitrile group, a hydroxyl group, a nitro group, halogen groups, a selenium group, a tellurium group, an amide group, and an ester group, with the proviso that each of $Ar_1$ and $Ar_2$ and $R_1$ to $R_7$ optionally forms an aliphatic, aromatic, heteroaliphatic or heteroaromatic fused ring with the adjacent group, and n1 to n5 are each independently an integer from 0 to 4, and a second compound represented by Formula B:

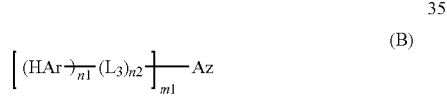

(B)

wherein HAr is selected from substituted or unsubstituted $C_6$-$C_{30}$ aryl groups and substituted or unsubstituted $C_5$-$C_{30}$ heterocyclic groups, $L_3$ is a single bond or a linker selected from substituted or unsubstituted $C_1$-$C_{60}$ alkylene groups, substituted or unsubstituted $C_2$-$C_{60}$ alkenylene groups, substituted or unsubstituted $C_2$-$C_{60}$ alkynylene groups, substituted or unsubstituted $C_3$-$C_{60}$ cycloalkylene groups, substituted or unsubstituted $C_2$-$C_{60}$ heterocycloalkylene groups, substituted or unsubstituted $C_6$-$C_{60}$ arylene groups, and substituted or unsubstituted $C_2$-$C_{60}$ heteroarylene groups, n1 and m1 are each independently an integer from 1 to 3, n2 is an integer from 0 to 3, and Az is a nitrogen-containing ring represented by Formula C:

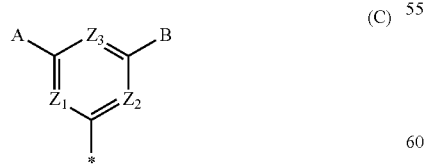

(C)

wherein $Z_1$ to $Z_3$ are identical to or different from each other and are each independently N or CR, with the proviso that at least one of $Z_1$ to $Z_3$ is N, A, B, and R are each independently selected from hydrogen, deuterium, substituted or unsubstituted $C_1$-$C_{30}$ alkyl groups, substituted or unsubstituted $C_2$-$C_{30}$ alkenyl groups, substituted or unsubstituted $C_3$-$C_{30}$ cycloalkyl groups, substituted or unsubstituted $C_5$-$C_{30}$ cycloalkenyl groups, substituted or unsubstituted $C_1$-$C_{30}$ alkoxy groups, substituted or unsubstituted $C_6$-$C_{30}$ aryloxy groups, substituted or unsubstituted $C_1$-$C_{30}$ alkylthioxy groups, substituted or unsubstituted $C_5$-$C_{30}$ arylthioxy groups, substituted or unsubstituted $C_1$-$C_{30}$ alkyl amine groups, substituted or unsubstituted $C_5$-$C_{30}$ aryl amine groups, substituted or unsubstituted $C_6$-$C_{50}$ aryl groups, substituted or unsubstituted $C_3$-$C_{50}$ heteroaryl groups containing O, N or S as a heteroatom, substituted or unsubstituted silyl groups, substituted or unsubstituted germanium groups, substituted or unsubstituted boron groups, substituted or unsubstituted aluminum groups, a carbonyl group, a phosphoryl group, an amino group, a nitrile group, a hydroxyl group, a nitro group, halogen groups, a selenium group, a tellurium group, an amide group, and an ester group, with the proviso that each of A, B, and R optionally forms an aliphatic, aromatic, heteroaliphatic or heteroaromatic fused ring with the adjacent group.

According to one embodiment of the present invention, HAr in Formula B may be selected from the following structures:

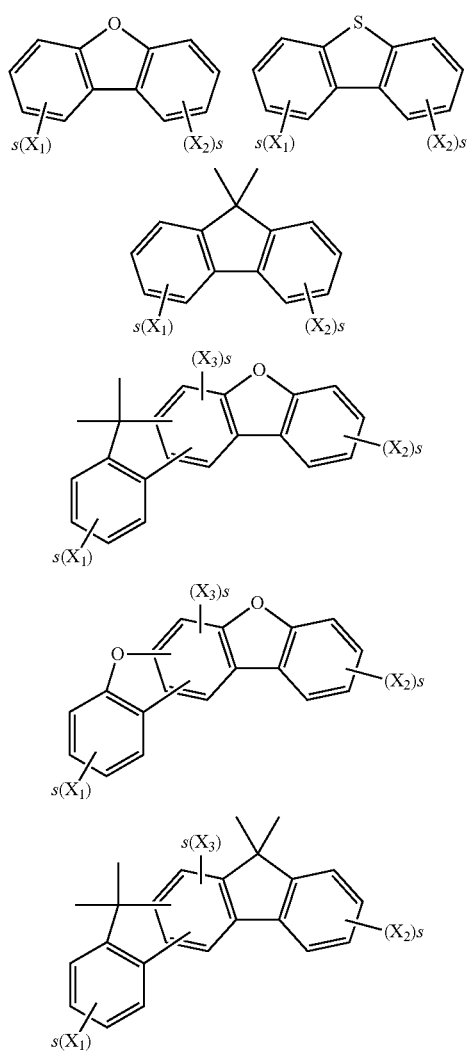

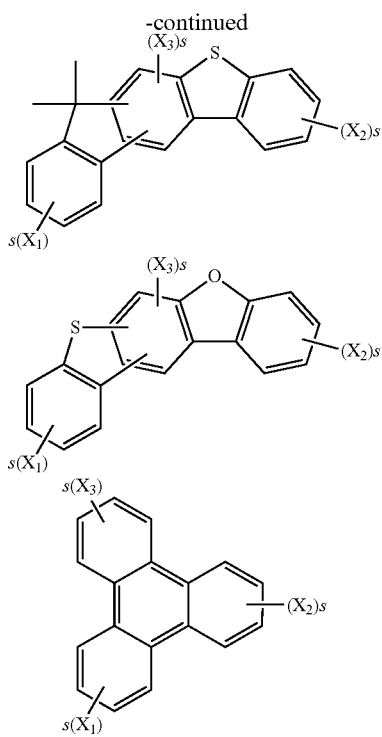

wherein $X_1$ to $X_3$ are identical to or different from each other and are each independently selected from hydrogen, deuterium, substituted or unsubstituted $C_1$-$C_{30}$ alkyl groups, substituted or unsubstituted $C_2$-$C_{30}$ alkenyl groups, substituted or unsubstituted $C_3$-$C_{30}$ cycloalkyl groups, substituted or unsubstituted $C_5$-$C_{30}$ cycloalkenyl groups, substituted or unsubstituted $C_1$-$C_{30}$ alkoxy groups, substituted or unsubstituted $C_6$-$C_{30}$ aryloxy groups, substituted or unsubstituted $C_1$-$C_{30}$ alkylthioxy groups, substituted or unsubstituted $C_5$-$C_{30}$ arylthioxy groups, substituted or unsubstituted $C_1$-$C_{30}$ alkyl amine groups, substituted or unsubstituted $C_5$-$C_{30}$ aryl amine groups, substituted or unsubstituted $C_5$-$C_{50}$ aryl groups, substituted or unsubstituted $C_3$-$C_{50}$ heteroaryl groups containing O, N or S as a heteroatom, substituted or unsubstituted silyl groups, substituted or unsubstituted germanium groups, substituted or unsubstituted boron groups, substituted or unsubstituted aluminum groups, a carbonyl group, a phosphoryl group, an amino group, a nitrile group, a hydroxyl group, a nitro group, halogen groups, a selenium group, a tellurium group, an amide group, and an ester group, with the proviso that each of $X_1$ to $X_3$ optionally forms an aliphatic, aromatic, heteroaliphatic or heteroaromatic fused ring with the adjacent group and one of $X_1$ to $X_3$ is linked to $L_3$ in Formula B, and s is an integer from 1 to 4.

Each of $L_1$, $L_2$, $L_3$, $Ar_1$, $Ar_2$, HAr, A, B, $R_1$ to $R_7$, and $X_1$ to $X_3$ may be further substituted with one or more substituents selected from $C_1$-$C_{60}$ alkyl groups, $C_5$-$C_{60}$ heteroaryl groups, $C_3$-$C_{60}$ cycloalkyl groups, $C_6$-$C_{60}$ aryl groups, $C_1$-$C_{60}$ alkoxy groups, $C_6$-$C_{30}$ aryloxy groups, $C_1$-$C_{20}$ alkylamino groups, $C_1$-$C_{20}$ alkylsilyl groups, $C_6$-$C_{30}$ arylsilyl groups, $C_1$-$C_{50}$ arylalkylamino groups, $C_2$-$C_{60}$ alkenyl groups, a cyano group, halogen groups, and deuterium.

In the "substituted or unsubstituted $C_1$-$C_{30}$ alkyl groups", "substituted or unsubstituted $C_6$-$C_{50}$ aryl groups", etc., the number of carbon atoms in each alkyl or aryl group is considered as the number of carbon atoms constituting the unsubstituted alkyl or aryl moiety and the number of carbon atoms in the substituent(s) is excluded therefrom.

Specific examples of the alkyl groups used in the present invention include methyl, ethyl, propyl, isobutyl, sec-butyl, tert-butyl, pentyl, iso-amyl, hexyl, heptyl, octyl, stearyl, trichloromethyl, and trifluoromethyl groups. At least one hydrogen atom of each alkyl group may be substituted with a deuterium atom, a halogen atom, a hydroxyl group, a nitro group, a cyano group, a trifluoromethyl group, a silyl group (herein referred to as an "alkylsilyl group"), a substituted or unsubstituted amino group (—$NH_2$, —NH(R) or —N(R')(R"), in which R, R', and R" are each independently a $C_1$-$C_{24}$ alkyl group (the —NH(R) and —N(R')(R") are referred to as "alkylamino groups"), an amidino group, a hydrazine group, a hydrazone group, a carboxyl group, a sulfonic acid group, a phosphoric acid group, a $C_1$-$C_{24}$ alkyl group, a $C_1$-$C_{24}$ halogenated alkyl group, a $C_2$-$C_{24}$ alkenyl group, a $C_2$-$C_{24}$ alkynyl group, a $C_1$-$C_{24}$ heteroalkyl group, a $C_5$-$C_{24}$ aryl group, a $C_6$-$C_{24}$ arylalkyl group, a $C_3$-$C_{24}$ heteroaryl group or a $C_3$-$C_{24}$ heteroarylalkyl group.

Specific examples of the alkoxy groups used in the present invention include methoxy, ethoxy, propoxy, isobutyloxy, sec-butyloxy, pentyloxy, iso-amyloxy, and hexyloxy groups. The alkoxy groups may be substituted with the same substituents as in the alkyl groups.

Specific examples of the halogen groups used in the present invention include fluoro (F), chloro (Cl), and bromo (Br) groups.

The aryloxy groups used in the present invention refer to —O-aryl radicals in which the aryl group is as defined above. Specific examples of the aryloxy groups include phenoxy, naphthoxy, anthracenyloxy, phenanthrenyloxy, fluorenyloxy, and indenyloxy. At least one hydrogen atom of each aryloxy group may be substituted.

Specific examples of the silyl groups used in the present invention include trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl.

The aryl groups used in the present invention are organic radicals derived from aromatic hydrocarbons by removal of a hydrogen atom. Such aryl groups include 5- to 7-membered, preferably 5- or 6-membered single or fused ring systems. When the aryl group is substituted, the substituent may be fused with an adjacent substituent to form a ring.

Specific examples of the aryl groups include aromatic groups, such as phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, crycenyl, naphthacenyl, and fluoranthenyl groups.

Each aryl group may also be substituted with at least one substituent. More specifically, at least one hydrogen atom of each aryl group may be substituted with a deuterium atom, a halogen atom, a hydroxyl group, a nitro group, a cyano group, a silyl group, an amino group (—$NH_2$, —NH(R), —N(R')(R") in which R, R' and R" are each independently a $C_1$-$C_{10}$ alkyl group (the —NH(R) and —N(R')(R") are referred to as "alkylamino groups")), an amidino group, a hydrazine group, a hydrazone group, a carboxyl group, a sulfonic acid group, a phosphoric acid group, a $C_1$-$C_{24}$ alkyl group, a $C_1$-$C_{24}$ halogenated alkyl group, a $C_1$-$C_{24}$ alkenyl group, a $C_1$-$C_{24}$ alkynyl group, a $C_1$-$C_{24}$ heteroalkyl group, a $C_6$-$C_{24}$ aryl group, a $C_6$-$C_{24}$ arylalkyl group, a $C_2$-$C_{24}$ heteroaryl group or a $C_2$-$C_{24}$ heteroarylalkyl group.

The heteroaryl groups used in the present invention may be selected from the following structures:

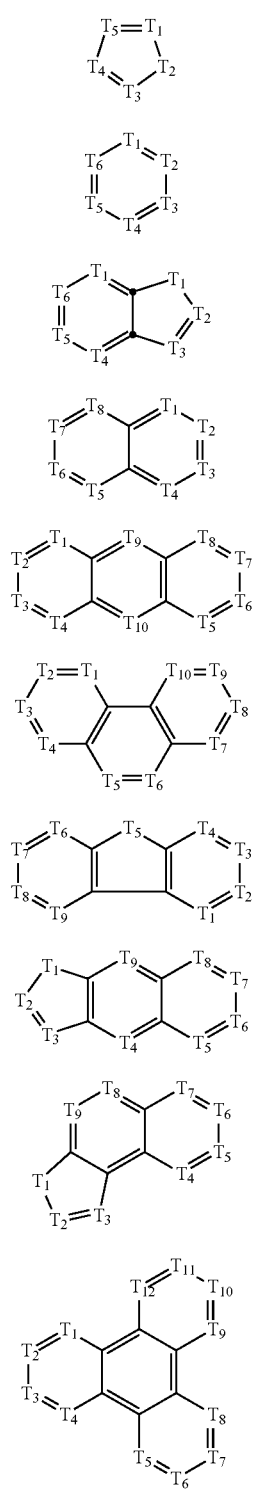

Structure 1
Structure 2
Structure 3
Structure 4
Structure 5
Structure 6
Structure 7
Structure 8
Structure 9
Structure 10 wherein $T_1$ to $T_{12}$ are identical to or different from each other and are each independently selected from $C(R_{101})$, $C(R_{102})(R_{103})$, N, $N(R_{104})$, O, and S, with the proviso that $T_1$ to $T_{12}$ are not simultaneously carbon atoms, $R_{101}$ to $R_{104}$ are identical to or different from each other and are each independently selected from hydrogen, deuterium, substituted or unsubstituted $C_1$-$C_{30}$ alkyl groups, substituted or unsubstituted $C_3$-$C_{30}$ cycloalkyl groups, substituted or unsubstituted $C_5$-$C_{30}$ aryl groups, and substituted or unsubstituted $C_2$-$C_{30}$ heteroaryl groups containing O, N, S or P as a heteroatom.

Due to resonance resulting from the migration of electrons, Structure 3 may also be represented by the following structure 3-1:

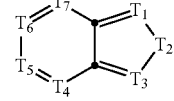

Structure 3-1 wherein $T_1$ to $T_7$ are as defined in Structures 1 to 10.

According to a preferred embodiment of the present invention, Structures 1 to 10 may be selected from the following structures:

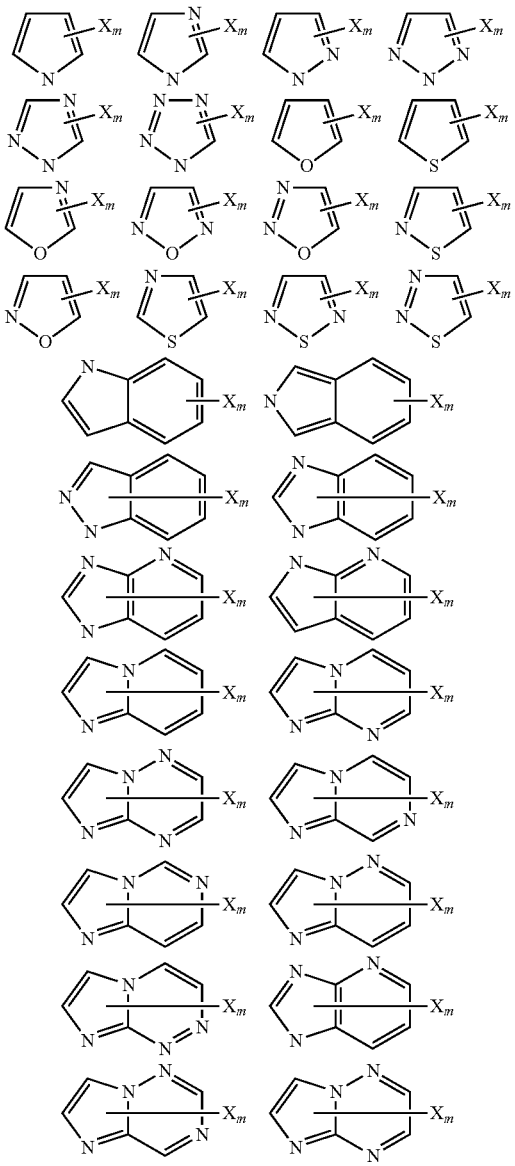

-continued
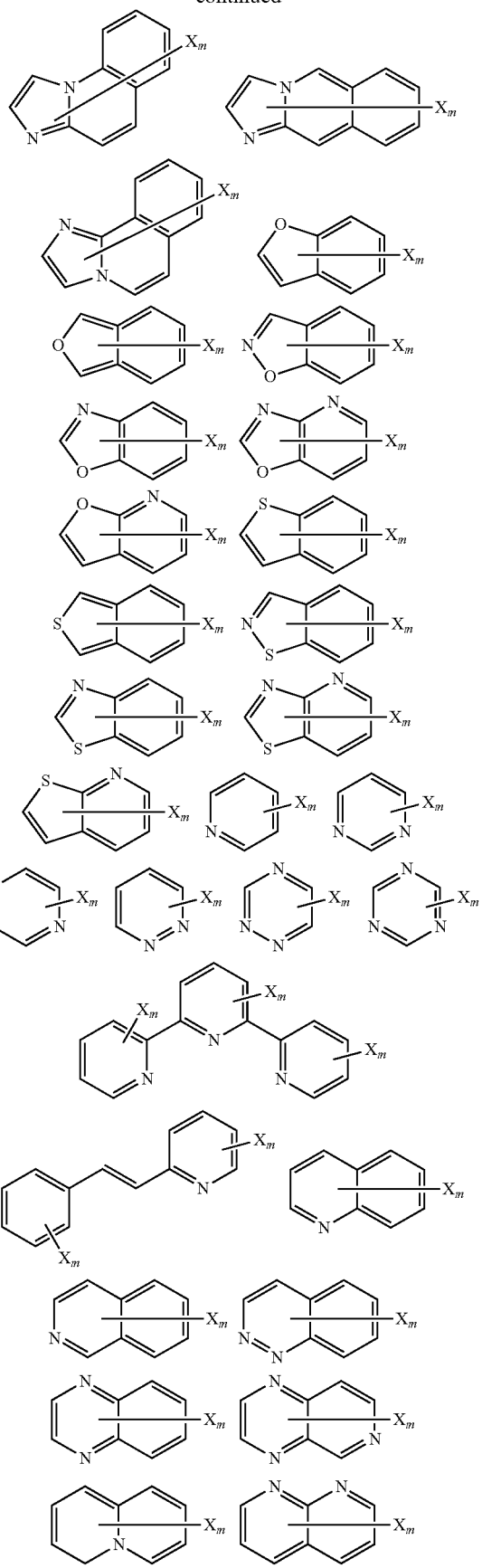
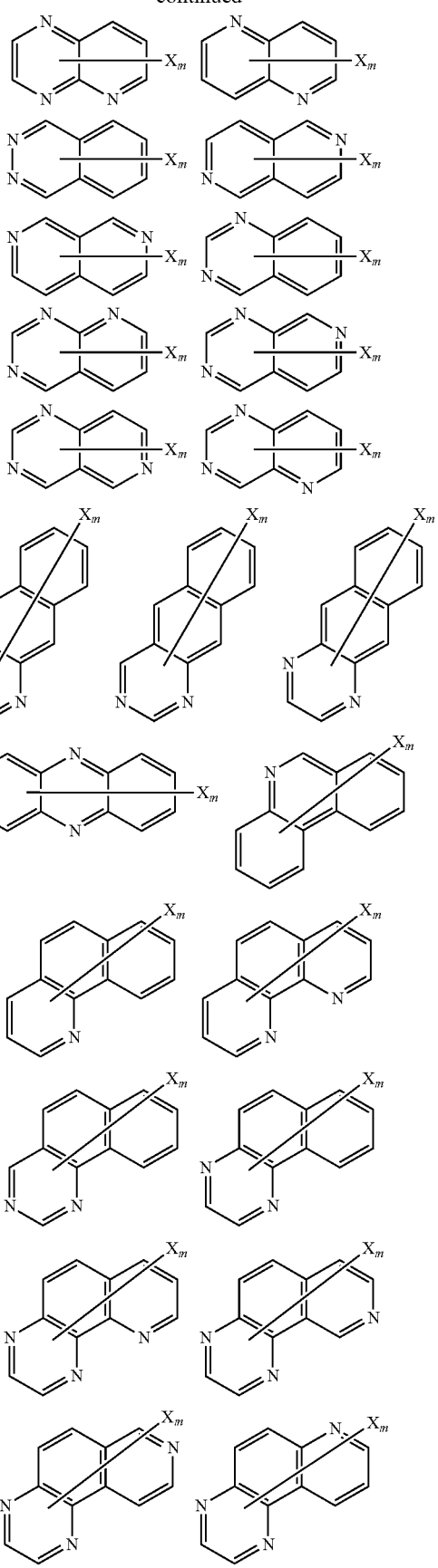

-continued

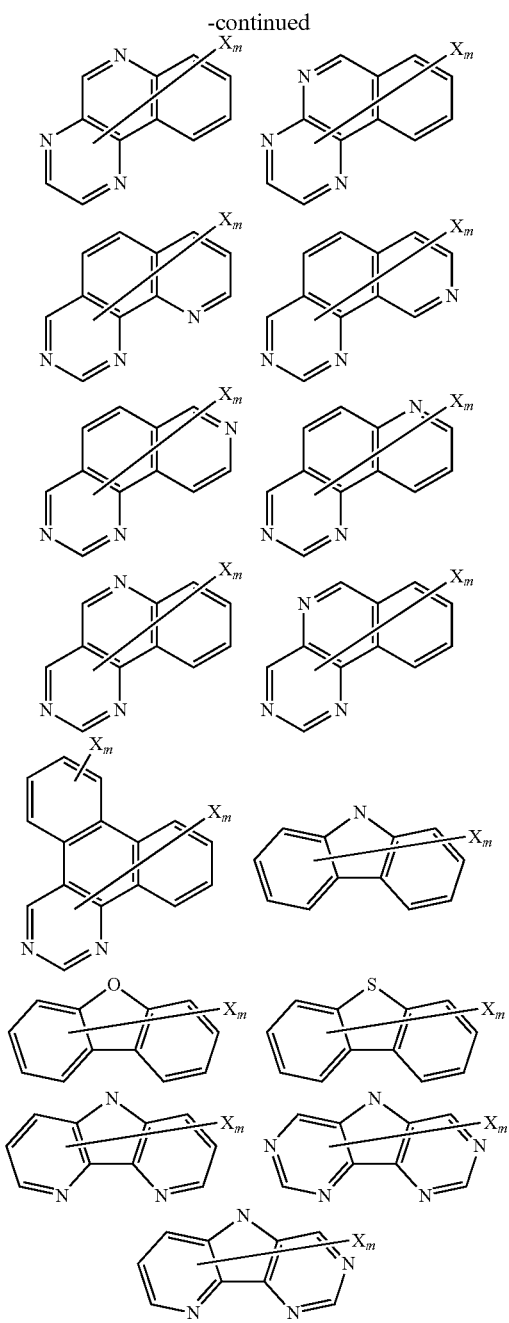

wherein X has the same meaning as $X_1$ to $X_8$ defined above, m is an integer from 1 to 11, provided that when m is equal to or greater than 2, the plurality of X groups are identical to or different from each other.

The first compound represented by Formula A may be selected from Compounds H1 to H60, which are specifically described in the Examples section and claims that follow, but the scope of Formula A is not limited thereto.

The second compound represented by Formula B may be selected from Compounds E1 to E132, which are specifically described in the Examples section and claims that follow, but the scope of Formula B is not limited thereto.

As described above, the organic light emitting device of the present invention includes a first electrode, a second electrode opposite to the first electrode, and at least one organic layer interposed between the first and second electrodes. The organic layer includes a light emitting layer, a hole transport layer between the light emitting layer and the first electrode, and an electron transport layer between the light emitting layer and the second electrode.

The light emitting layer includes the first compound represented by Formula A and the second compound represented by Formula B. According to one embodiment of the present invention, the light emitting layer may further include a dopant compound.

According to one embodiment of the present invention, the first compound, the second compound, and the dopant compound may be mixed in a weight ratio of 1:0.01-99:0.01-15. Within this range, satisfactory energy transfer and emission may occur.

A more detailed description will be given concerning the organic light emitting device of the present invention.

The organic light emitting device of the present invention includes an anode, a hole transport layer, a light emitting layer, an electron transport layer, and a cathode. The organic light emitting device of the present invention may optionally further include a hole injecting layer and an electron injecting layer. One or more intermediate layers may be further formed in the organic light emitting device. A hole blocking layer or an electron blocking layer may be further formed in the organic light emitting device. The device may further include one or more organic layers with various functions depending on the desired characteristics thereof.

A description will be given concerning a method for fabricating the organic light emitting device of the present invention. First, an electrode material for the anode is coated on a substrate to form the anode. The substrate may be any of those used in general organic light emitting devices. The substrate is preferably an organic substrate or a transparent plastic substrate that is excellent in transparency, surface smoothness, ease of handling, and waterproofness. A highly transparent and conductive metal oxide, such as indium tin oxide (ITO), indium zinc oxide (IZO), tin oxide ($SnO_2$) or zinc oxide (ZnO), is used as the anode material.

A material for the hole injecting layer is coated on the anode by vacuum thermal evaporation or spin coating to form the hole injecting layer. Then, a material for the hole transport layer is coated on the hole injecting layer by vacuum thermal evaporation or spin coating to form the hole transport layer.

The material for the hole injecting layer is not specially limited so long as it is usually used in the art. Example of such materials include 4,4',4"-tris(2-naphthyl(phenyl)amino)triphenylamine (2-TNATA), N,N'-di(1-naphthyl)-N,N'-diphenylbenzidine) (NPD), N,N'-diphenyl-N,N'-bis(3-methylphenyl)-1,1'-biphenyl-4,4'-diamine (TPD), and N,N'-diphenyl-N,N'-bis[4-(phenyl-m-tolylamino)phenyl]biphenyl-4,4'-diamine (DNTPD).

The material for the hole transport layer is not specially limited so long as it is commonly used in the art. Example of such materials include N,N'-bis(3-methylphenyl)-N,N'-diphenyl-[1,1-biphenyl]-4,4'-diamine (TPD) and N,N'-di(naphthalen-1-yl)-N,N'-diphenylbenzidine (α-NPD).

Subsequently, the organic light emitting layer is laminated on the hole transport layer. A hole blocking layer may be optionally formed on the organic light emitting layer by vacuum thermal evaporation or spin coating. The hole blocking layer blocks holes from entering the cathode through the organic light emitting layer. This role of the hole blocking layer prevents the life and efficiency of the device from deteriorating. A material having a very low highest occupied molecular orbital (HOMO) energy level is used for the hole blocking layer. The hole blocking material is not particularly limited so long as it has the ability to transport electrons and a higher ionization potential than the light emitting compound. Representative examples of suitable hole blocking materials include BAlq, BCP, and TPBI.

The electron transport layer is deposited on the hole blocking layer by vacuum thermal evaporation or spin coating, and the electron injecting layer is formed thereon.

A metal for the cathode is deposited on the electron injecting layer by vacuum thermal evaporation to form the cathode, completing the fabrication of the organic light emitting device. As the metal for the cathode, there may be used, for example, lithium (Li), magnesium (Mg), aluminum (Al), aluminum-lithium (Al—Li), calcium (Ca), magnesium-indium (Mg—In) or magnesium-silver (Mg—Ag). The organic light emitting device may be of top emission type. In this case, a transmissive material, such as ITO or IZO, may be used for the cathode.

The material for the electron transport layer functions to stably transport electrons injected from the electron injecting electrode (i.e. the cathode). The material for the electron transport layer may be any known electron transport material, and examples thereof include, but are not limited to, quinoline derivatives, particularly, tris(8-quinolinolate)aluminum (Alq3), TAZ, Balq, beryllium bis(benzoquinolin-10-olate (Bebq2), ADN, and oxadiazole derivatives, such as PBD, BMD, and BND.

One or more layers selected from the hole injecting layer, the hole transport layer, the electron blocking layer, the light emitting layer, the hole blocking layer, the electron transport layer, and the electron injecting layer may be formed by a monomolecular deposition or solution process. According to the monomolecular deposition process, the material for each layer is evaporated under heat and vacuum or reduced pressure to form the layer in the form of a thin film. According to the solution process, the material for each layer is mixed with a suitable solvent, and then the mixture is formed into a thin film by a suitable method, such as ink-jet printing, roll-to-roll coating, screen printing, spray coating, dip coating or spin coating.

The organic light emitting devices of the present invention can be used in a variety of systems, such as flat panel displays, flexible displays, monochromatic flat panel lighting systems, white flat panel lighting systems, flexible monochromatic lighting systems, and flexible white lighting systems.

The present invention will be explained in more detail with reference to the following examples. However, these examples are provided to assist in understanding the invention and are not intended to limit the scope of the present invention.

Synthesis Example 1: Synthesis of Compound H1

Synthesis Example 1-(1): Synthesis of Intermediate 1-a

Intermediate 1-a was synthesized according to Reaction Scheme 1.

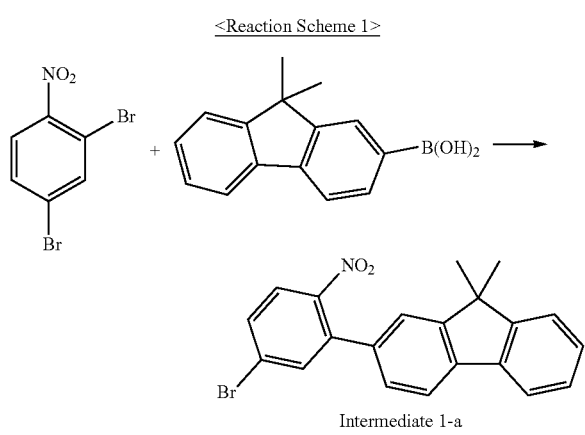

2,4-Dibromonitrobenzene (30.0 g, 107 mmol), (9,9-dimethyl-9H-fluoren-2-yl)boronic acid (30.5 g, 128 mmol), tetrakis(triphenylphosphine)palladium (2.5 g, 2 mmol), and potassium carbonate (29.5 g, 214 mmol) were placed in a 1 L round bottom flask, and 210 mL of toluene, 90 mL of ethanol, and 60 mL of water were added thereto. The mixture was heated to reflux with stirring overnight. After completion of the reaction, the reactor was cooled to room temperature. The reaction mixture was extracted with ethyl acetate. The organic layer was concentrated under reduced pressure and purified by column chromatography to give Intermediate 1-a (35.0 g, 69%).

Synthesis Example 1-(2): Synthesis of Intermediate 1-b

Intermediate 1-b was synthesized according to Reaction Scheme 2.

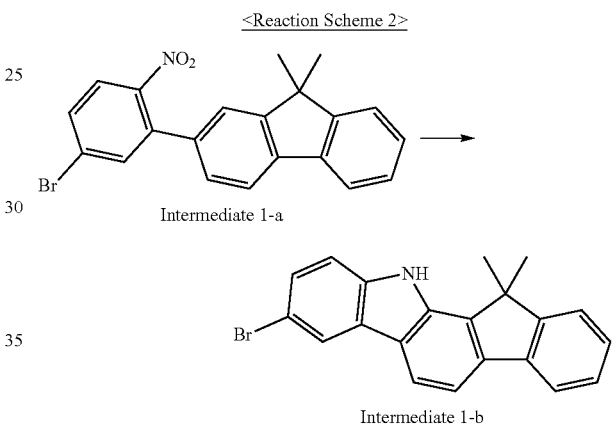

Intermediate 1-a (35.0 g, 89 mmol) and triphenylphosphine (69.9 g, 266 mmol) were placed in a 500 mL reactor and 1,2-dichlorobenzene (350 mL) was added thereto. The temperature of the reactor was raised to 120° C. The mixture was stirred at the same temperature overnight. After completion of the reaction, the reaction solution was concentrated by heating and purified by column chromatography to give Intermediate 1-b (9.4 g, 29%).

Synthesis Example 1-(3): Synthesis of Intermediate 1-c

Intermediate 1-c was synthesized according to Reaction Scheme 3.

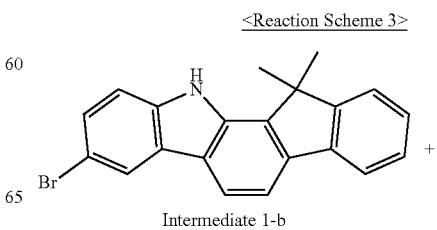

-continued

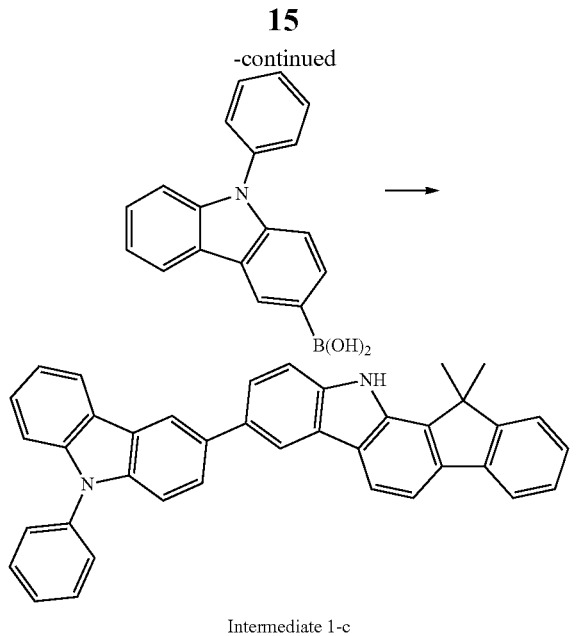

Intermediate 1-c

Intermediate 1-b (8.2 g, 23 mmol), N-phenylcarbazole-3-boronic acid (7.8 g, 27 mmol), tetrakis(triphenylphosphine) palladium (0.5 g, 1 mmol), and potassium carbonate (6.3 g, 45 mmol) were placed in a 250 mL round bottom flask and toluene (58 mL), ethanol (25 mL), and water (17 mL) were added thereto. The mixture was heated to reflux with stirring overnight. After completion of the reaction, the reactor was cooled to room temperature. The reaction mixture was extracted with ethyl acetate. The organic layer was concentrated under reduced pressure and purified by column chromatography to give Intermediate 1-c (8.8 g, 74%).

Synthesis Example 1-(4): Synthesis of Compound H1

Compound H1 was synthesized according to Reaction Scheme 4.

<Reaction Scheme 4>

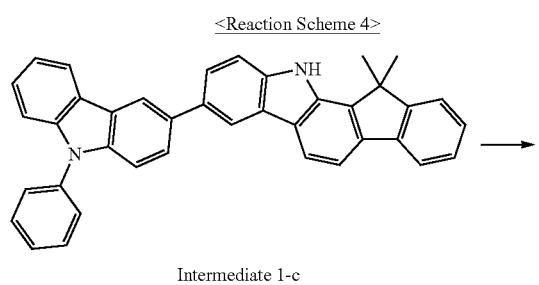

Intermediate 1-c

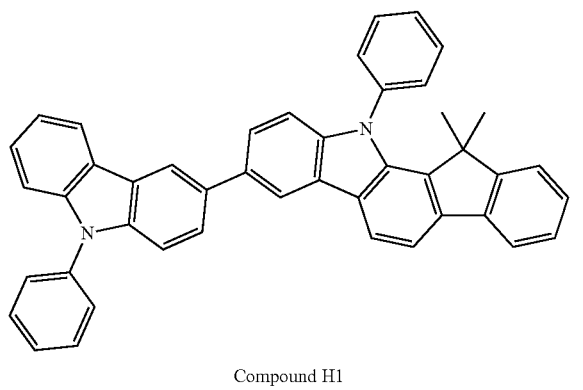

Compound H1

Intermediate 1-c (8.8 g, 16.8 mmol), bromobenzene (7.9 g, 50.3 mmol), bis(dibenzylideneacetone)palladium(0) (0.3 g, 0.5 mmol), tri-tert-butylphosphine tetrahydroborate (1.0 g, 3.4 mmol), sodium tert-butoxide (4.84 g, 50 mmol), and xylene (90 mL) were placed in a 250 mL round bottom flask. The mixture was heated to reflux with stirring overnight. The reaction solution was filtered, concentrated under reduced pressure, purified by column chromatography, and recrystallized from toluene and ethyl acetate to give Compound H1 (5.6 g, 55.6%).

MS (MALDI-TOF): m/z 600.26[M$^+$]

Synthesis Example 2: Synthesis of Compound H9

Synthesis Example 2-(1): Synthesis of Intermediate 2-a

Intermediate 2-a was synthesized according to Reaction Scheme 5.

<Reaction Scheme 5>

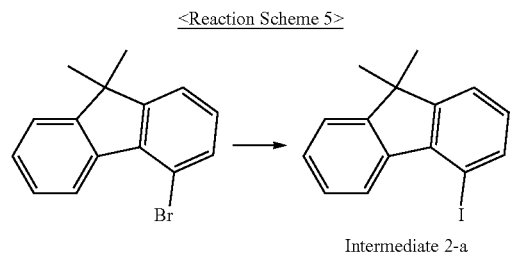 [SMILES: CC1(C)c2ccccc2-c2c(Br)cccc21 ; CC1(C)c2ccccc2-c2c(I)cccc21]

Intermediate 2-a

4-Bromo-9,9-dimethylfluorene (28.5 g, 0.104 mol) was dissolved in tetrahydrofuran (280 mL) in a 500 mL round bottom flask. The solution was cooled to −78° C. under a stream of nitrogen gas and n-butyllithium (1.6 M) (78.2 mL, 0.125 mol) was slowly added dropwise thereto. After stirring at the same temperature for 1 h, iodine (31.8 g, 0.125 mol) was added portionwise. After the iodine addition was completed, the resulting mixture was stirred at room temperature overnight. The reaction mixture was washed with an aqueous solution of sodium thiosulfate and extracted with ethyl acetate and water. The organic layer was concentrated under reduced pressure and purified by column chromatography to give Intermediate 2-a (30.3 g, 91%).

Synthesis Example 2-(2): Synthesis of Intermediate 2-b

Intermediate 2-b was synthesized according to Reaction Scheme 6.

<Reaction Scheme 6>

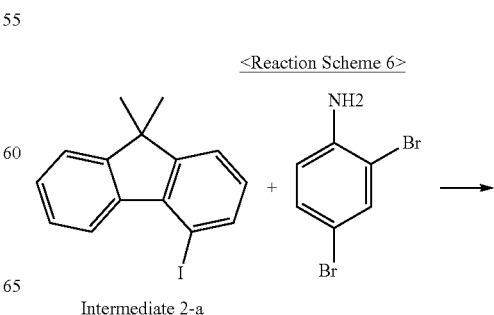

Intermediate 2-a

-continued

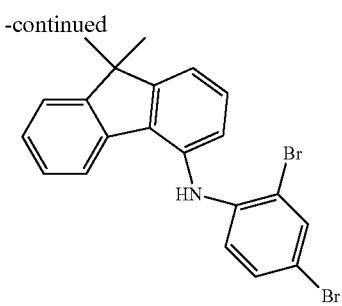

Intermediate 2-b

Intermediate 2-a (30.3 g, 0.095 mol), 2,4-dibromoaniline (28.5 g, 0.114 mol), bis(dibenzylideneacetone)palladium(0) (1.09 g, 2 mmol), 2,2'-bis(diphenylphosphino)-1,1'-binaphthalene (2.36 g, 4 mmol), sodium tert-butoxide (18.2 g, 0.189 mol), and toluene 300 mL were placed in a 500 mL round bottom flask. The mixture was refluxed with stirring overnight. After completion of the reaction, the reaction mixture was filtered, concentrated under reduced pressure, and purified by column chromatography to give Intermediate 2-b (32.5 g, 78%).

Synthesis Example 2-(3): Synthesis of Intermediate 2-c

Intermediate 2-c was synthesized according to Reaction Scheme 7.

<Reaction Scheme 7>

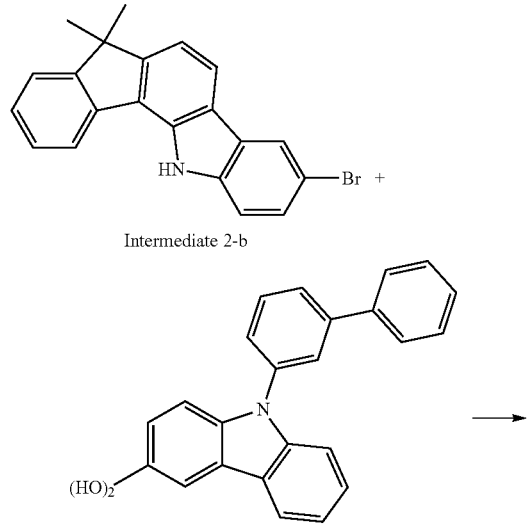

Intermediate 2-b (32.5 g, 0.073 mol), tricyclohexylphosphine tetrafluoroborate (0.5 g, 1 mmol), palladium(II) acetate (0.2 g, 1 mmol), potassium carbonate (20.3 g, 0.147 mol), and N,N-dimethylacetamide (320 mL) were placed in a 500 mL round bottom flask. The mixture was refluxed with stirring overnight. After completion of the reaction, the reaction solution was cooled to room temperature. The reaction solution was extracted with ethyl acetate, heptane, and water. The organic layer was concentrated under reduced pressure and purified by column chromatography to give Intermediate 2-c (15.4 g, 58.0%).

Synthesis Example 2-(4): Synthesis of Intermediate 2-d

Intermediate 2-d was synthesized according to Reaction Scheme 8.

<Reaction Scheme 8>

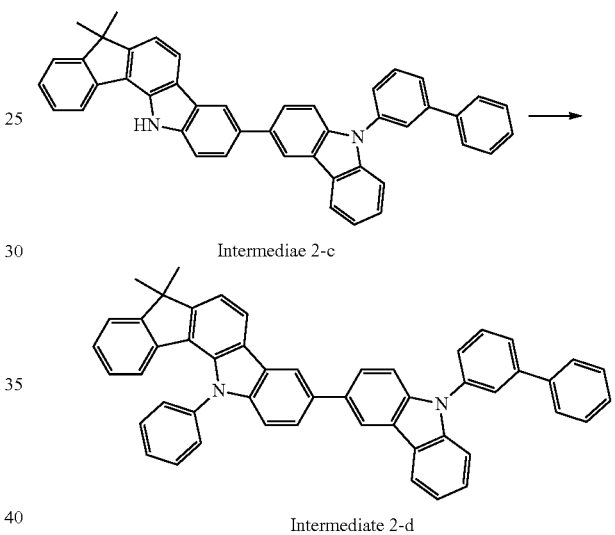

Intermediate 2-d (11.8 g, 46%) was synthesized in the same manner as in Synthesis Example 1-(3), except that Intermediate 2-c and 9-(biphenyl-3-yl)-9H-carbazol-3-ylboronic acid were used instead of Intermediate 1-b and N-phenylcarbazole-3-boronic acid, respectively.

Synthesis Example 2-(5): Synthesis of Compound H9

Compound H9 was synthesized according to Reaction Scheme 9.

<Reaction Scheme 9>

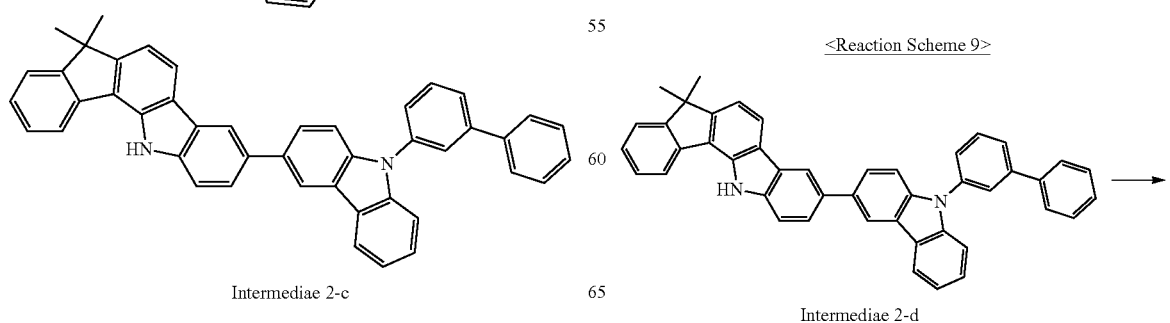

-continued

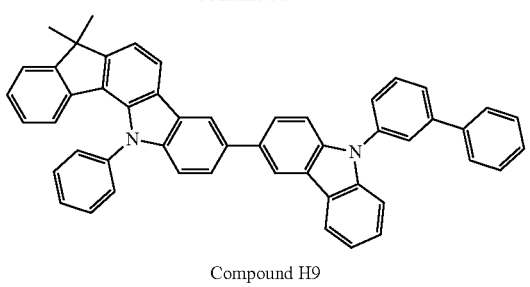

Compound H9

Compound H9 (8.9 g, 43%) was synthesized in the same manner as in Synthesis Example 1-(4), except that Intermediate 2-d was used instead of Intermediate 1-c.

MS (MALDI-TOF): m/z 676.29[M$^+$]

Synthesis Example 3: Synthesis of Compound H14

Synthesis Example 3-(1): Synthesis of Intermediate 3-a

Intermediate 3-a was synthesized according to Reaction Scheme 10.

<Reaction Scheme 10>

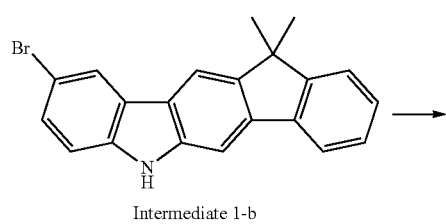

Intermediate 1-b

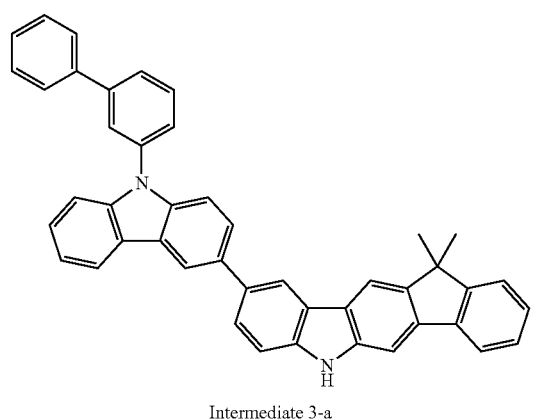

Intermediate 3-a

Intermediate 3-a (15.3 g, 57%) was synthesized in the same manner as in Synthesis Example 1-(3), except that 9-(biphenyl-3-yl)-9H-carbazol-3-ylboronic acid was used instead of N-phenylcarbazole-3-boronic acid.

Synthesis Example 3-(2): Synthesis of Compound H14

Compound H14 was synthesized according to Reaction Scheme 11.

<Reaction Scheme 11>

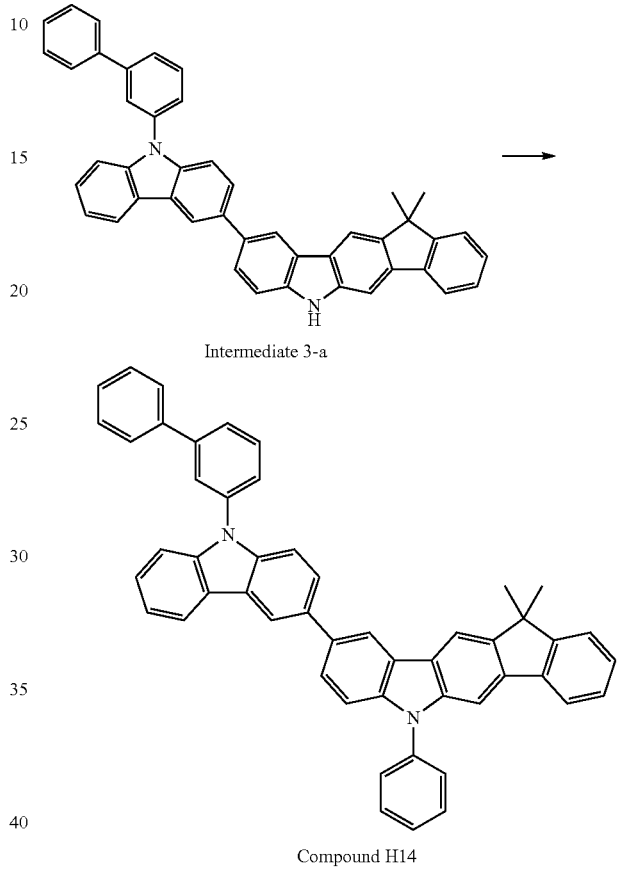

Compound H14

Compound H14 (12.6 g, 51%) was synthesized in the same manner as in Synthesis Example 1-(4), except that Intermediate 3-a was used instead of Intermediate 1-c.

MS (MALDI-TOF): m/z 676.29[M$^+$]

Synthesis Example 4: Synthesis of Compound H17

Synthesis Example 4-(1): Synthesis of Intermediate 4-a

Intermediate 4-a was synthesized according to Reaction Scheme 12.

<Reaction Scheme 12>

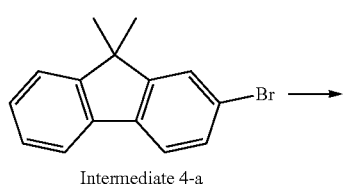

Intermediate 4-a

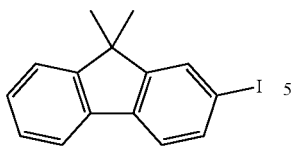

Intermediate 4-a (12.3 g, 65%) was synthesized in the same manner as in Synthesis Example 2-(1), except that 2-bromo-9,9-dimethylfluorene was used instead of 4-bromo-9,9-dimethylfluorene.

Synthesis Example 4-(2): Synthesis of Intermediate 4-b

Intermediate 4-b was synthesized according to Reaction Scheme 13.

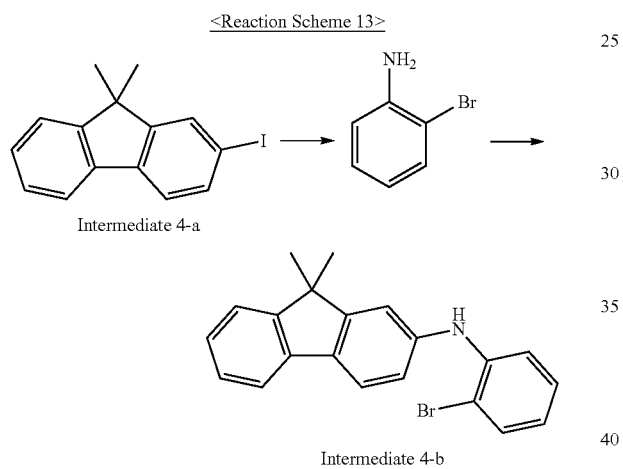

Intermediate 4-b (9.4 g, 61%) was synthesized in the same manner as in Synthesis Example 2-(2), except that Intermediate 4-a and 2-bromoaniline were used instead of Intermediate 2-a and 2,4-dibromoaniline, respectively.

Synthesis Example 4-(3): Synthesis of Intermediate 4-c

Intermediate 4-c was synthesized according to Reaction Scheme 14.

<Reaction Scheme 14>

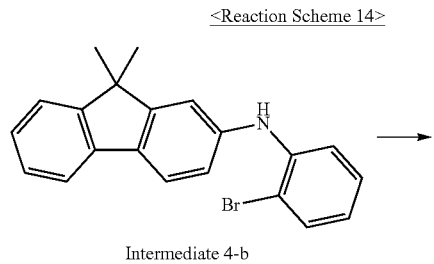

Intermediate 4-b

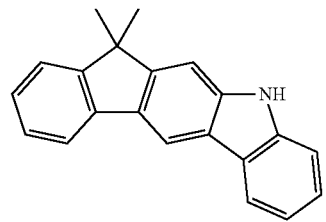

Intermediate 4-c

Intermediate 4-c (15 g, 78%) was synthesized in the same manner as in Synthesis Example 2-(3), except that Intermediate 4-b was used instead of Intermediate 2-b.

Synthesis Example 4-(4): Synthesis of Intermediate 4-d

Intermediate 4-d was synthesized according to Reaction Scheme 15.

<Reaction Scheme 15>

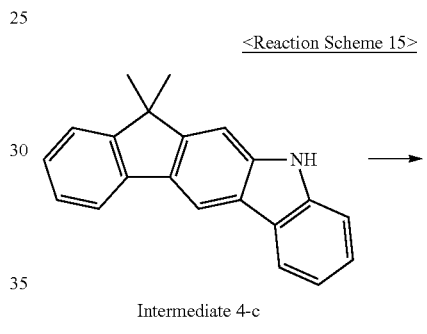

Intermediate 4-c

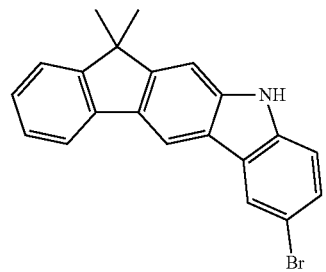

Intermediate 4-d

Intermediate 4-c (15.0 g, 0.053 mol) was dissolved in dimethylformamide (100 mL) in a 250 mL round bottom flask. The mixture was cooled to 0° C. To the solution was added dropwise a solution of N-bromosuccinic acid (10.4 g, 58 mmol) in dimethylformamide (50 mL). The resulting mixture was stirred at room temperature overnight. After completion of the reaction, the reaction mixture was extracted with ethyl acetate, heptane, and water. The organic layer was concentrated under reduced pressure and purified by column chromatography to give Intermediate 4-d (14.7 g, 77%).

Synthesis Example 4-(5): Synthesis of Intermediate 4-e

Intermediate 4-e was synthesized according to Reaction Scheme 16.

<Reaction Scheme 16>

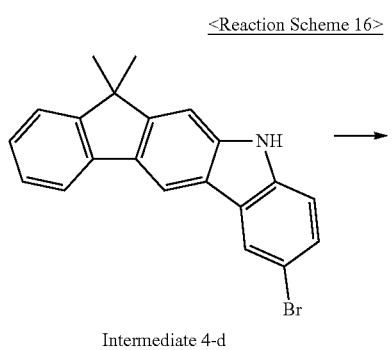

Intermediate 4-d

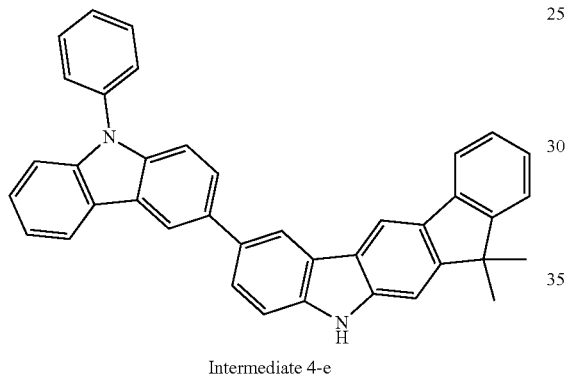

Intermediate 4-e

Intermediate 4-e (12.1 g, 62%) was synthesized in the same manner as in Synthesis Example 1-(3), except that Intermediate 4-d was used instead of Intermediate 1-b.

Synthesis Example 4-(6): Synthesis of Compound H17

Compound H17 was synthesized according to Reaction Scheme 17.

<Reaction Scheme 17>

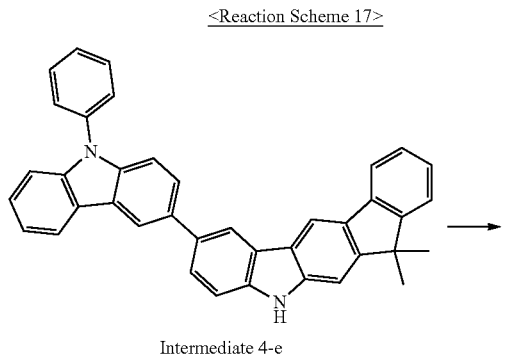

Intermediate 4-e

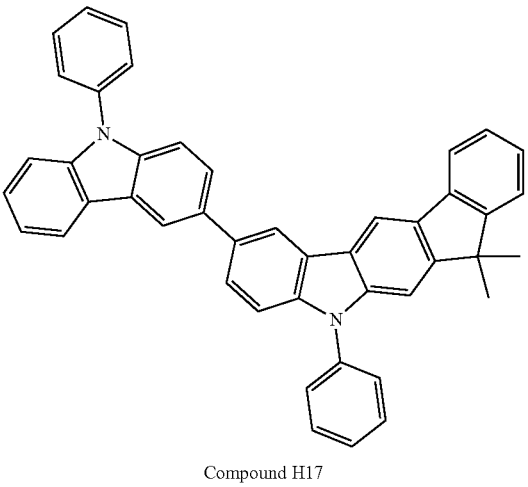

Compound H17

Compound H17 (13.7 g, 68%) was synthesized in the same manner as in Synthesis Example 1-(4), except that Intermediate 4-e was used instead of Intermediate 1-c.

MS (MALDI-TOF): m/z 600.26[M$^+$]

Synthesis Example 5: Synthesis of Compound H18

Synthesis Example 5-(1): Synthesis of Compound H18

Compound H18 was synthesized according to Reaction Scheme 18.

<Reaction Scheme 18>

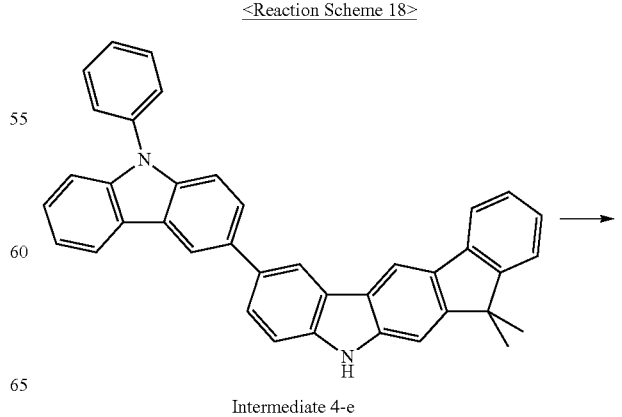

Intermediate 4-e

-continued

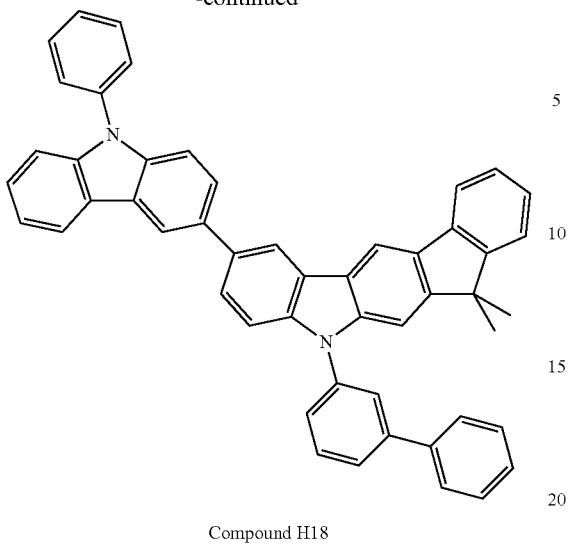

Compound H18

Compound H18 (6.8 g, 48%) was synthesized in the same manner as in Synthesis Example 1-(4), except that Intermediate 4-e and 1-bromo-3-phenylbenzene were used instead of Intermediate 1-c and bromobenzene, respectively.

MS (MALDI-TOF): m/z 676.29[M+]

Synthesis Example 6: Synthesis of Compound H22

Synthesis Example 6-(1): Synthesis of Intermediate 6-a

Intermediate 6-a was synthesized according to Reaction Scheme 19.

<Reaction Scheme 19>

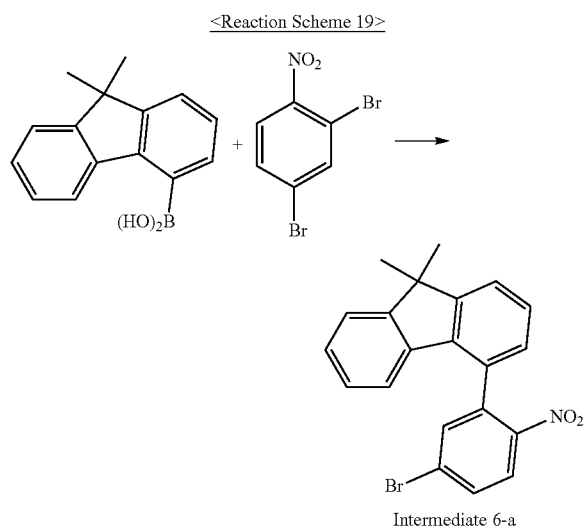

2,4-Dibromonitrobenzene (17.7 g, 0.063 mol), (9,9-dimethylfluoren-4-yl)boronic acid (12.5 g, 0.053 mol), tetrakis(triphenylphosphine)palladium (1.2 g, 1 mmol), and potassium carbonate (14.5 g, 0.105 mmol) were placed in a 250 mL round bottom flask and toluene (120 mL) and water (40 mL) were added thereto. The mixture was heated to reflux with stirring overnight. After completion of the reaction, the reactor was cooled to room temperature. The reaction mixture was extracted with ethyl acetate. The organic layer was concentrated under reduced pressure and purified by column chromatography to give Intermediate 6-b (15.2 g, 73%).

Synthesis Example 6-(2): Synthesis of Intermediate 6-b

Intermediate 6-b was synthesized according to Reaction Scheme 20.

<Reaction Scheme 20>

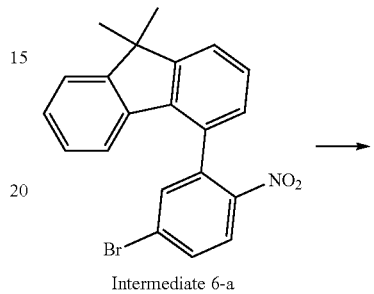

Intermediate 6-a

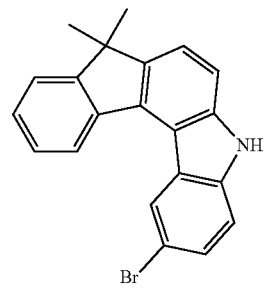

Intermediate 6-b

Intermediate 6-a (15.2 g, 0.039 mol) and triphenylphosphine (30.3 g, 0.116 mol) were placed in a 500 mL reactor and 1,2-dichlorobenzene (150 mL) was added thereto. The reactor was heated to 120° C. The mixture was stirred at the same temperature overnight. After completion of the reaction, the reaction solution was concentrated by heating and purified by column chromatography to give Intermediate 6-b (9.4 g, 67%).

Synthesis Example 6-(3): Synthesis of Intermediate 6-c

Intermediate 6-c was synthesized according to Reaction Scheme 21.

<Reaction Scheme 21>

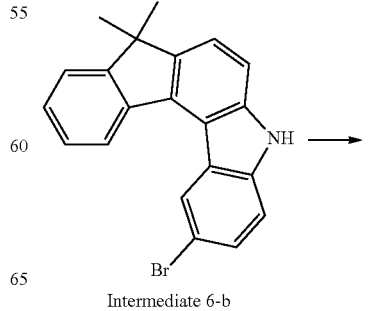

Intermediate 6-b

-continued

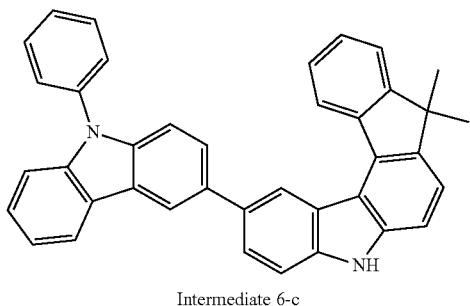
Intermediate 6-c

Intermediate 6-c (8.2 g, 57%) was synthesized in the same manner as in Synthesis Example 1-(3), except that Intermediate 6-b was used instead of Intermediate 1-b.

Synthesis Example 6-(4): Synthesis of Compound H22

Compound H22 was synthesized according to Reaction Scheme 22.

<Reaction Scheme 22>

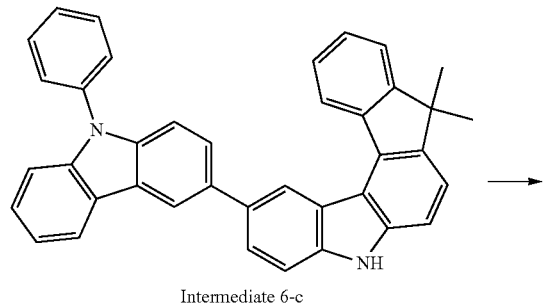
Compound H22

Compound H22 (7.8 g, 47%) was synthesized in the same manner as in Synthesis Example 5-(1), except that Intermediate 6-c was used instead of Intermediate 4-e.

MS (MALDI-TOF): m/z 676.29[M⁺]

Synthesis Example 7: Synthesis of Compound H46

Synthesis Example 7-(1): Synthesis of Intermediate 7-a

Intermediate 7-a was synthesized according to Reaction Scheme 23.

<Reaction Scheme 23>

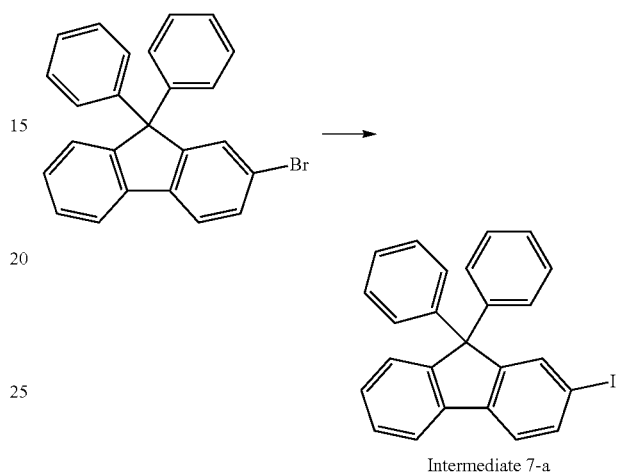
Intermediate 7-a

Intermediate 7-a (20.3 g, 67%) was synthesized in the same manner as in Synthesis Example 2-(1), except that 2-bromo-9,9-diphenylfluorene was used instead of 4-bromo-9,9-dimethylfluorene.

Synthesis Example 7-(2): Synthesis of Intermediate 7-b

Intermediate 7-b was synthesized according to Reaction Scheme 24.

<Reaction Scheme 24>

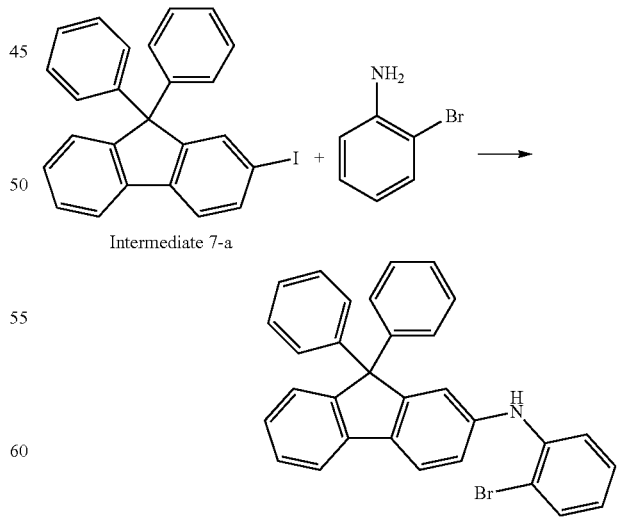
Intermediate 7-b

Intermediate 7-b (12.5 g, 62%) was synthesized in the same manner as in Synthesis Example 2-(2), except that Intermediate 7-a and 2-bromoaniline were used instead of Intermediate 2-a and 2,4-dibromoaniline, respectively.

Synthesis Example 7-(3): Synthesis of Intermediate 7-c

Intermediate 7-c was synthesized according to Reaction Scheme 25.

<Reaction Scheme 25>

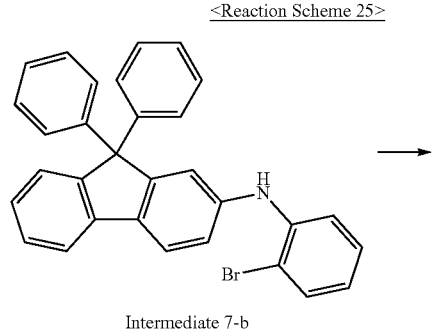

Intermediate 7-b

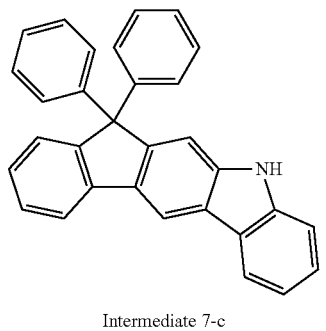

Intermediate 7-c

Intermediate 7-c (15.2 g, 76%) was synthesized in the same manner as in Synthesis Example 2-(3), except that Intermediate 7-b was used instead of Intermediate 2-b.

Synthesis Example 7-(4): Synthesis of Intermediate 7-d

Intermediate 7-d was synthesized according to Reaction Scheme 26.

<Reaction Scheme 26>

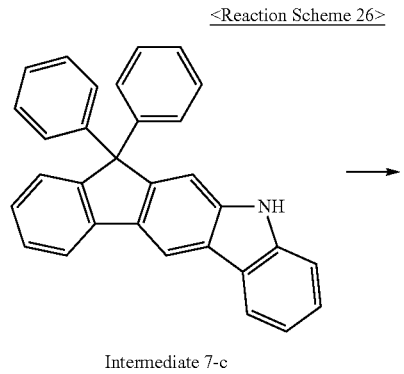

Intermediate 7-c

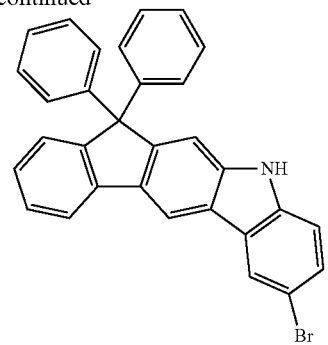

Intermediate 7-d

Intermediate 7-c (15.0 g, 0.037 mol) was placed in a 250 mL round bottom flask and was then dissolved by the addition of dimethylformamide (100 mL). The solution was cooled to 0° C. To the solution was added dropwise a solution of N-bromosuccinic acid (7.2 g, 40 mmol) in dimethylformamide (50 mL). The resulting mixture was stirred at room temperature overnight. After completion of the reaction, the reaction mixture was extracted with ethyl acetate, heptane, and water. The organic layer was concentrated under reduced pressure and purified by column chromatography to give Intermediate 7-d (15.1 g, 84.3%).

Synthesis Example 7-(5): Synthesis of Intermediate 7-e

Intermediate 7-e was synthesized according to Reaction Scheme 27.

<Reaction Scheme 27>

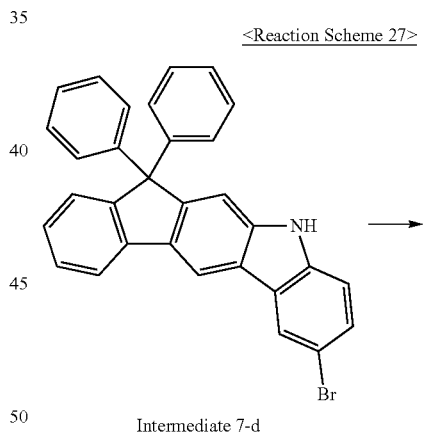

Intermediate 7-d

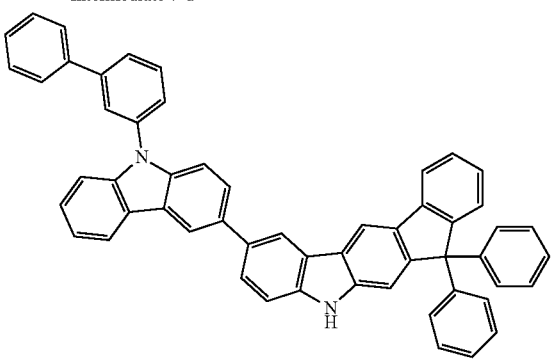

Intermediate 7-e

Intermediate 13-e (11.4 g, 61%) was synthesized in the same manner as in Synthesis Example 1-(3), except that Intermediate 7-d and 9-(1,1'-biphenyl-4-yl)-9H-carbazole-3-boronic acid were used instead of Intermediate 1-b and 9H-phenylcarbazole-3-boronic acid, respectively.

Synthesis Example 7-(6): Synthesis of Compound H46

Compound H46 was synthesized according to Reaction Scheme 28.

<Reaction Scheme 28>

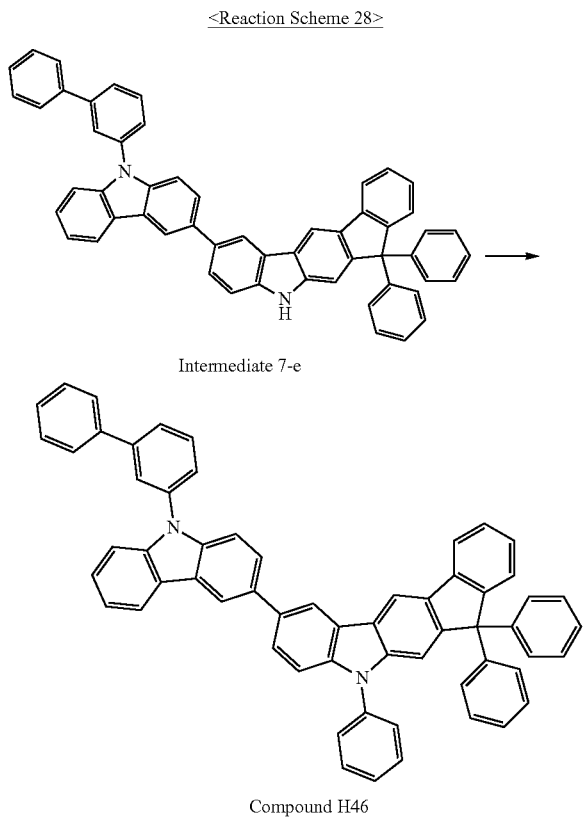

Compound H46

Compound H46 (12.6 g, 66%) was synthesized in the same manner as in Synthesis Example 1-(4), except that Intermediate 7-e was used instead of Intermediate 1-c.
MS (MALDI-TOF): m/z 800.32[M⁺]

Synthesis Example 8: Synthesis of Compound E6

Synthesis Example 8-(1): Synthesis of Intermediate 8-a

Intermediate 8-a was synthesized according to Reaction Scheme 29.

<Reaction Scheme 29>

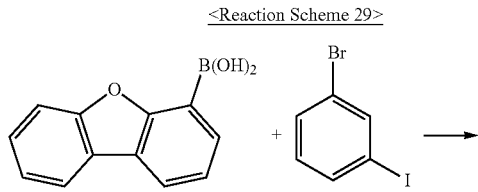

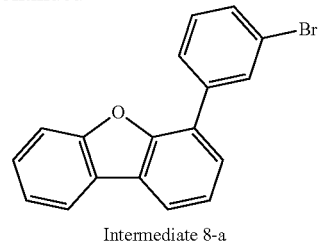

Intermediate 8-a

1-Bromo-3-iodobenzene (30.0 g, 0.106 mol), dibenzofuran-4-boronic acid (22.5 g, 0.106 mol), tetrakis(triphenylphosphine)palladium (2.5 g, 0.002 mol), and potassium carbonate (29.3 g, 0.212 mol) were placed in a 1 L round bottom flask and toluene (270 mL) and water (90 mL) were added thereto. The temperature of the reactor was raised to 80° C. The mixture was stirred at the same temperature overnight. After completion of the reaction, the reactor was cooled to room temperature. The reaction mixture was extracted with ethyl acetate. The organic layer was concentrated under reduced pressure and purified by column chromatography to give Intermediate 8-a (26.5 g, 77%).

Synthesis Example 8-(2): Synthesis of Intermediate 8-b

Intermediate 8-b was synthesized according to Reaction Scheme 30.

<Reaction Scheme 30>

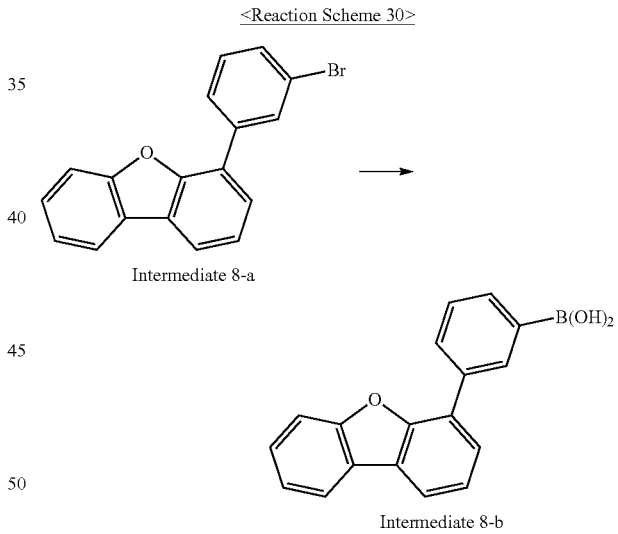

Intermediate 8-a (26.5 g, 0.082 mol) was placed in a 1 L round bottom flask and was then dissolved by the addition of tetrahydrofuran (220 mL). The solution was cooled to −78° C. under a nitrogen atmosphere. To the cooled solution was slowly added dropwise n-butyllithium (61.5 mL, 0.098 mol) over 30 min. The mixture was stirred at the same temperature for 1 h. Trimethyl borate (11.1 g, 0.107 mol) was added dropwise at the same temperature. Stirring was continued at room temperature overnight. The reaction solution was acidified by dropwise addition of 2 N hydrochloric acid, stirred for 1 h, and extracted with ethyl acetate. The organic layer was concentrated under reduced pressure and recrystallized from n-hexane to give Intermediate 8-b (15.6 g, 66%).

Synthesis Example 8-(3): Synthesis of Compound E6

Compound E6 was synthesized according to Reaction Scheme 31.

<Reaction Scheme 31>

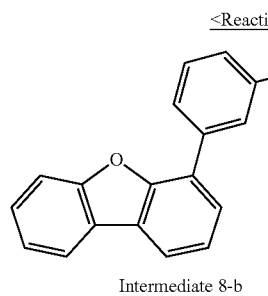

Intermediate 8-b

→

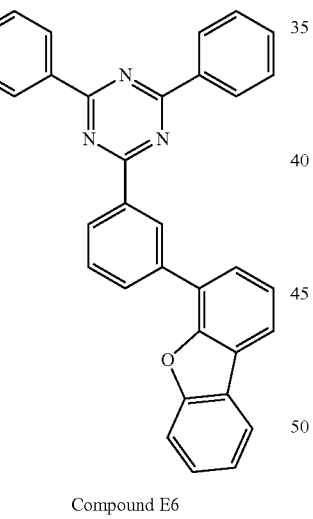

Compound E6

2-Bromo-4,6-diphenyl-1,3,5-triazine (10.0 g, 0.032 mol), Intermediate 8-b (8.9 g, 0.031 mol), tetrakis(triphenylphosphine)palladium (0.6 g, 0.001 mol), and potassium carbonate (7.1 g, 0.052 mol) were placed in a 300 mL round bottom flask and toluene (70 mL), ethanol (30 mL), and water (20 mL) were added thereto. The mixture was heated to reflux with stirring overnight. After completion of the reaction, the reactor was cooled to room temperature. The reaction mixture was extracted with ethyl acetate. The organic layer was concentrated under reduced pressure and purified by column chromatography to give Compound E6 (5.8 g, 34%).

MS (MALDI-TOF): m/z 475.17[M$^+$]

Synthesis Example 9: Synthesis of Compound E12

Synthesis Example 9-(1): Synthesis of Intermediate 9-a

Intermediate 9-a was synthesized according to Reaction Scheme 32.

<Reaction Scheme 32>

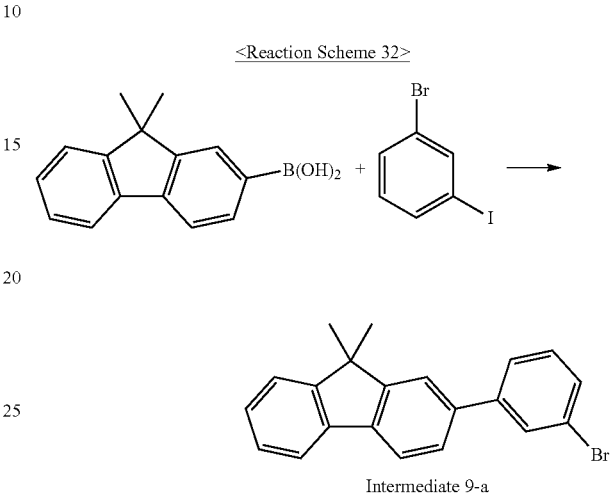

Intermediate 9-a

Intermediate 9-a (5.6 g, 48%) was synthesized in the same manner as in Synthesis Example 8-(1), except that 9,9-dimethyl-9H-fluoren-2-ylboronic acid was used instead of dibenzofuran-4-boronic acid.

Synthesis Example 9-(2): Synthesis of Intermediate 9-b

Intermediate 9-b was synthesized according to Reaction Scheme 33.

<Reaction Scheme 33>

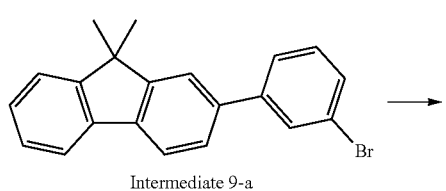

Intermediate 9-a

→

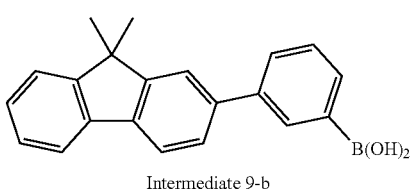

Intermediate 9-b

Intermediate 9-b (6.1 g, 43%) was synthesized in the same manner as in Synthesis Example 8-(2), except that Intermediate 9-a was used instead of Intermediate 8-a.

Synthesis Example 9-(3): Synthesis of Compound E12

Compound E12 was synthesized according to Reaction Scheme 34.

<Reaction Scheme 34>

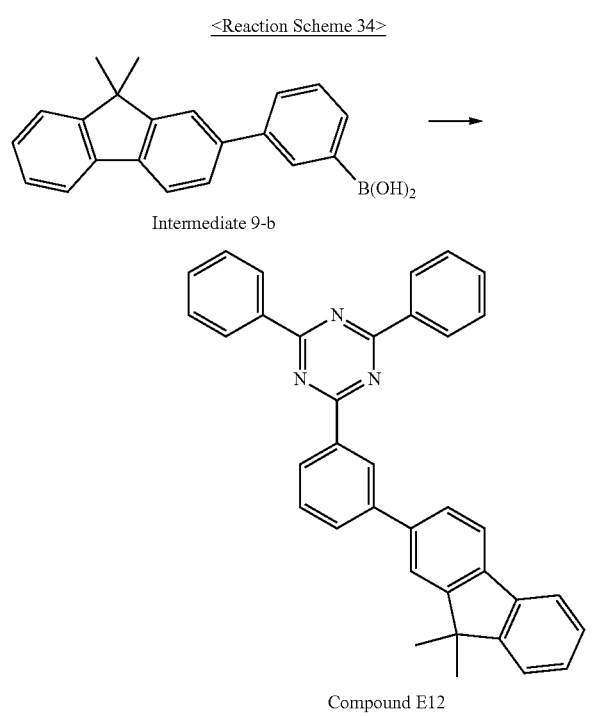

Compound E12

Compound E12 (5.4 g, 52%) was synthesized in the same manner as in Synthesis Example 8-(3), except that Intermediate 9-b and 2-(4-bromophenyl)-4,6-diphenyl-1,3,5-triazine were used instead of Intermediate 8-b and 2-bromo-4,6-diphenyl-1,3,5-triazine, respectively.

MS (MALDI-TOF): m/z 501.22[M$^+$]

Synthesis Example 10: Synthesis of Compound E23

Synthesis Example 10-(1): Synthesis of Intermediate 10-a

Intermediate 10-a was synthesized according to Reaction Scheme 35.

<Reaction Scheme 35>

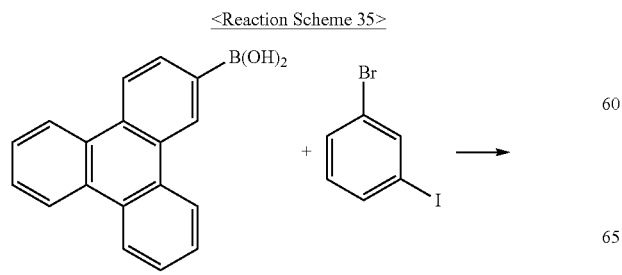

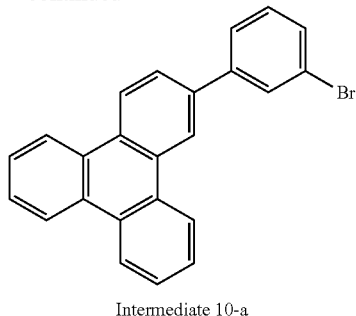

Intermediate 10-a

Intermediate 10-a (6.2 g, 47%) was synthesized in the same manner as in Synthesis Example 8-(1), except that 2-triphenyleneboronic acid was used instead of dibenzofuran-4-boronic acid.

Synthesis Example 10-(2): Synthesis of Intermediate 10-b

Intermediate 10-b was synthesized according to Reaction Scheme 36.

<Reaction Scheme 36>

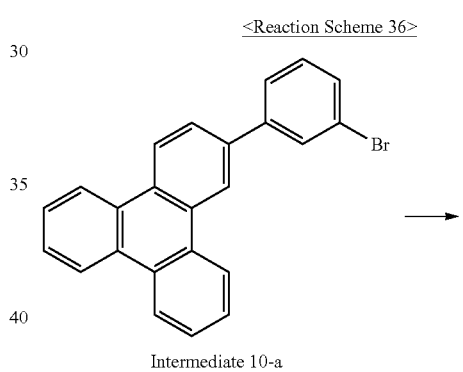

Intermediate 10-a

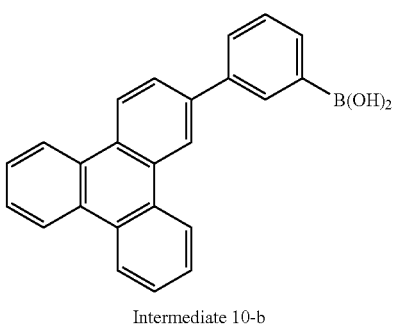

Intermediate 10-b

Intermediate 10-b (4.1 g, 56%) was synthesized in the same manner as in Synthesis Example 8-(2), except that Intermediate 10-a was used instead of Intermediate 8-a.

Synthesis Example 10-(3): Synthesis of Compound E23

Compound E23 was synthesized according to Reaction Scheme 37.

<Reaction Scheme 37>

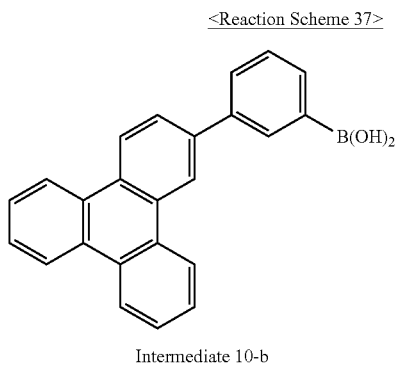

Intermediate 10-b

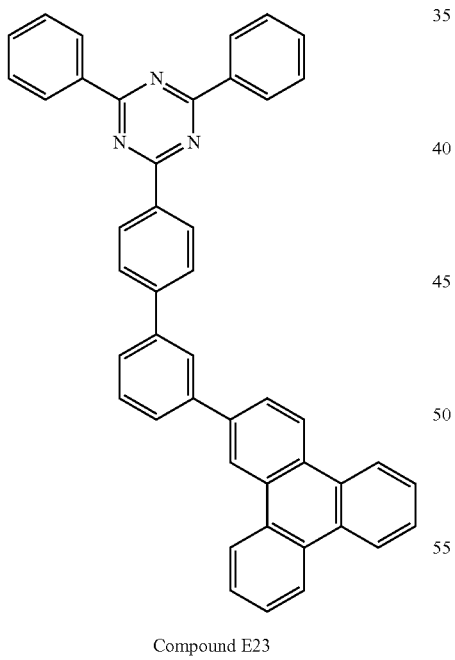

Compound E23

Compound E23 (5.4 g, 49%) was synthesized in the same manner as in Synthesis Example 8-(3), except that Intermediate 10-b and 2-(4-bromophenyl)-4,6-diphenyl-1,3,5-triazine were used instead of Intermediate 8-b and 2-bromo-4,6-diphenyl-1,3,5-triazine, respectively.

MS (MALDI-TOF): m/z 611.24[M+]

Synthesis Example 11: Synthesis of Compound E26

Synthesis Example 11-(1): Synthesis of Intermediate 11-a

Intermediate 11-a was synthesized according to Reaction Scheme 38.

<Reaction Scheme 38>

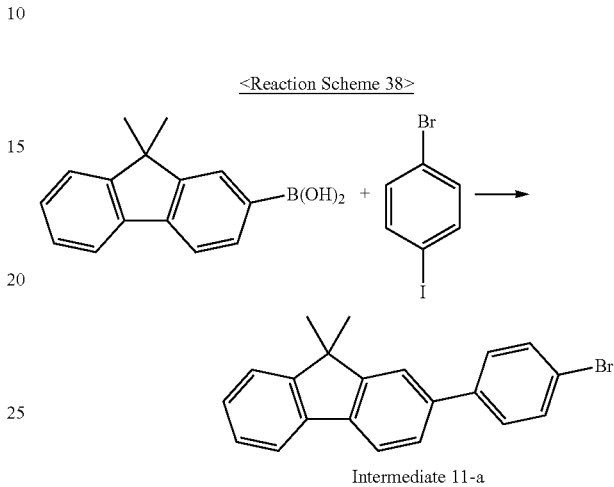

Intermediate 11-a

Intermediate 11-a (7.7 g, 67%) was synthesized in the same manner as in Synthesis Example 8-(1), except that 9,9-dimethyl-9H-fluoren-2-ylboronic acid and 1-bromo-4-iodobenzene were used instead of dibenzofuran-4-boronic acid and 1-bromo-3-iodobenzene, respectively.

Synthesis Example 11-(2): Synthesis of Intermediate 11-b

Intermediate 11-b was synthesized according to Reaction Scheme 39.

<Reaction Scheme 39>

Intermediate 11-a

Intermediate 11-b

Intermediate 11-b (7.1 g, 51%) was synthesized in the same manner as in Synthesis Example 8-(2), except that Intermediate 11-a was used instead of Intermediate 8-a.

Synthesis Example 11-(3): Synthesis of Compound E26

Compound E26 was synthesized according to Reaction Scheme 40.

<Reaction Scheme 40>

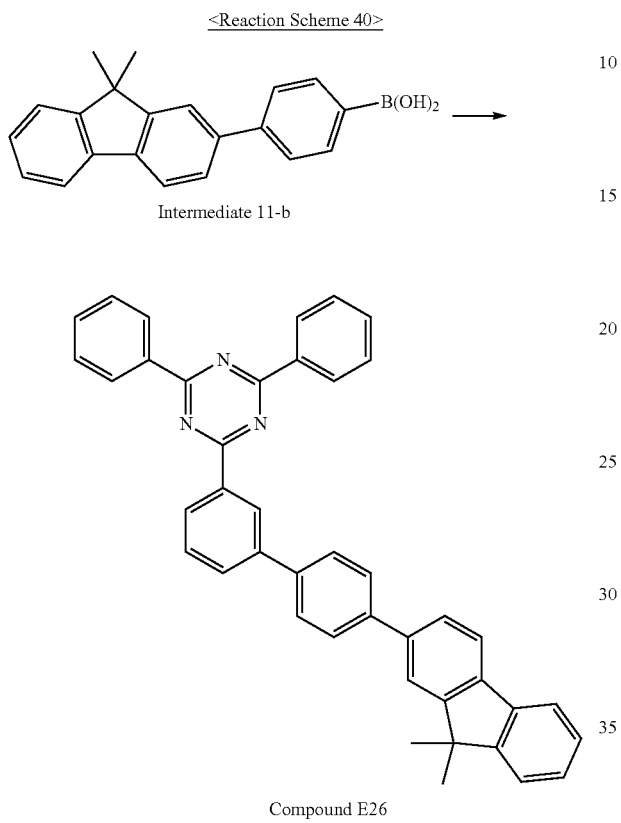

Intermediate 11-b

Compound E26

Compound E26 (6.4 g, 66%) was synthesized in the same manner as in Synthesis Example 8-(3), except that Intermediate 11-b and 2-(4-bromophenyl)-4,6-diphenyl-1,3,5-triazine were used instead of Intermediate 8-b and 2-bromo-4,6-diphenyl-1,3,5-triazine, respectively.

MS (MALDI-TOF): m/z 577.25[M$^+$]

Synthesis Example 12: Synthesis of Compound E72

Synthesis Example 12-(1): Synthesis of Intermediate 12-a

Intermediate 12-a was synthesized according to Reaction Scheme 41.

<Reaction Scheme 41>

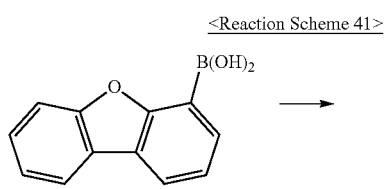

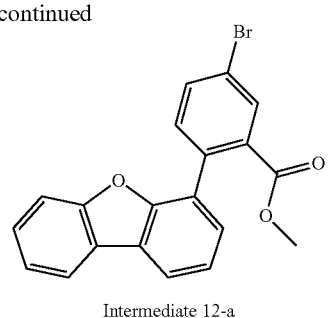

Intermediate 12-a

4-Bromomethyl-2-iodobenzoate (50.0 g, 0.147 mol), dibenzofuran-4-boronic acid (40.1 g, 0.176 mol), tetrakis(triphenylphosphine)palladium (3.4 g, 0.003 mol), and potassium carbonate (40.5 g, 0.293 mol) were placed in a 1 L round bottom flask and toluene (350 mL), ethanol (150 mL), and water (100 mL) were added thereto. The temperature of the reactor was raised to 80° C. The mixture was stirred at the same temperature overnight. After completion of the reaction, the reactor was cooled to room temperature. The reaction mixture was extracted with ethyl acetate. The organic layer was concentrated under reduced pressure and purified by column chromatography to give Intermediate 12-a (38.0 g, 53%).

Synthesis Example 12-(2): Synthesis of Intermediate 12-b

Intermediate 12-b was synthesized according to Reaction Scheme 42.

<Reaction Scheme 42>

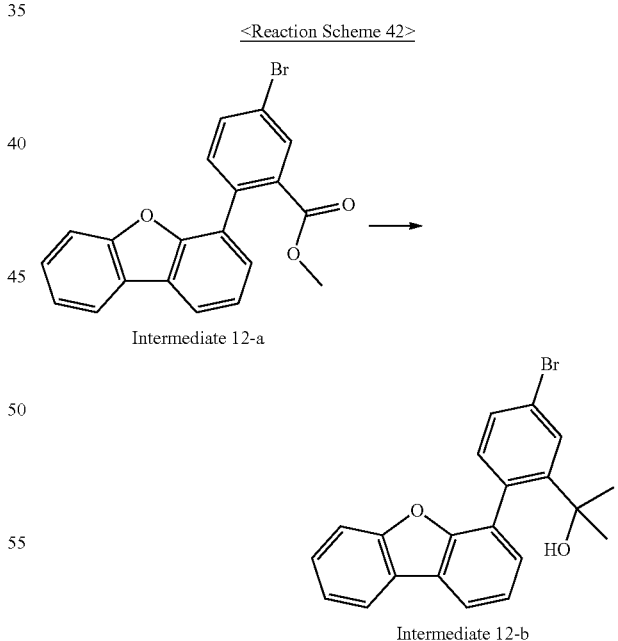

Intermediate 12-a (38.0 g, 0.100 mol) and tetrahydrofuran (380 mL) were placed in a 1 L round bottom flask. The mixture was stirred at 0° C. under a stream of nitrogen gas. To the cooled mixture was added dropwise methylmagnesium bromide (3 M) (83.1 mL. 0.249 mol). The resulting mixture was stirred at room temperature for 1 h and refluxed with stirring for 5 h. The reaction was quenched with the addition of an aqueous solution of ammonium chloride. The reaction solution was extracted with ethyl acetate and water. The organic layer was concentrated under reduced pressure and purified by column chromatography to give Intermediate 12-b (24.5 g, 65%).

Synthesis Example 12-(3): Synthesis of Intermediate 12-c

Intermediate 12-c was synthesized according to Reaction Scheme 43.

<Reaction Scheme 43>

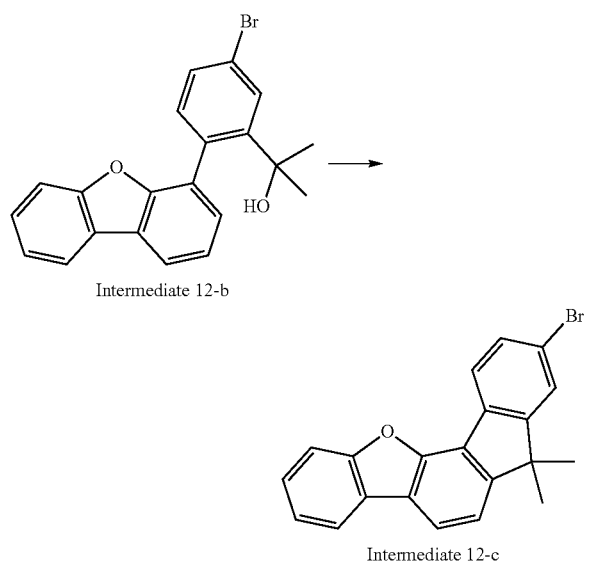

Intermediate 12-b

Intermediate 12-c

Intermediate 12-b (24.5 g, 0.064 mol), acetic acid (200 mL), and hydrochloric acid (2 mL) were stirred under heating overnight in a 500 mL round bottom flask. After completion of the reaction, the reaction mixture was cooled to room temperature, poured into 300 mL of water in a beaker, and stirred. The resulting solid was filtered off and the filtrate was purified by column chromatography to give Intermediate 12-c (20.0 g, 85%).

Synthesis Example 12-(4): Synthesis of Intermediate 12-d

Intermediate 12-d was synthesized according to Reaction Scheme 44.

<Reaction Scheme 44>

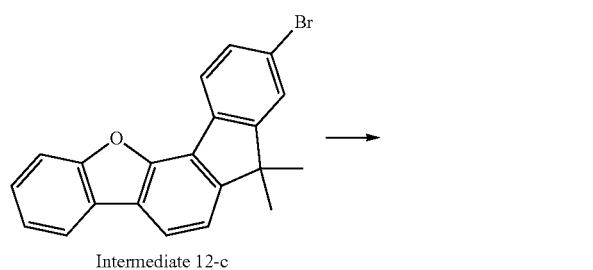

Intermediate 12-c

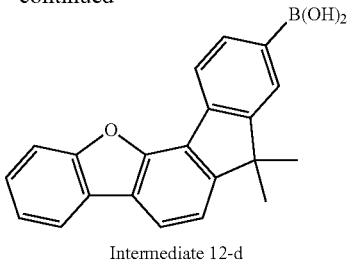

Intermediate 12-d

Intermediate 12-c (20.0 g, 0.055 mol) was dissolved in tetrahydrofuran (160 mL) in a 500 mL round bottom flask. The solution was cooled to −78° C. under a stream of nitrogen gas and n-butyllithium (1.6 M) (39.6 mL, 0.063 mol) was slowly added dropwise thereto. After stirring at the same temperature for 1 h, trimethyl borate (7.4 g, 0.072 mol) was added portionwise. After the trimethyl borate addition was completed, the resulting mixture was stirred at room temperature overnight. After completion of the reaction, the reaction mixture was acidified with 2 N hydrochloric acid, stirred for 30 min, and extracted with ethyl acetate and water. The organic layer was concentrated under reduced pressure and recrystallized from heptane to give Intermediate 12-d (12.3 g, 68%).

Synthesis Example 12-(5): Synthesis of Compound E72

Compound E72 was synthesized according to Reaction Scheme 45.

<Reaction Scheme 45>

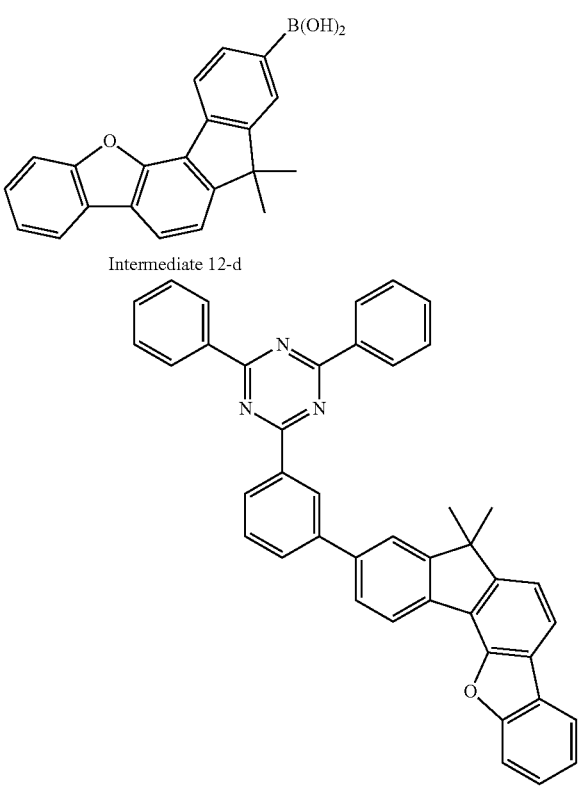

Compound E72

Compound E72 (10.9 g, 52%) was synthesized in the same manner as in Synthesis Example 8-(3), except that Intermediate 12-d and 2-(4-bromophenyl)-4,6-diphenyl-1,3,5-triazine were used instead of Intermediate 8-b and 2-bromo-4,6-diphenyl-1,3,5-triazine, respectively.

MS (MALDI-TOF): m/z 591.23 [M$^+$]

Synthesis Example 13: Synthesis of Compound E76

Synthesis Example 13-(1): Synthesis of Intermediate 13-a

Intermediate 13-a was synthesized according to Reaction Scheme 46.

<Reaction Scheme 46>

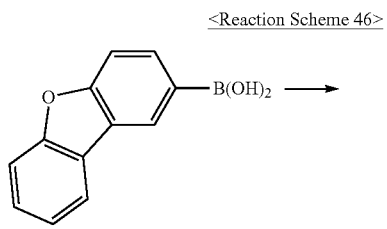

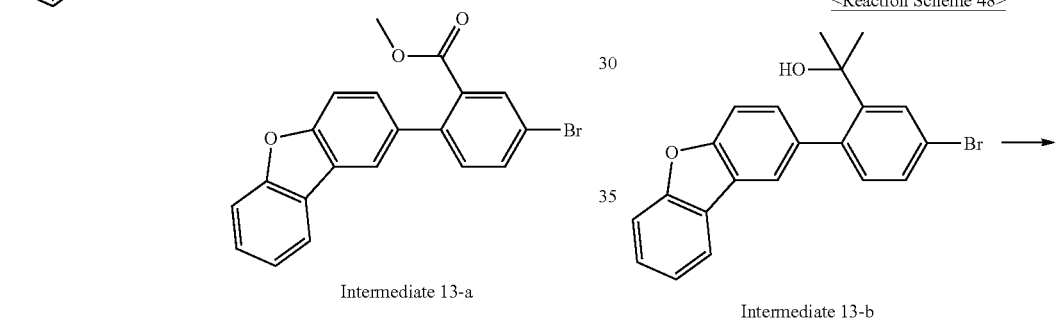

Intermediate 13-a

Intermediate 13-a (7.1 g, 68%) was synthesized in the same manner as in Synthesis Example 12-(1), except that dibenzofuran-2-boronic acid was used instead of dibenzofuran-4-boronic acid.

Synthesis Example 13-(2): Synthesis of Intermediate 13-b

Intermediate 13-b was synthesized according to Reaction Scheme 47.

<Reaction Scheme 47>

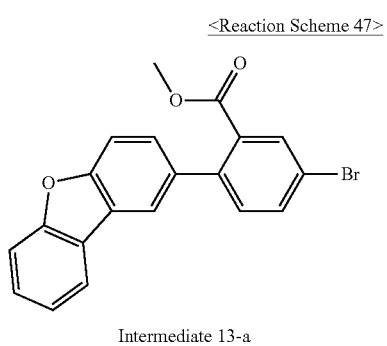

Intermediate 13-a

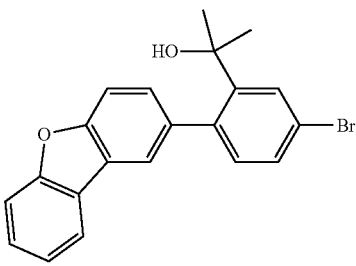

Intermediate 13-b

Intermediate 13-b (5.3 g, 47%) was synthesized in the same manner as in Synthesis Example 12-(2), except that Intermediate 13-a was used instead of Intermediate 12-a.

Synthesis Example 13-(3): Synthesis of Intermediate 13-c

Intermediate 13-c was synthesized according to Reaction Scheme 48.

<Reaction Scheme 48>

Intermediate 13-b

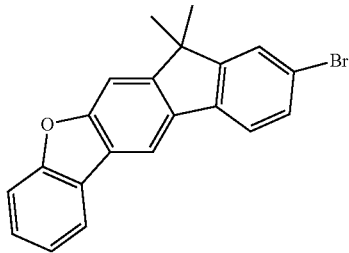

Intermediate 13-c

Intermediate 13-c (6.4 g, 61%) was synthesized in the same manner as in Synthesis Example 12-(3), except that Intermediate 13-b was used instead of Intermediate 12-b.

Synthesis Example 13-(4): Synthesis of Intermediate 13-d

Intermediate 13-d was synthesized according to Reaction Scheme 49.

<Reaction Scheme 49>

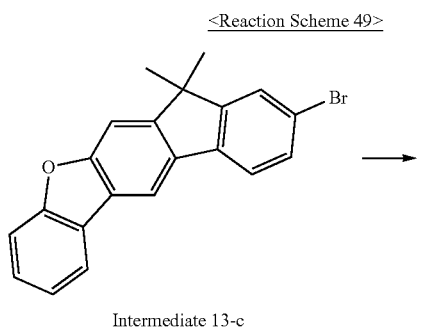

Intermediate 13-c

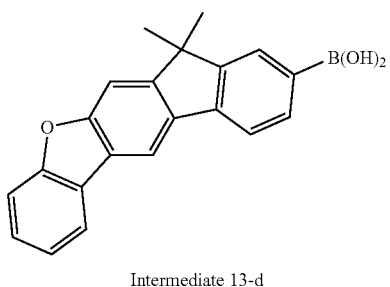

Intermediate 13-d

Intermediate 13-d (6.6 g, 63%) was synthesized in the same manner as in Synthesis Example 12-(4), except that Intermediate 13-c was used instead of Intermediate 12-c.

Synthesis Example 13-(5): Synthesis of Compound E76

Compound E76 was synthesized according to Reaction Scheme 50.

<Reaction Scheme 50>

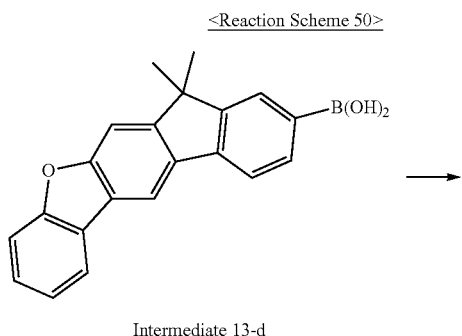

Intermediate 13-d

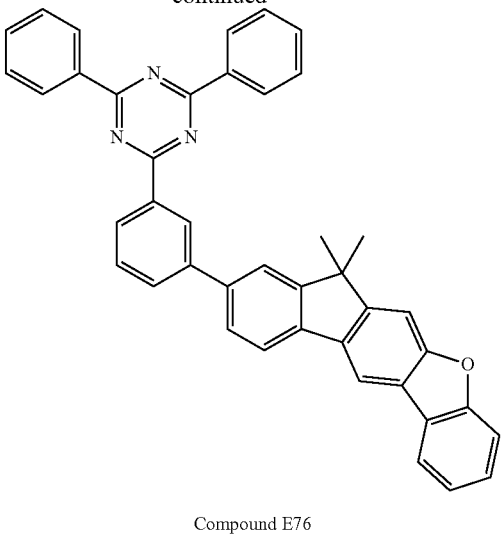

Compound E76

Compound E76 (5.1 g, 48%) was synthesized in the same manner as in Synthesis Example 12-(5), except that Intermediate 13-d and 2-(4-bromophenyl)-4,6-diphenyl-1,3,5-triazine were used instead of Intermediate 12-d and 2-bromo-4,6-diphenyl-1,3,5-triazine, respectively.

MS (MALDI-TOF): m/z 591.23 [M⁺]

Examples 1-14: Fabrication of Organic Light Emitting Devices

Example 1

ITO glass was patterned to have a light emitting area of 2 mm×2 mm, followed by cleaning. After the cleaned ITO glass was mounted in a vacuum chamber, the base pressure was adjusted to $1\times10^{-6}$ torr. HATCN (50 Å), NPD (900 Å), and a mixture of Compound H1 as a first compound and Compound E6 as a second compound in a weight ratio of 5:5 were deposited on the ITO and doped with 7% of a green phosphorescent dopant (GD) to form a 400 Å thick light emitting layer. Thereafter, an ET: Liq (1:1) layer (300 Å), a Liq layer (10 Å), and an Al layer (1,000 Å) were formed in this order on the light emitting layer to fabricate an organic light emitting device. The luminescent properties of the organic light emitting device were measured at 0.4 mA.

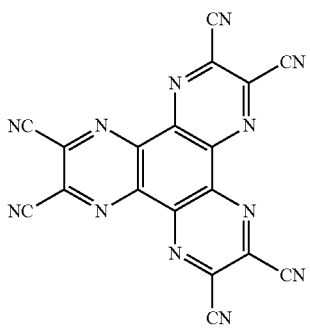

HATCN

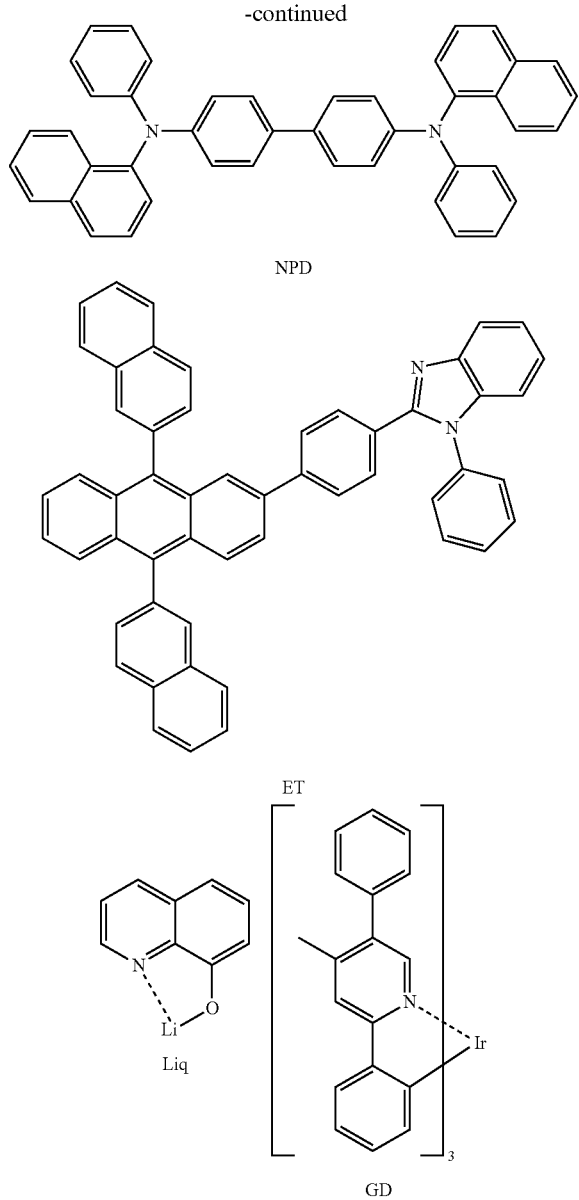

Example 2

An organic light emitting device was fabricated in the same manner as in Example 1, except that Compound E12 was used instead of Compound E6 to form a light emitting layer.

Example 3

An organic light emitting device was fabricated in the same manner as in Example 1, except that Compound H9 was used instead of Compound H1 and Compound E23 was used instead of Compound E6 to form a light emitting layer.

Example 4

An organic light emitting device was fabricated in the same manner as in Example 1, except that Compound H9 was used instead of Compound H1 and Compound E26 was used instead of Compound E6 to form a light emitting layer.

Example 5

An organic light emitting device was fabricated in the same manner as in Example 1, except that Compound H14 was used instead of Compound H1 and Compound E72 was used instead of Compound E6 to form a light emitting layer.

Example 6

An organic light emitting device was fabricated in the same manner as in Example 1, except that Compound H14 was used instead of Compound H1 and Compound E76 was used instead of Compound E6 to form a light emitting layer.

Example 7

An organic light emitting device was fabricated in the same manner as in Example 1, except that Compound H17 was used instead of Compound H1 to form a light emitting layer.

Example 8

An organic light emitting device was fabricated in the same manner as in Example 1, except that Compound H17 was used instead of Compound H1 and Compound E12 was used instead of Compound E6 to form a light emitting layer.

Example 9

An organic light emitting device was fabricated in the same manner as in Example 1, except that Compound H18 was used instead of Compound H1 and Compound E23 was used instead of Compound E6 to form a light emitting layer.

Example 10

An organic light emitting device was fabricated in the same manner as in Example 1, except that Compound H18 was used instead of Compound H1 and Compound E26 was used instead of Compound E6 to form a light emitting layer.

Example 11

An organic light emitting device was fabricated in the same manner as in Example 1, except that Compound H22 was used instead of Compound H1 and Compound E72 was used instead of Compound E6 to form a light emitting layer.

Example 12

An organic light emitting device was fabricated in the same manner as in Example 1, except that Compound H22 was used instead of Compound H1 and Compound E76 was used instead of Compound E6 to form a light emitting layer.

Example 13

An organic light emitting device was fabricated in the same manner as in Example 1, except that Compound H46 was used instead of Compound H1 and Compound E12 was used instead of Compound E6 to form a light emitting layer.

Example 14

An organic light emitting device was fabricated in the same manner as in Example 1, except that Compound H46 was used instead of Compound H1 and Compound E72 was used instead of Compound E6 to form a light emitting layer.

Comparative Examples 1-13

Organic light emitting devices were fabricated in the same manner as in Example 1, except that one of Compounds H1-H46 and E6-E76 shown in Table 1 and a phosphorescent dopant (GD) were co-deposited in a weight ratio 100:7 to form a light emitting layer.

TABLE 1

|  | First host | Second host | wt:wt | Driving voltage (V) | Luminous efficiency (cd/A) | CIEx | CIEy | T95 (h) 6000 nit |
|---|---|---|---|---|---|---|---|---|
| Example 1 | Compound H1 | Compound E6 | 5:5 | 3.98 | 48.9 | 0.334 | 0.631 | 165 |
| Example 2 | Compound H1 | Compound E12 | 5:5 | 3.88 | 46.5 | 0.324 | 0.629 | 157 |
| Example 3 | Compound H9 | Compound E23 | 5:5 | 4.05 | 48.5 | 0.326 | 0.633 | 186 |
| Example 4 | Compound H9 | Compound E26 | 5:5 | 4.01 | 50.7 | 0.332 | 0.632 | 204 |
| Example 5 | Compound H14 | Compound E72 | 5:5 | 4.22 | 49.8 | 0.324 | 0.624 | 175 |
| Example 6 | Compound H14 | Compound E76 | 5:5 | 4.24 | 48.3 | 0.328 | 0.625 | 164 |
| Example 7 | Compound H17 | Compound E6 | 5:5 | 3.91 | 51.4 | 0.331 | 0.623 | 177 |
| Example 8 | Compound H17 | Compound E12 | 5:5 | 3.88 | 52.6 | 0.322 | 0.624 | 189 |
| Example 9 | Compound H18 | Compound E23 | 5:5 | 4.11 | 55.3 | 0.326 | 0.628 | 186 |
| Example 10 | Compound H18 | Compound E26 | 5:5 | 3.96 | 50.5 | 0.324 | 0.623 | 168 |
| Example 11 | Compound H22 | Compound E72 | 5:5 | 4.23 | 49.5 | 0.325 | 0.627 | 160 |
| Example 12 | Compound H22 | Compound E76 | 5:5 | 4.17 | 51.8 | 0.328 | 0.624 | 156 |
| Example 13 | Compound H46 | Compound E12 | 5:05 | 3.89 | 50.3 | 0.326 | 0.627 | 150 |
| Example 14 | Compound H46 | Compound E72 | 5:05 | 3.97 | 51.2 | 0.324 | 0.625 | 148 |
| Comparative Example 1 | Compound H1 |  | 1 | 5.21 | 6.2 | 0.327 | 0.623 | 5 |
| Comparative Example 2 | Compound H9 |  | 1 | 4.98 | 6 | 0.324 | 0.625 | 7 |
| Comparative Example 3 | Compound H14 |  | 1 | 5.02 | 7.5 | 0.332 | 0.635 | 6 |
| Comparative Example 4 | Compound H17 |  | 1 | 4.88 | 8.3 | 0.347 | 0.631 | 6 |
| Comparative Example 5 | Compound H18 |  | 1 | 5.22 | 8.1 | 0.336 | 0.625 | 8 |
| Comparative Example 6 | Compound H22 |  | 1 | 5.31 | 5.8 | 0.327 | 0.62 | 5 |
| Comparative Example 7 | Compound H46 |  | 1 | 5.89 | 7.2 | 0.324 | 0.621 | 5 |
| Comparative Example 8 |  | Compound E6 | 1 | 3.8 | 27.6 | 0.322 | 0.622 | 18 |
| Comparative Example 9 |  | Compound E12 | 1 | 3.83 | 30.2 | 0.323 | 0.626 | 15 |
| Comparative Example 10 |  | Compound E23 | 1 | 3.75 | 28.9 | 0.324 | 0.628 | 21 |
| Comparative Example 11 |  | Compound E26 | 1 | 3.69 | 27.6 | 0.324 | 0.629 | 19 |
| Comparative Example 12 |  | Compound E72 | 1 | 3.84 | 27.4 | 0.331 | 0.623 | 25 |
| Comparative Example 13 |  | Compound E76 | 1 | 3.86 | 27 | 0.329 | 0.621 | 23 |

As can be seen from the results in Table 1, the organic light emitting devices of Examples 1-14 had low driving voltages, luminous efficiencies and, particularly, considerably improved life characteristics compared to the organic light emitting devices of Comparative Examples 1-13. These results demonstrate that the organic light emitting devices of Examples 1-14 are expected to be useful in a variety of industrial applications, including displays and lighting systems.

What is claimed is:

1. An organic light emitting device comprising a first electrode, a second electrode opposite to the first electrode, and at least one organic layer interposed between the first and second electrodes wherein the organic layer comprises a first compound represented by Formula A:

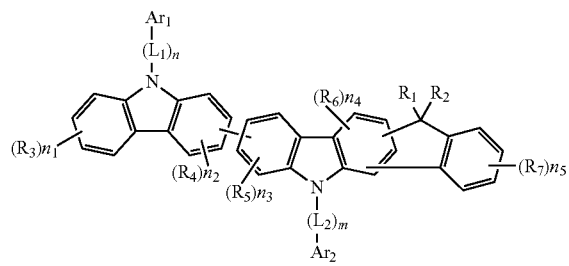

(A)

wherein $L_1$ and $L_2$ are identical to or different from each other and are each independently a single bond or a linker selected from substituted or unsubstituted $C_1$-$C_{60}$ alkylene groups, substituted or unsubstituted $C_2$-$C_{60}$ alkenylene groups, substituted or unsubstituted $C_2$-$C_{60}$ alkynylene groups, substituted or unsubstituted $C_3$-$C_{60}$ cycloalkylene groups, substituted or unsubstituted $C_2$-$C_{60}$ heterocycloalkylene groups, substituted or unsubstituted $C_6$-$C_{60}$ arylene groups, and substituted or unsubstituted $C_2$-$C_{60}$ heteroarylene groups, n and m are each independently an integer from 0 to 3, $Ar_1$ and $Ar_2$ and $R_1$ to $R_7$ are identical to or different from each other and are each independently selected from hydrogen, deuterium, substituted or unsubstituted $C_1$-$C_{30}$ alkyl groups, substituted or unsubstituted $C_2$-$C_{30}$ alkenyl groups, substituted or unsubstituted $C_3$-$C_{30}$ cycloalkyl groups, substituted or unsubstituted $C_5$-$C_{30}$ cycloalkenyl groups, substituted or unsubstituted $C_1$-$C_{30}$ alkoxy groups, substituted or unsubstituted $C_6$-$C_{30}$ aryloxy groups, substituted or unsubstituted $C_1$-$C_{30}$ alkylthioxy groups, substituted or unsubstituted $C_5$-$C_{30}$ arylthioxy groups, substituted or unsubstituted $C_1$-$C_{30}$ alkylamine groups, substituted or unsubstituted $C_5$-$C_{30}$ arylamine groups, substituted or unsubstituted $C_6$-$C_{50}$ aryl groups, substituted or unsubstituted $C_3$-$C_{50}$ heteroaryl groups containing O, N or S as a heteroatom, substituted or unsubstituted silyl groups, substituted or unsubstituted germanium groups, substituted or unsubstituted boron groups, substituted or unsubstituted aluminum groups, a carbonyl group, a phosphoryl group, an amino group, a nitrile group, a hydroxyl group, a nitro group, halogen groups, a selenium group, a tellurium group, an amide group, and an ester group, with the proviso that each of $Ar_1$ and $Ar_2$ and $R_1$ to $R_7$ optionally forms an aliphatic, aromatic, heteroaliphatic or heteroaromatic fused ring with the adjacent group, and n1 to n5 are each independently an integer from 0 to 4, and a second compound selected from Compounds E9 to E23, and E25 to E28, and E30 to E44, and E46 to E132:

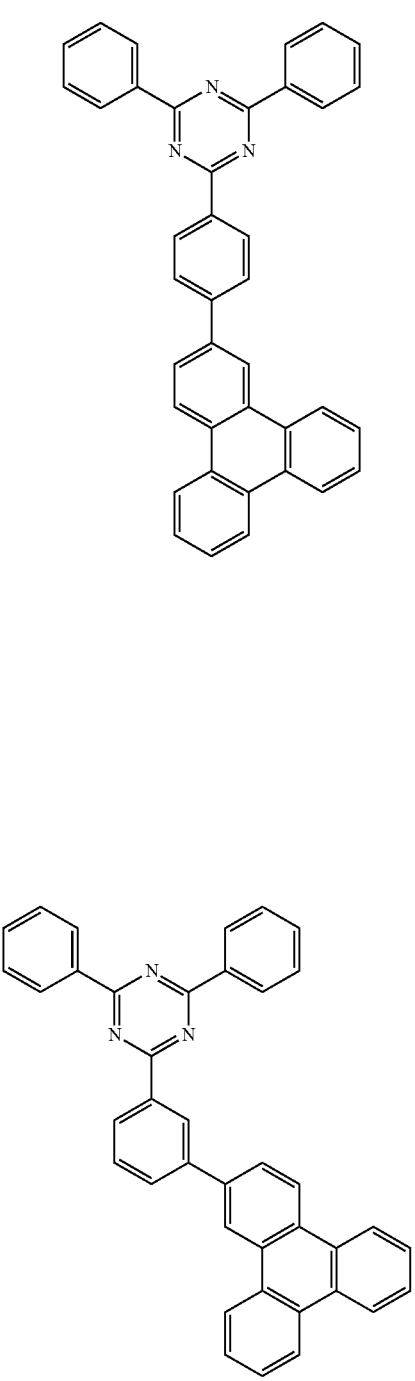

Compound E9

Compound E10

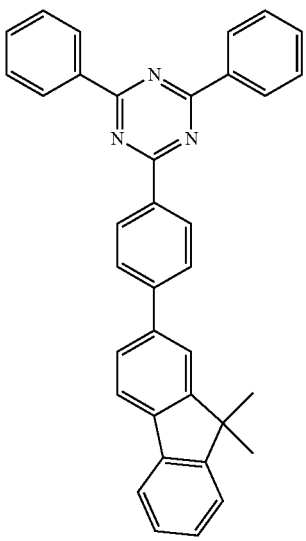

Compound E11

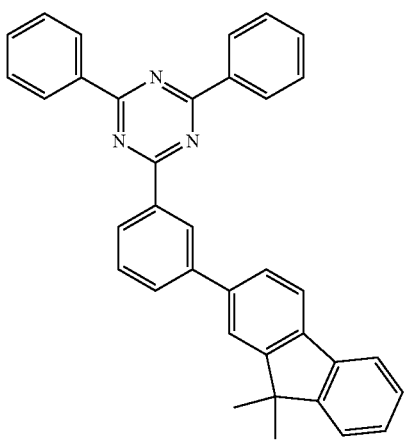

Compound E12

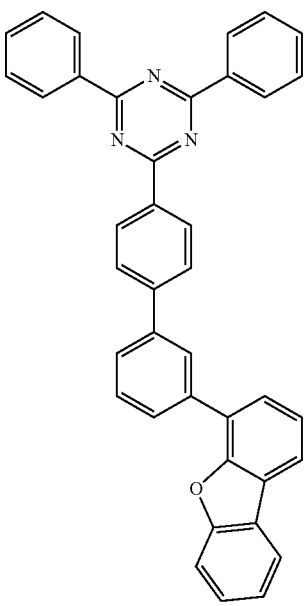

Comound E13

-continued
Compound E14
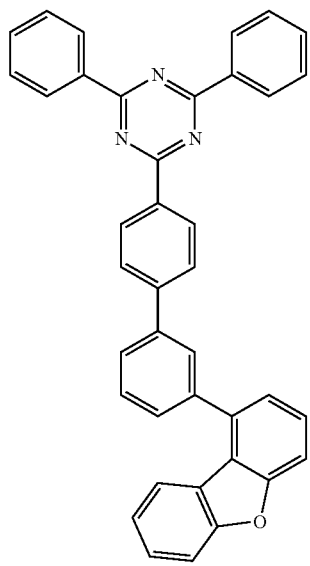
Compound E15
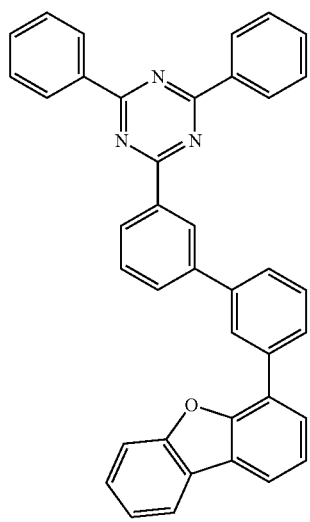
Compound E16
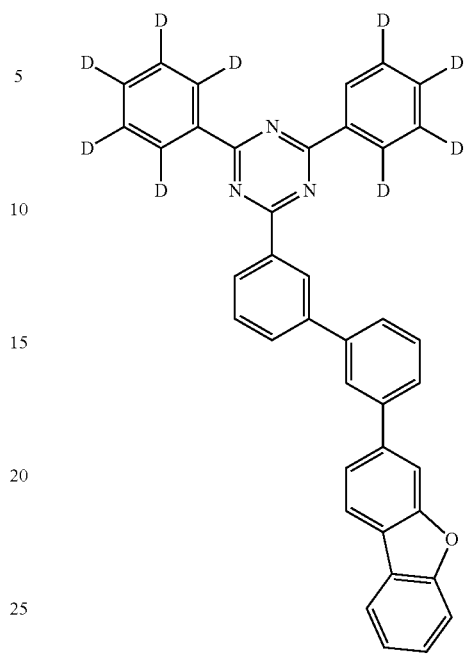
Compound E17
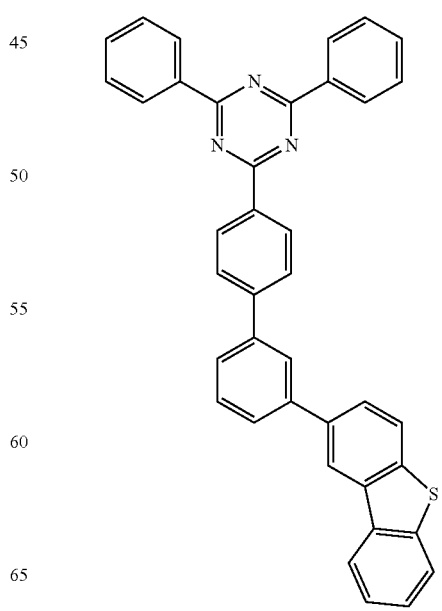

-continued
Compound E18
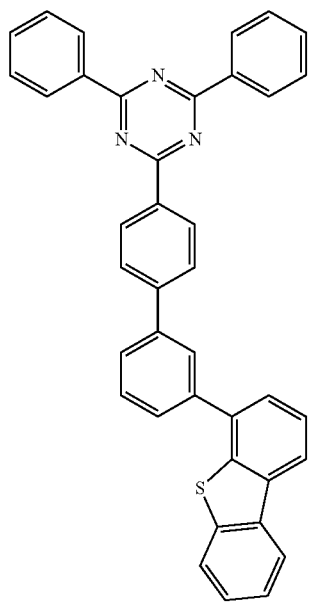
Compound E19
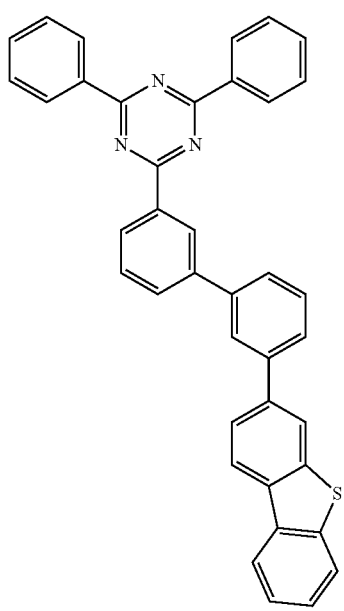
Compound E20
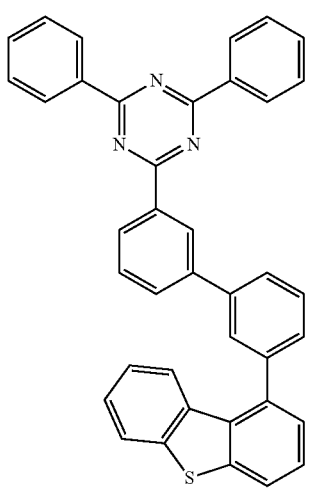
Compound E21
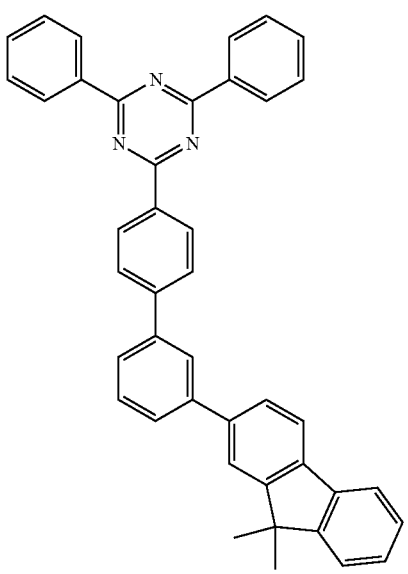
Compound E22
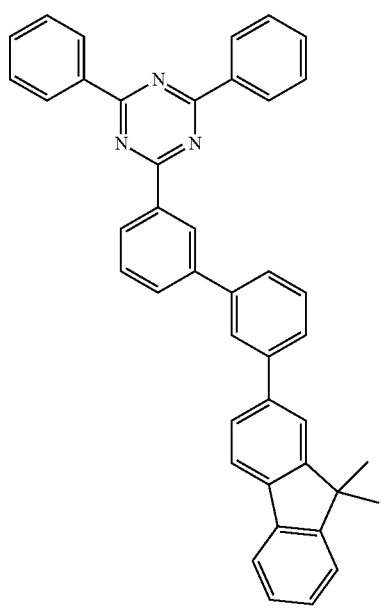

Compound E23
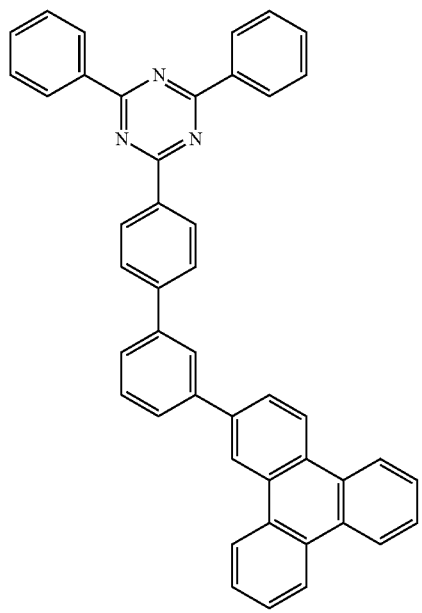
Compound E26
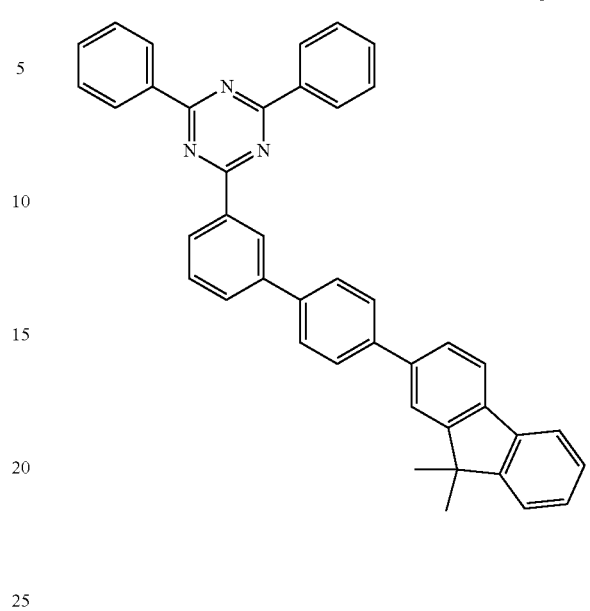
Compound E25
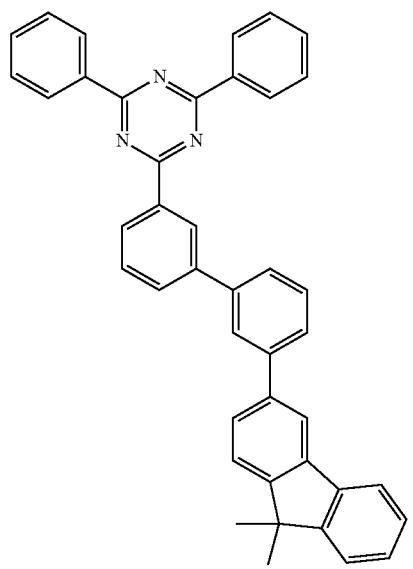

-continued
Compound E28
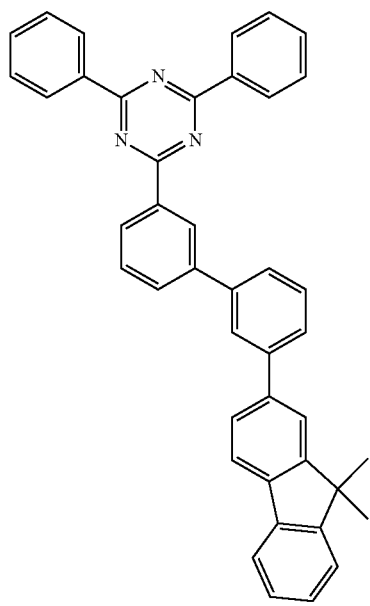
Compound E30
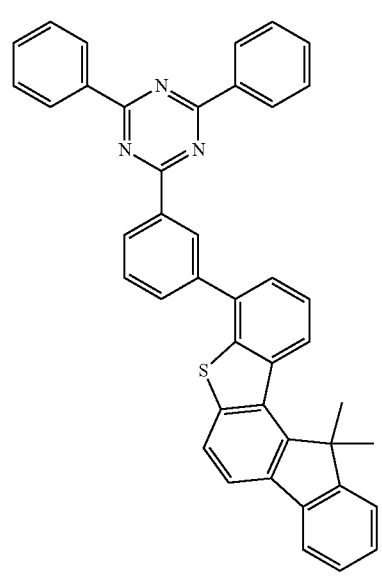
Compound E31
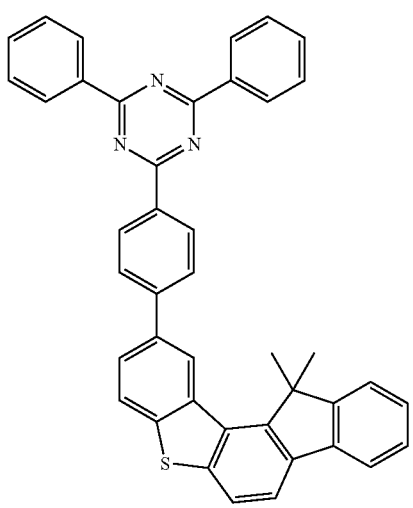
Compound E29
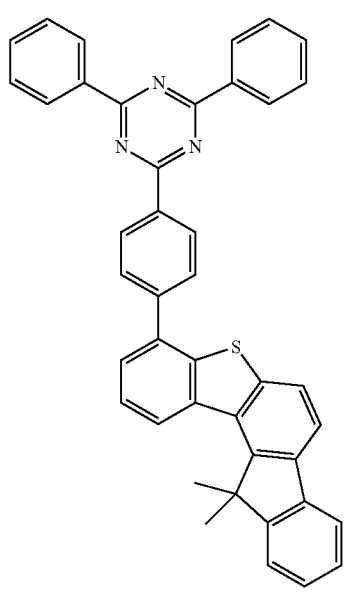
Compound E32
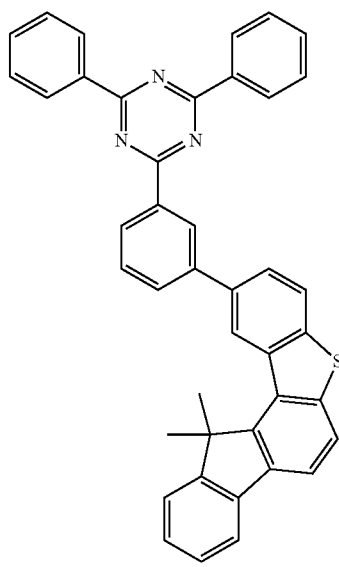

Compound E33
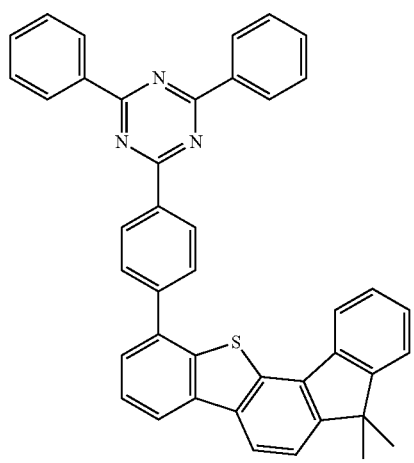
Compound E34
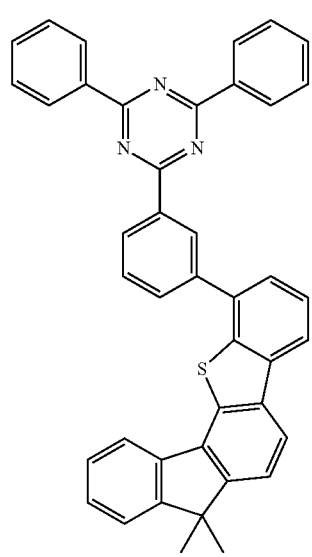
Compound E35
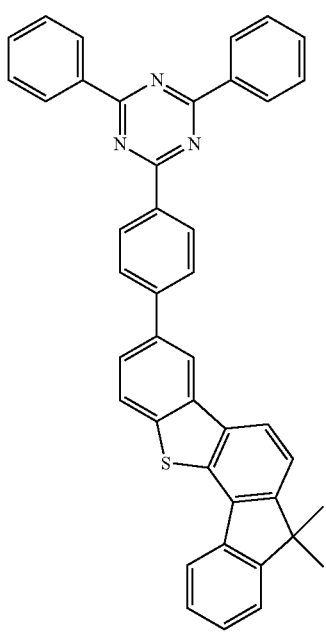
Compound E36
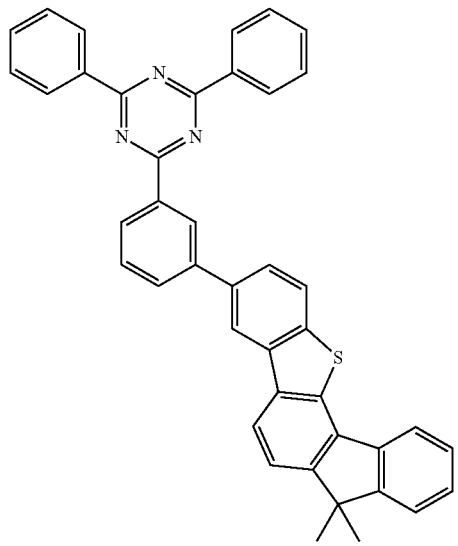
Compound E37
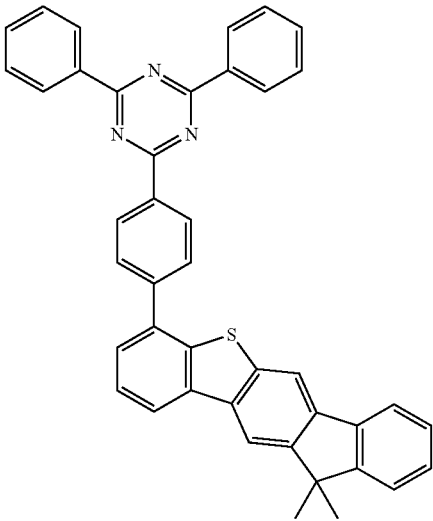

Compound E38
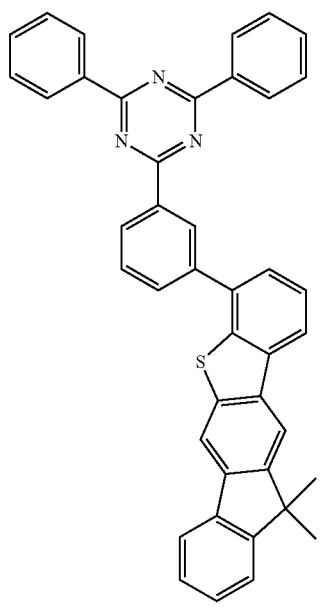
Compound E40
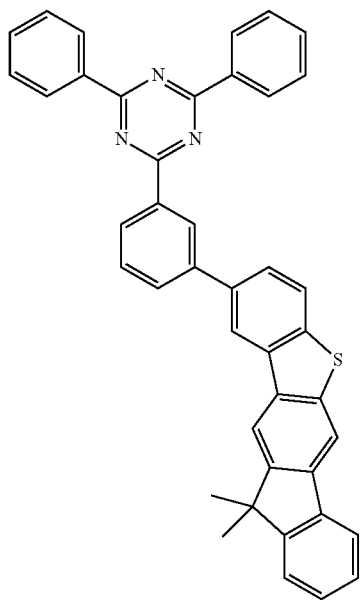
Compound E39
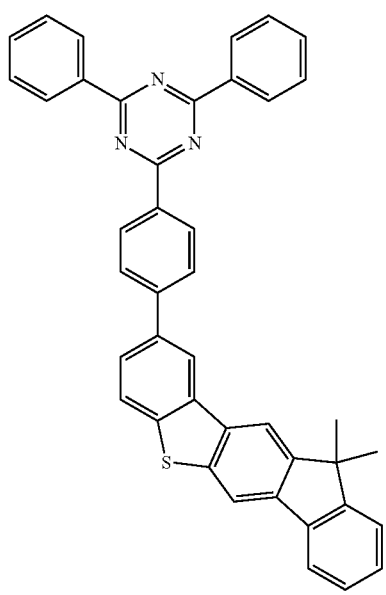
Compound E41
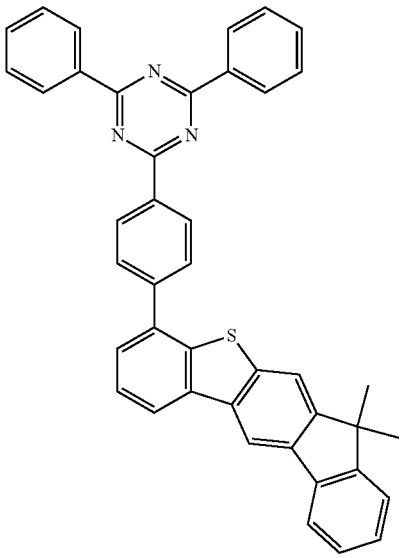

Compound E42
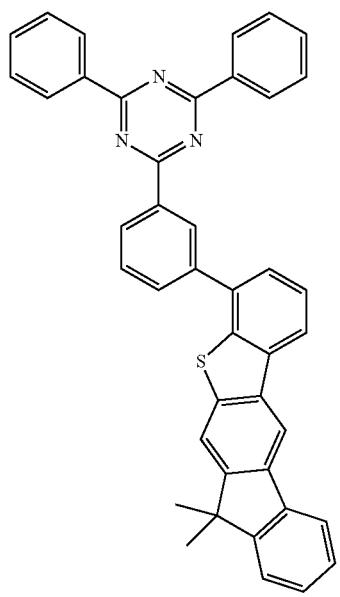
Compound E44
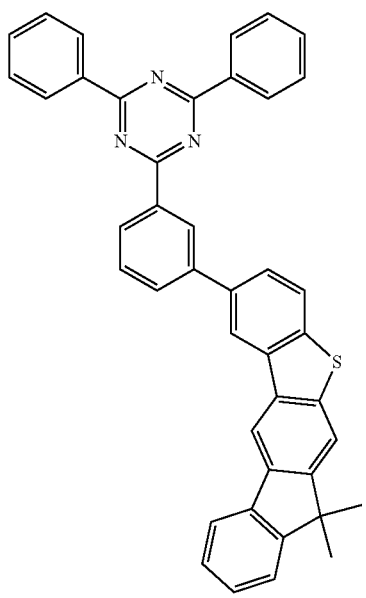
Compound E43
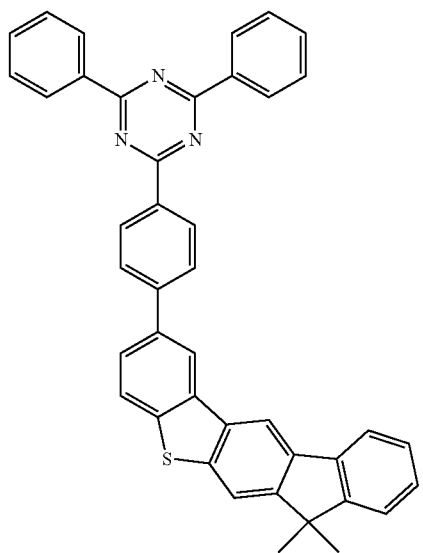
Compound E46
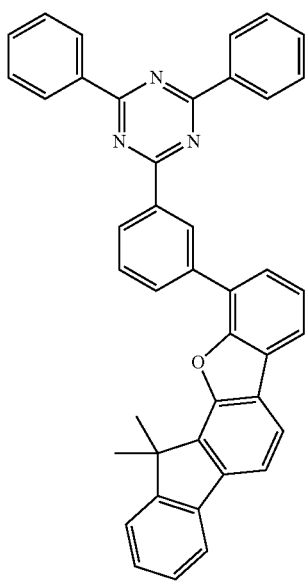

Compound E47
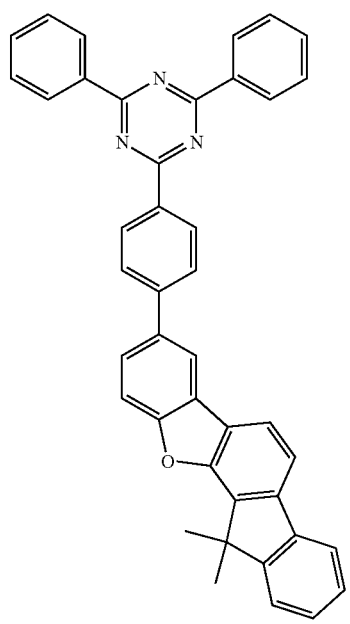
Compound E48
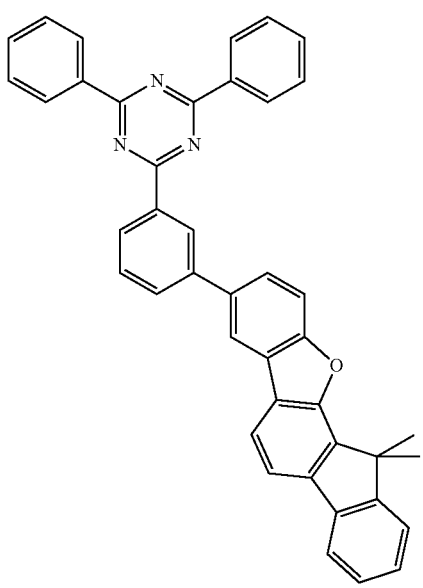
Compound E49
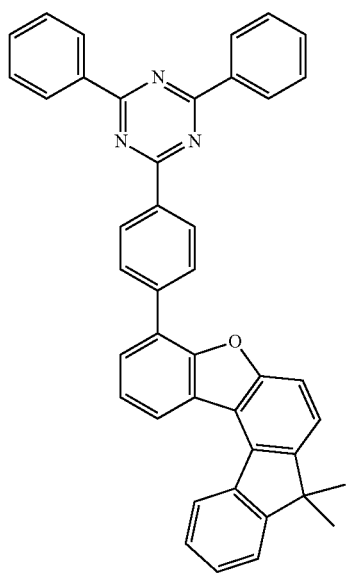
Compound E50
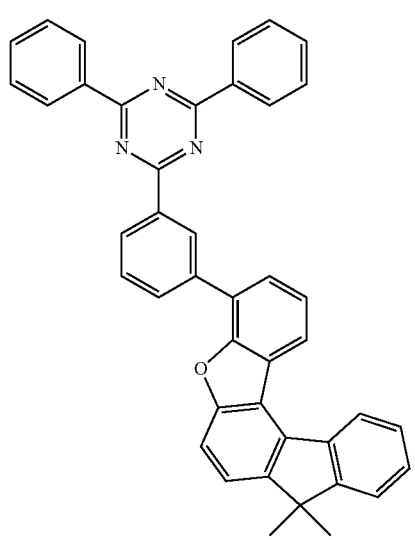
Compound E51
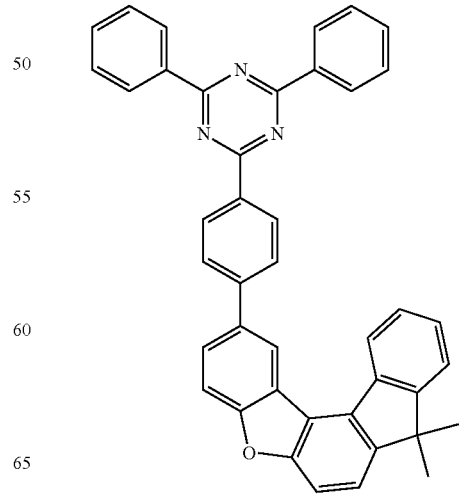

Comopund E52
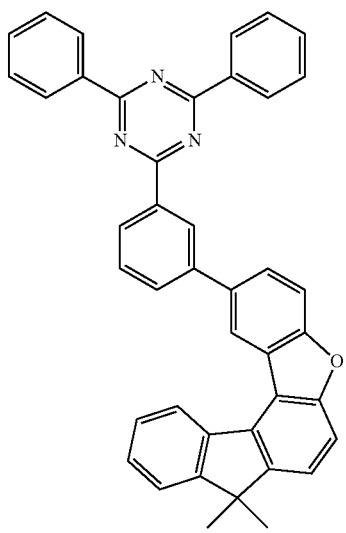
Compound E54
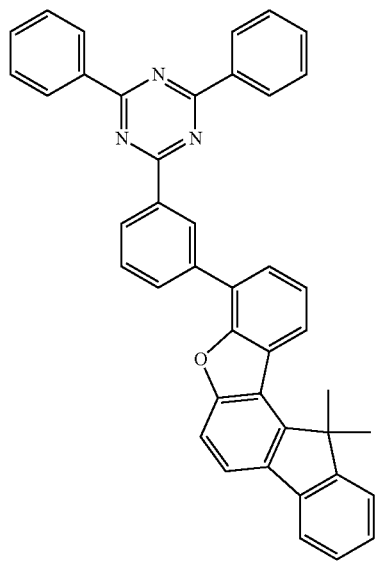
Compound E55
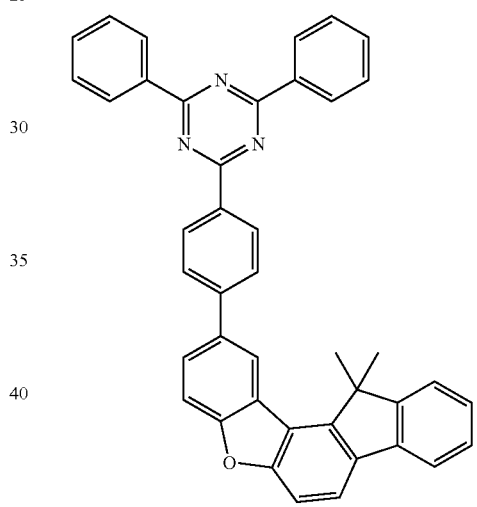
Compound E53
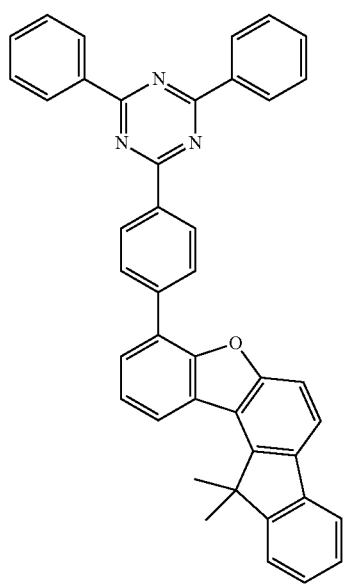
Compound E56
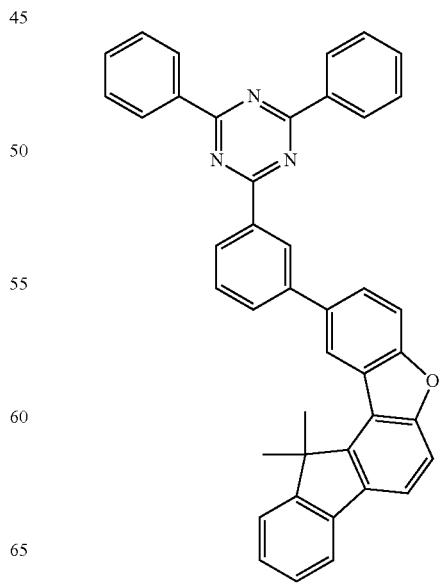

Compound E57
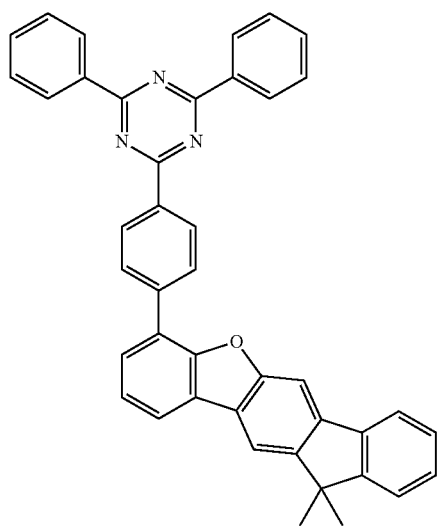
Compound E58
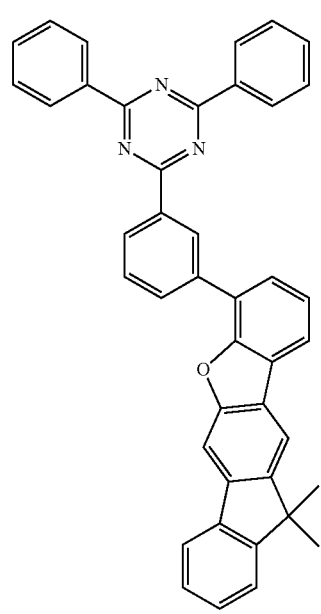
Compound E59
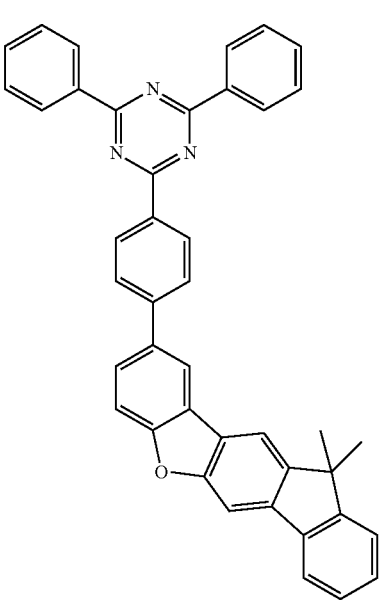
Compound E60
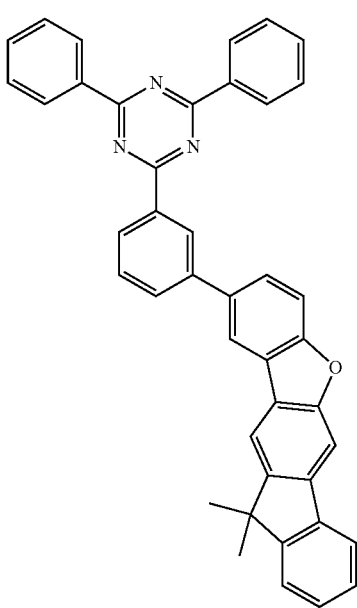

Compound E61
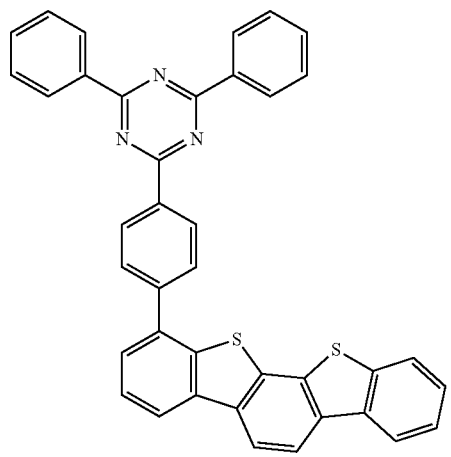
Compound E62
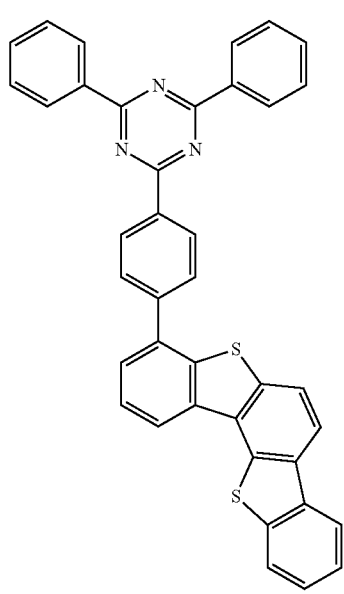
Compound E63
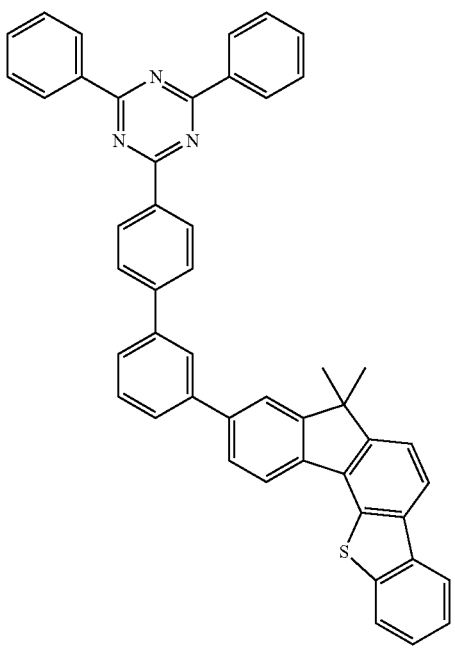
Compound E64
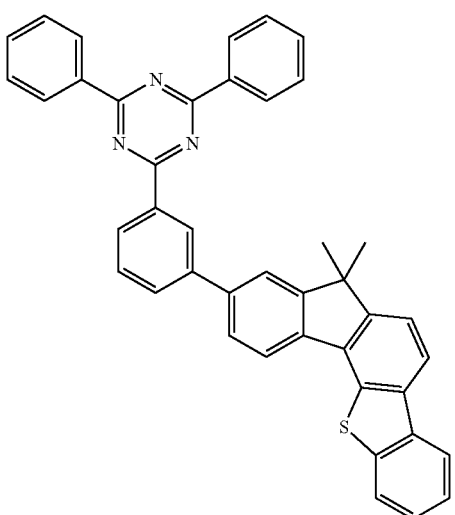
Compound E65

Compound E66
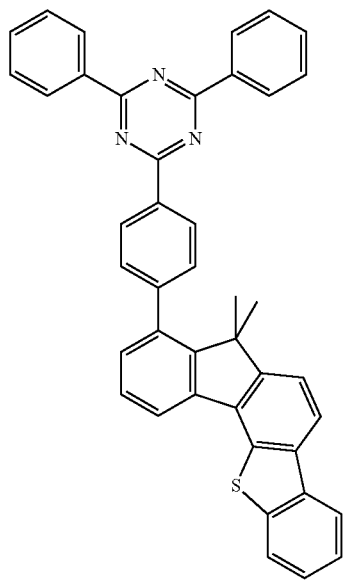
Compound E67
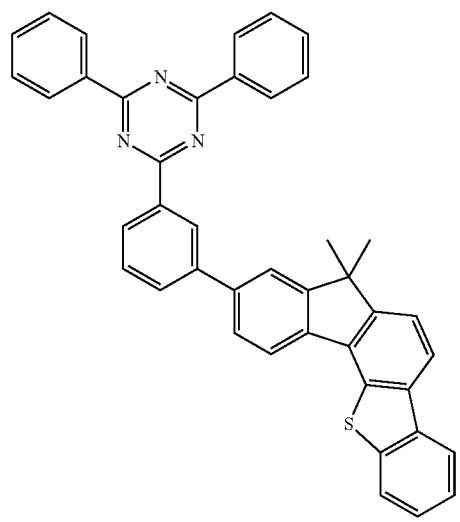
Compound E68
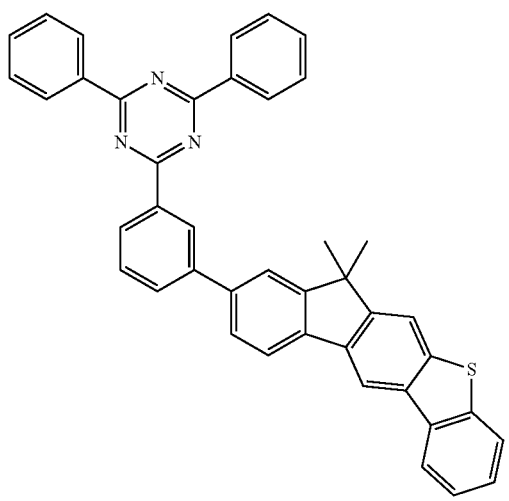
Compound E69
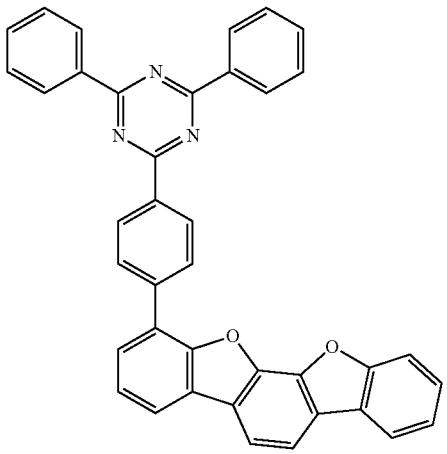
Compound E70
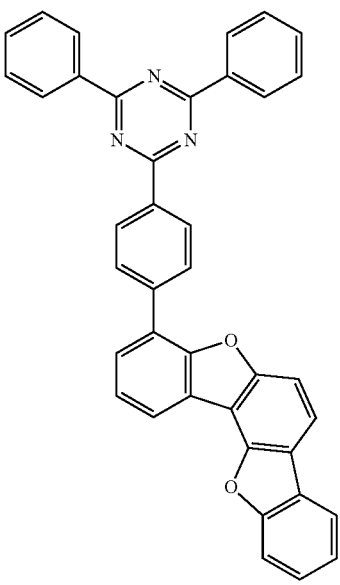

Compound E71
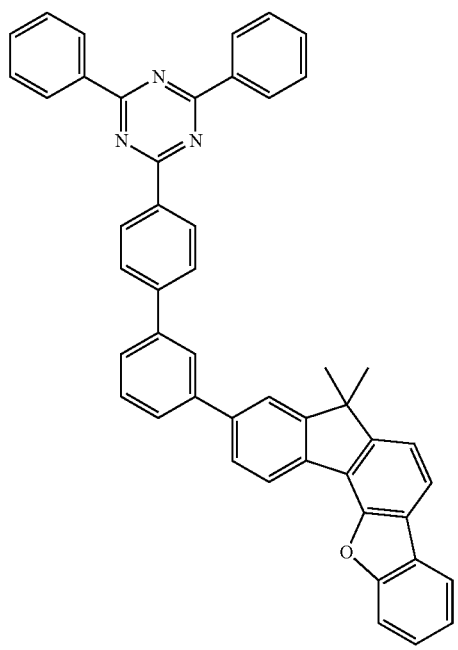
Compound E72
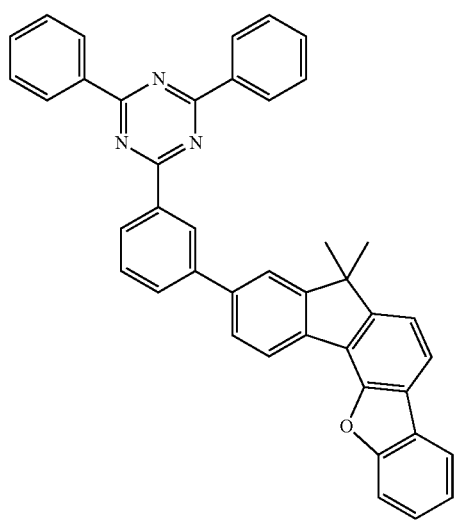
Compound E73
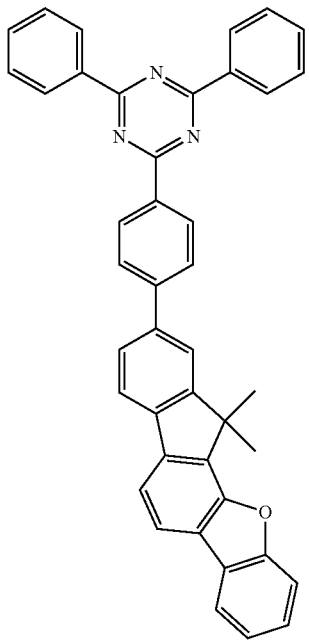
Compound E74
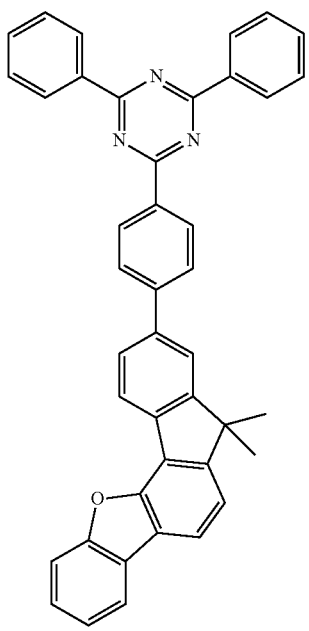

Compound E75
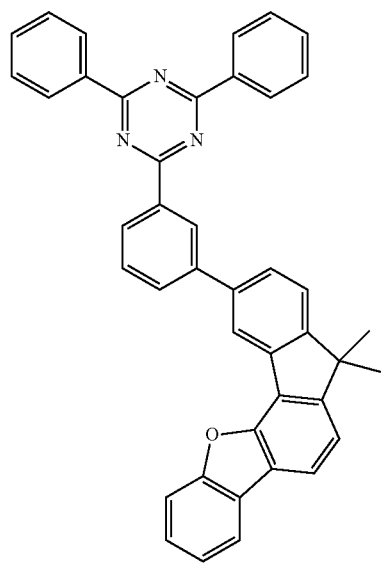
Compound E77
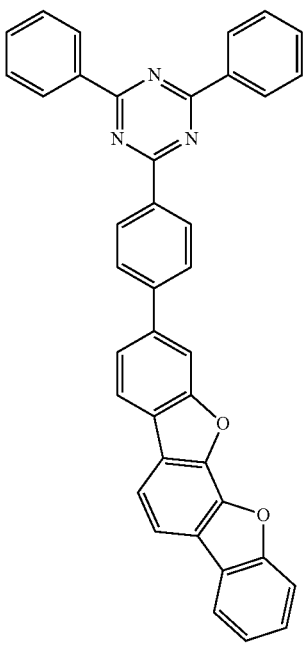
Compound E76
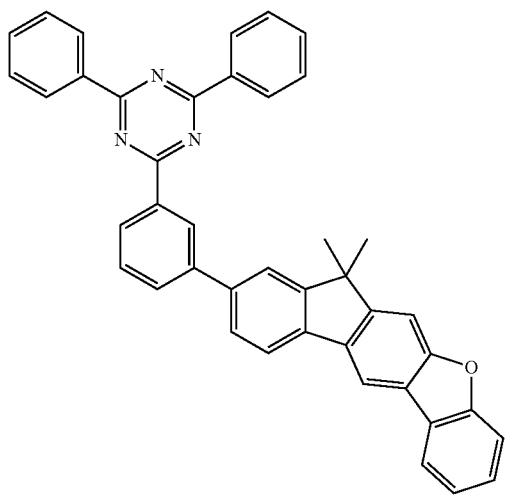
Compound E78
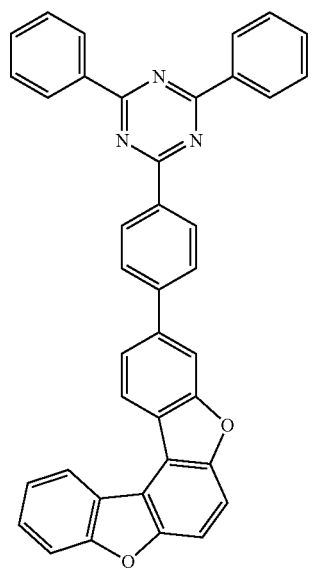

Compound E79
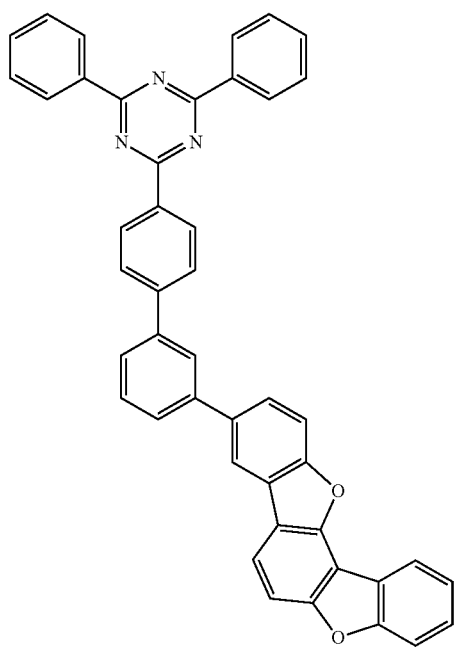
Compound E80
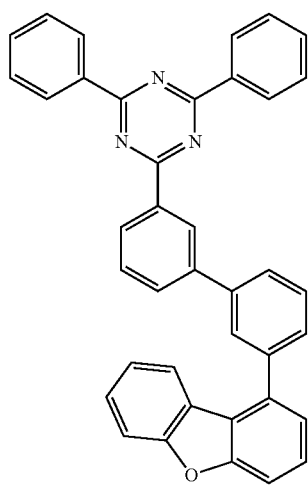
Compound E81
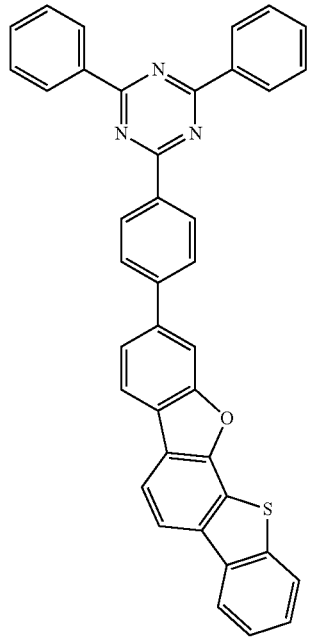
Compound E82
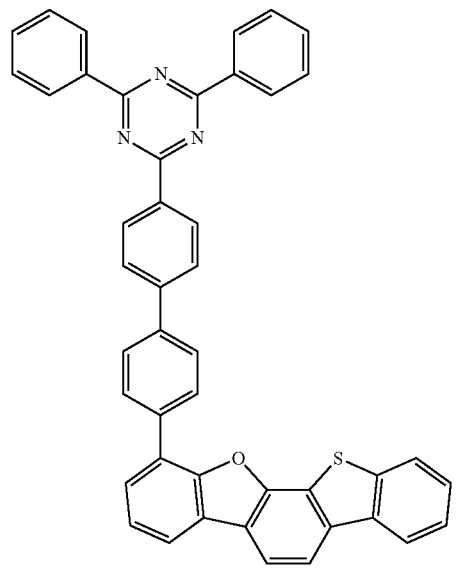

Compound E83
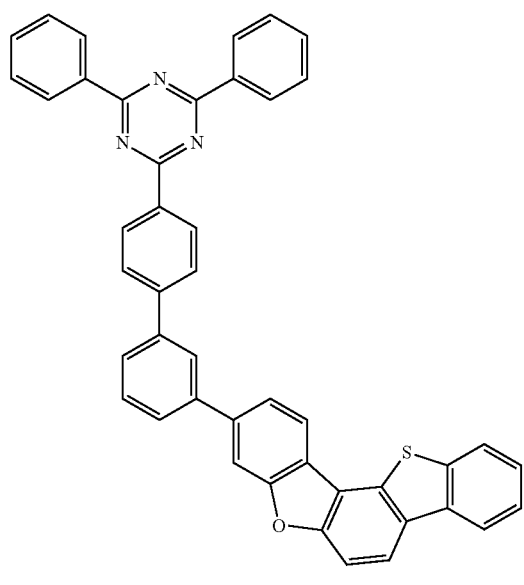
Compound E85
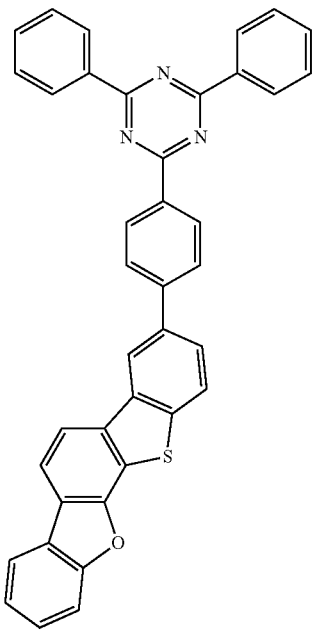
Compound E84
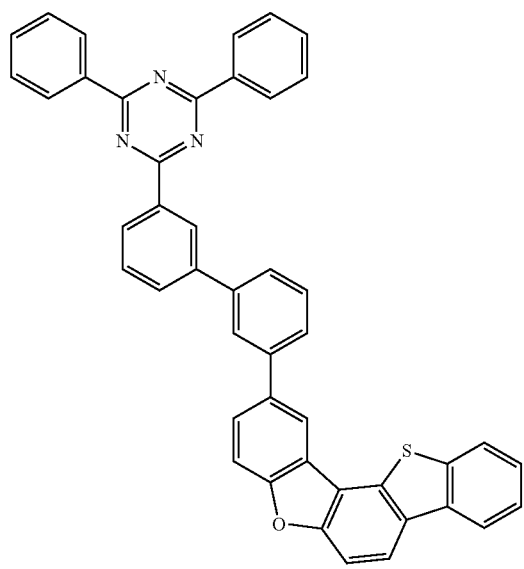
Compound E86
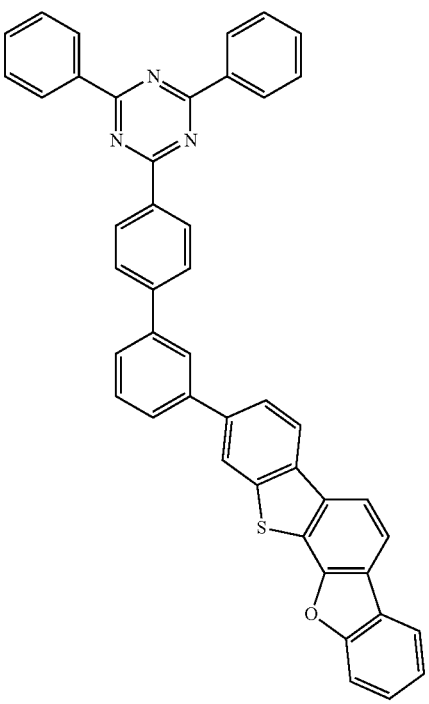

Compound E87
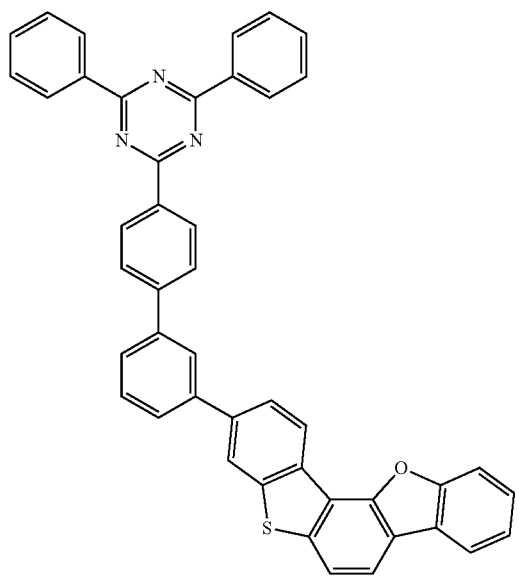
Compound E88
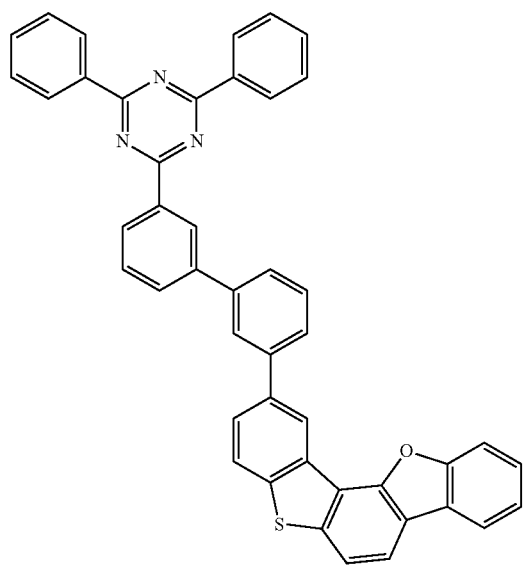
Compound E89
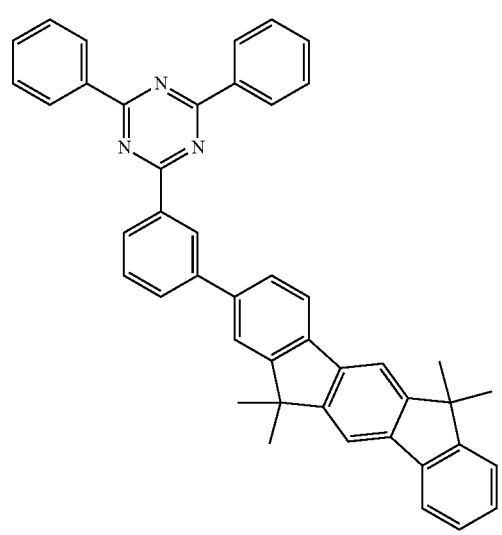
Compound E90
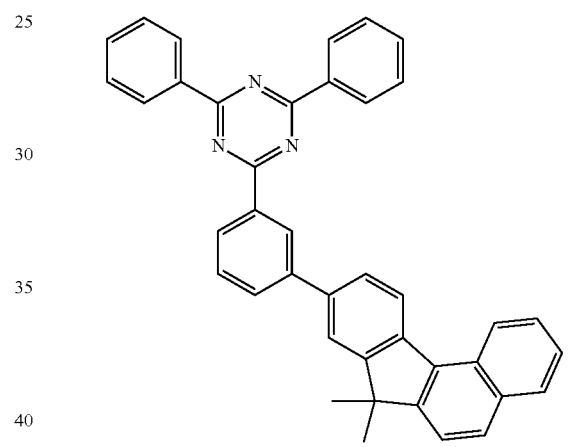
Compound E91
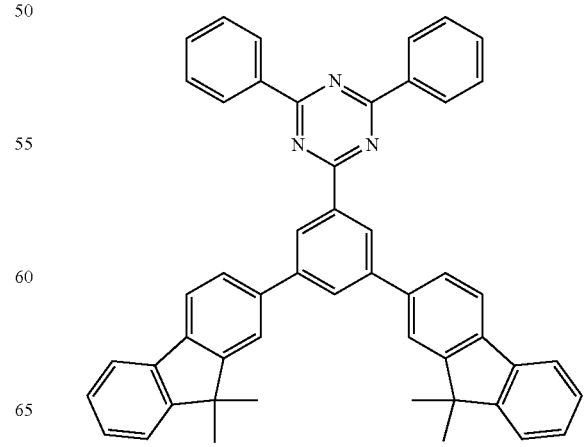

Compound E92
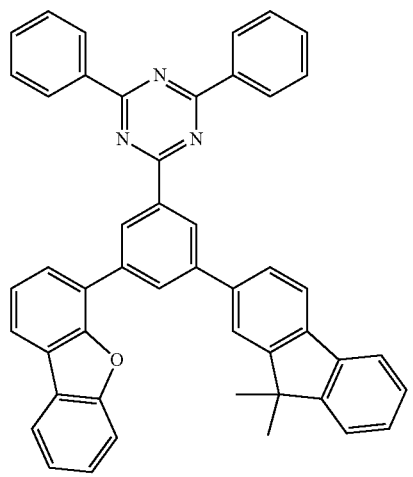
Compound E93
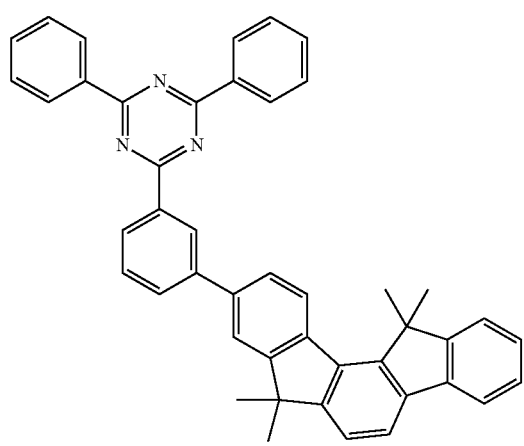
Comopund E94
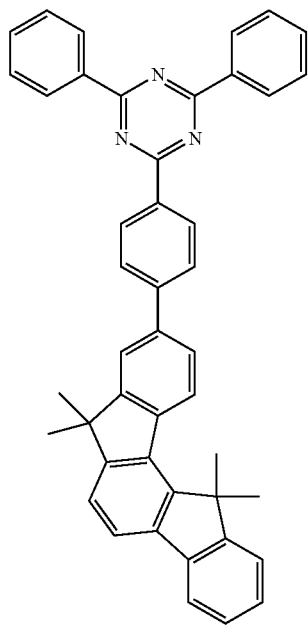
Compound E95
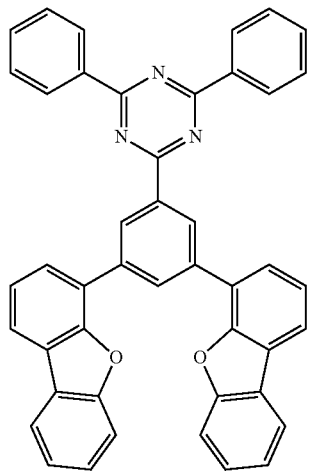
Compound E96
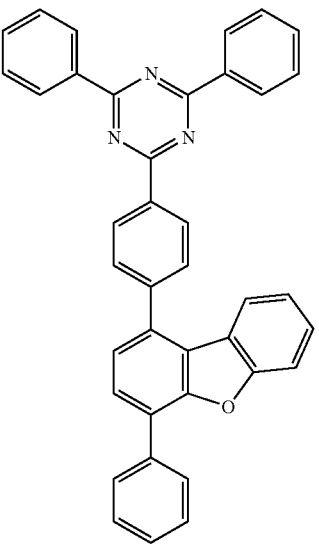
Compound E97
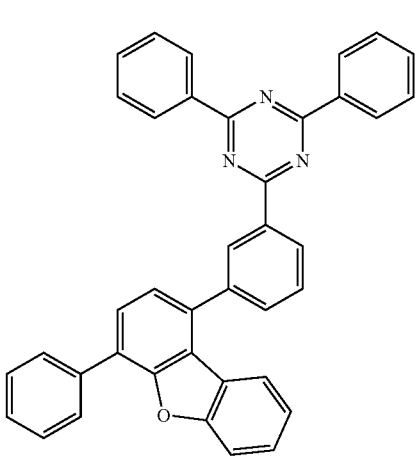

Compound E98
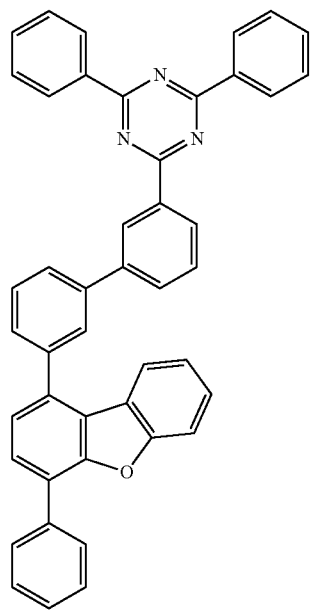
Compound E99
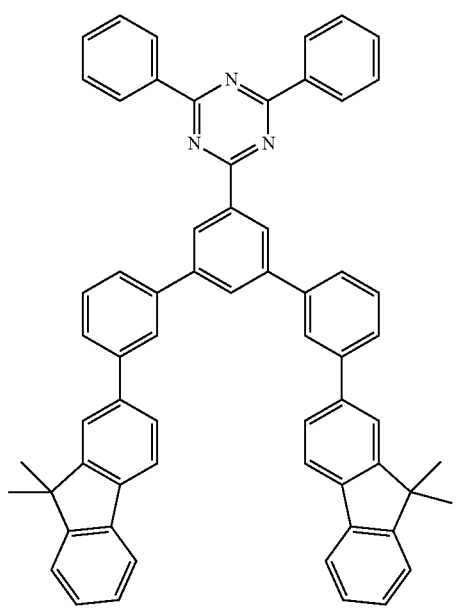
Compound E100
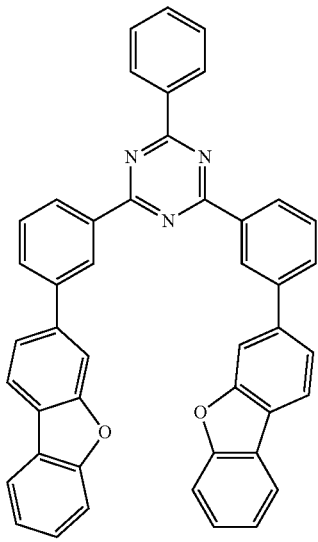
Compound E101
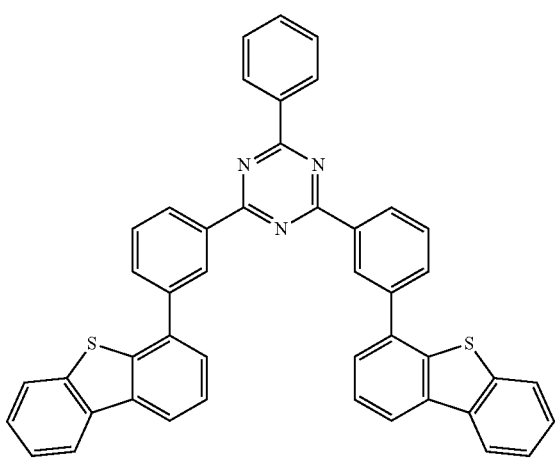
Compound E102
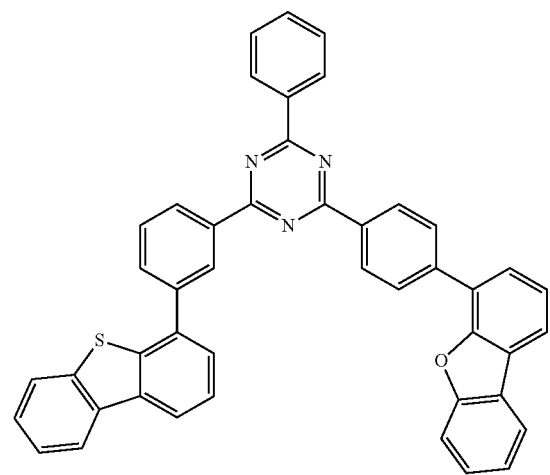

Compound E103
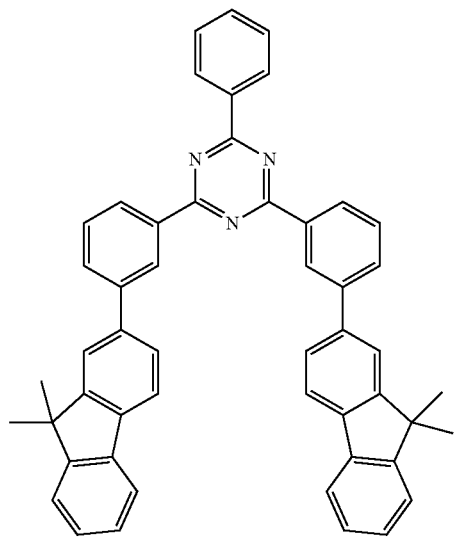
Compound E104
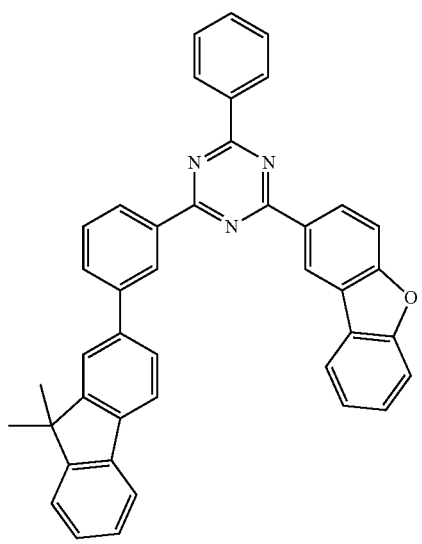
Compound E105
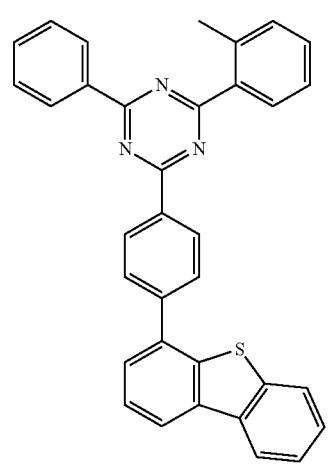
Compound E106
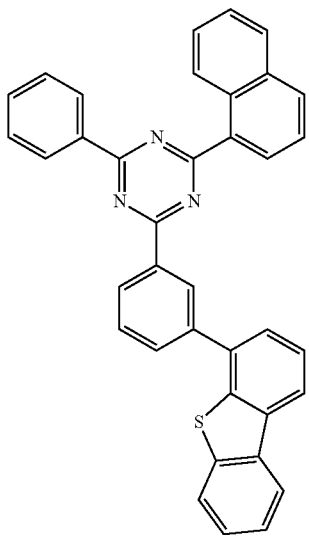
Compound E107

Compound E108
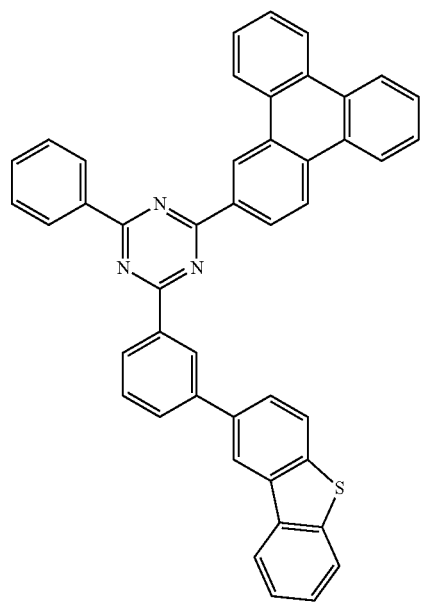
Compound E110
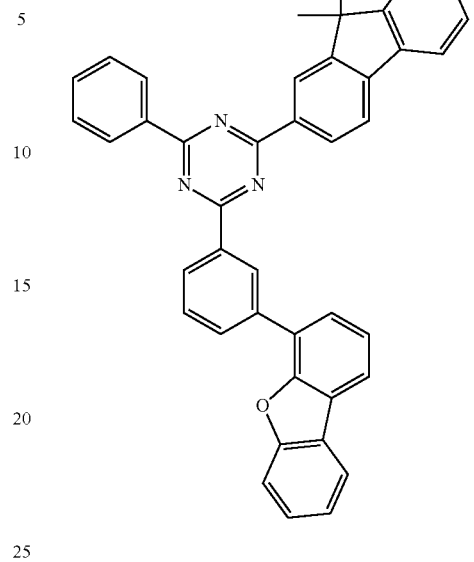
Compound E109
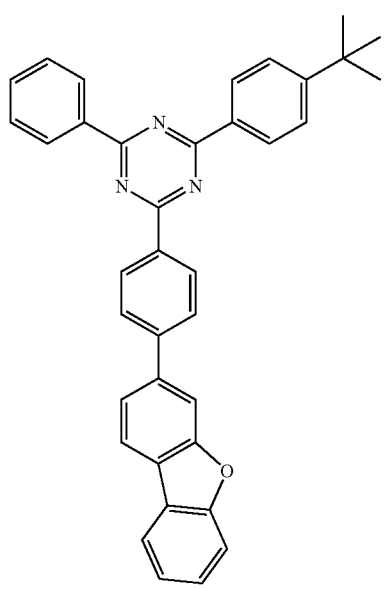
Compound E111
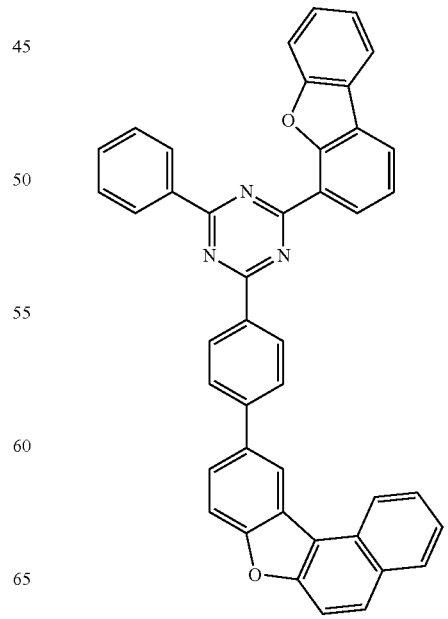

Compound E112
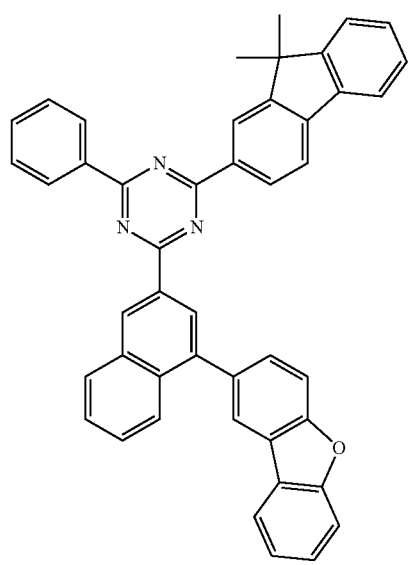
Compound E113
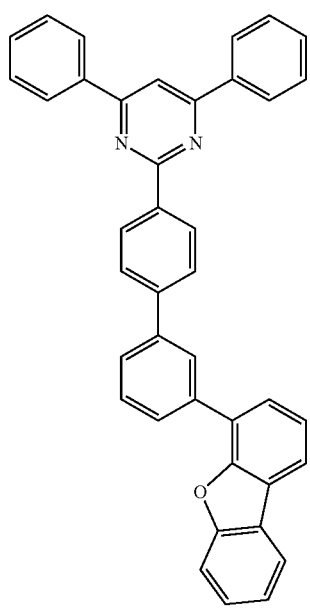
Compound E114
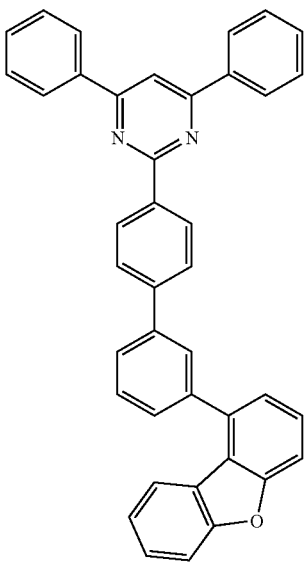
Compound E115
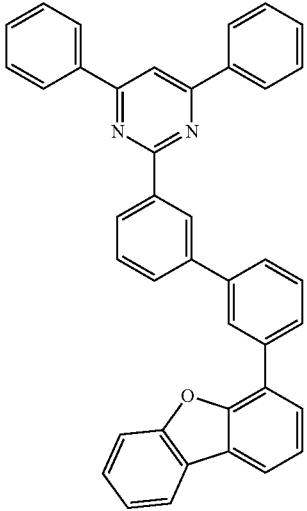

Compound E116
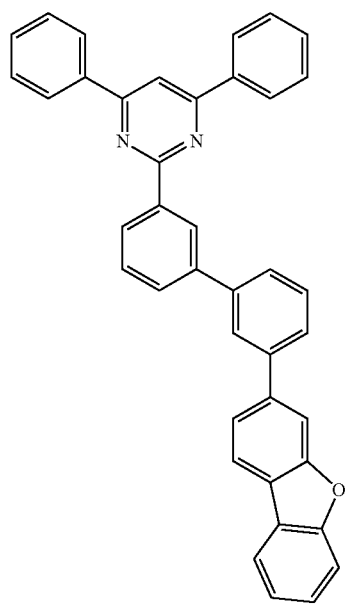
Compound E117
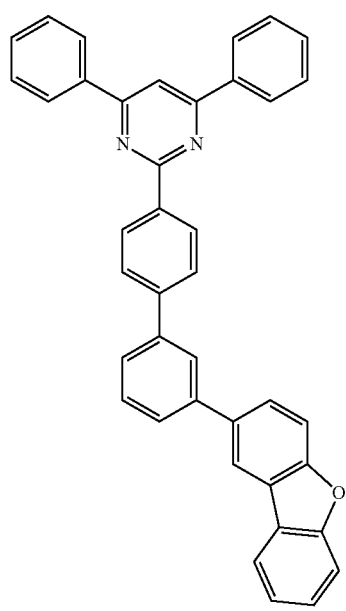
Compound E118
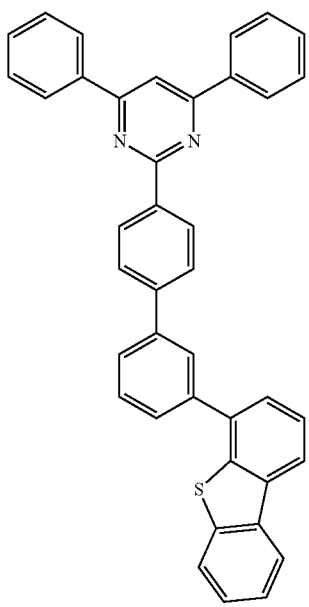
Compound E119
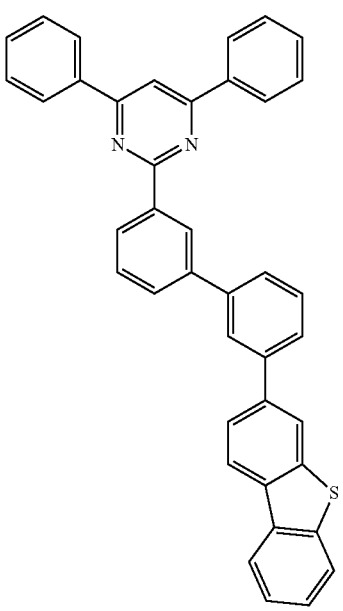

Compound E120
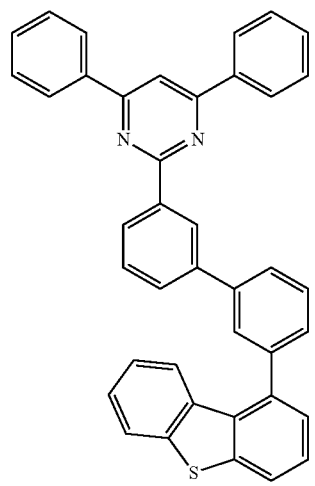
Compound E121
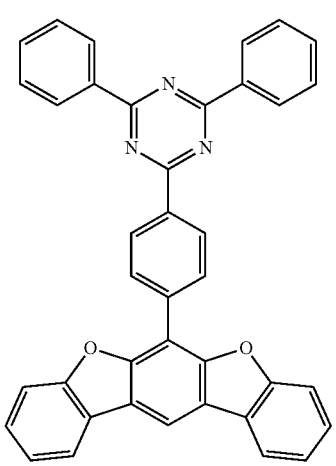
Compound E123
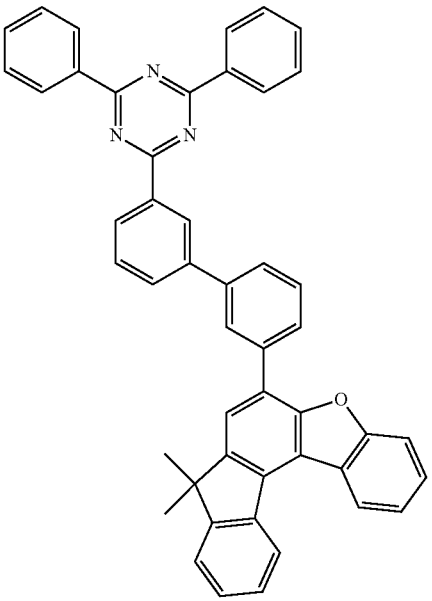
Compound E122
Compound E124
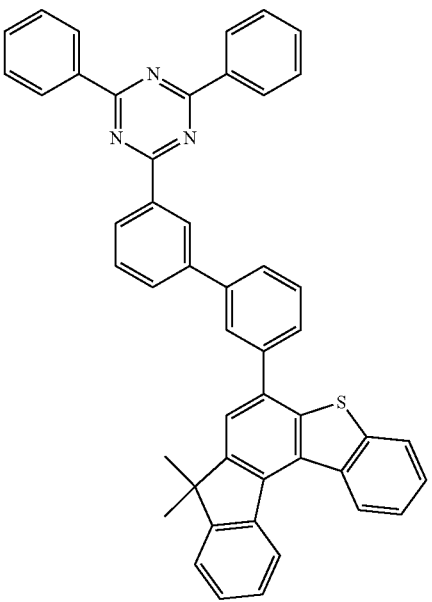

Compound E125
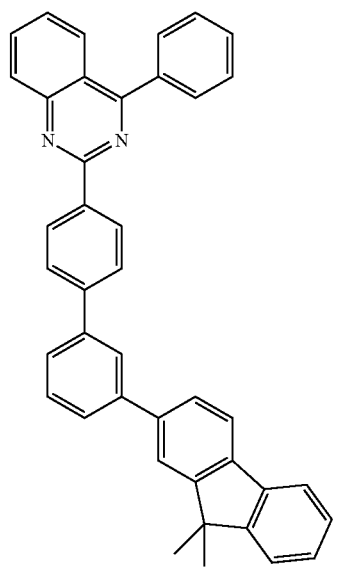
Compound E127
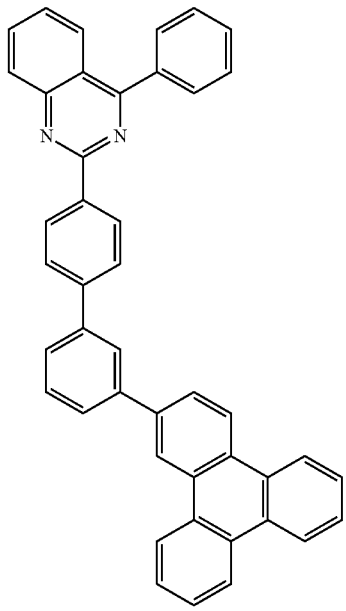
Compound E126
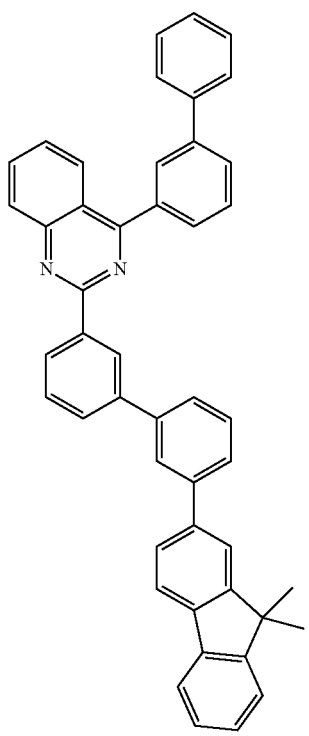
Compound E128
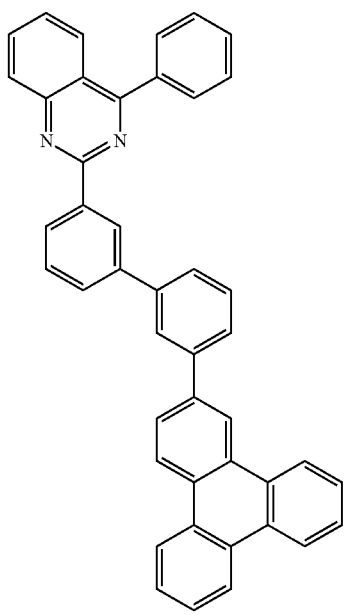

Compound E129

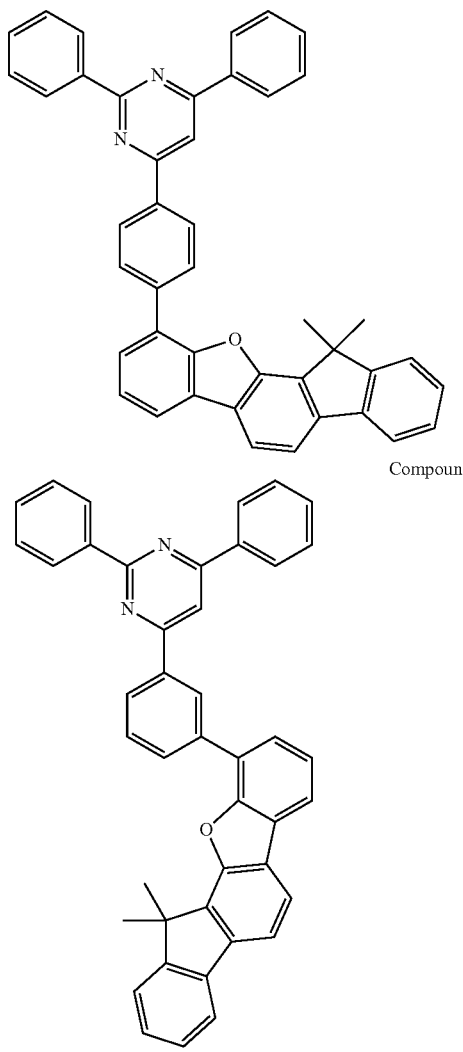

Compound E130

Compound E131

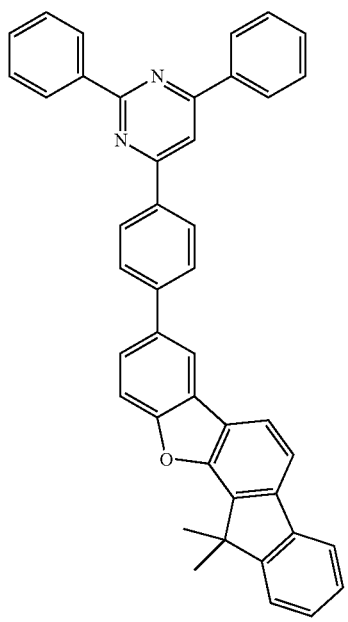

Compound E132

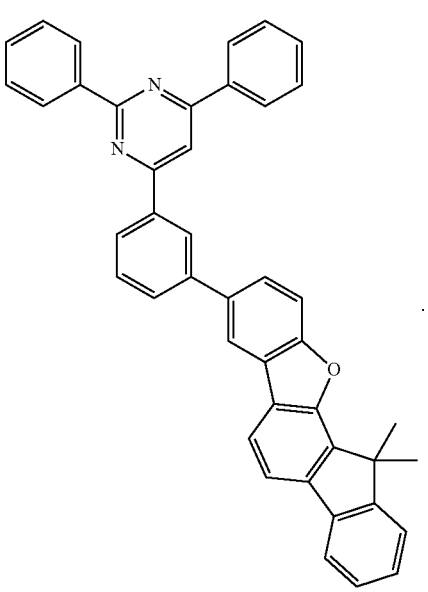

2. An organic light emitting device comprising a first electrode, a second electrode opposite to the first electrode, and at least one organic layer interposed between the first and second electrodes wherein the organic layer comprises a first compound selected from Compounds H3 to H5, H7, H13, H19, H23, H24, H26, H27, H33, H41, H45, H46, H48, H50 to H52, and H55 to H60:

Comound H3

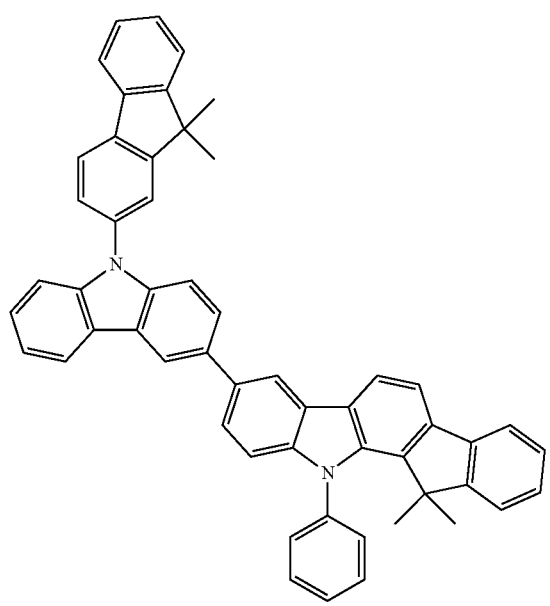

Compound H4
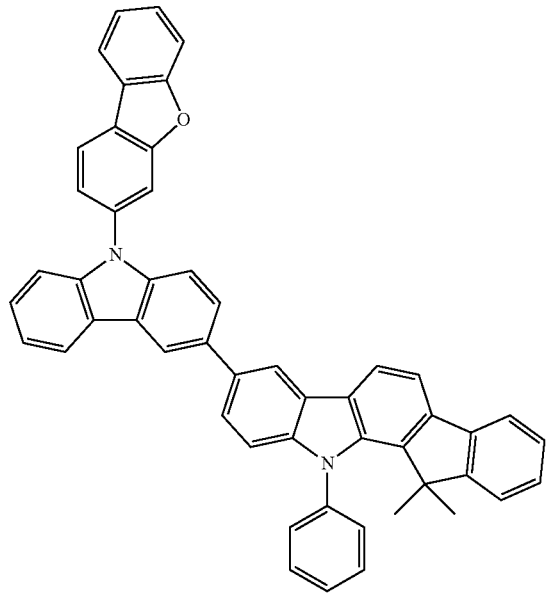
Compound H5
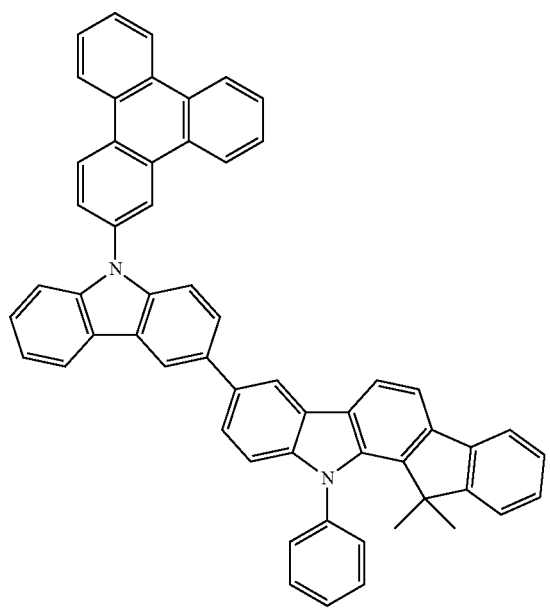
Compound H7
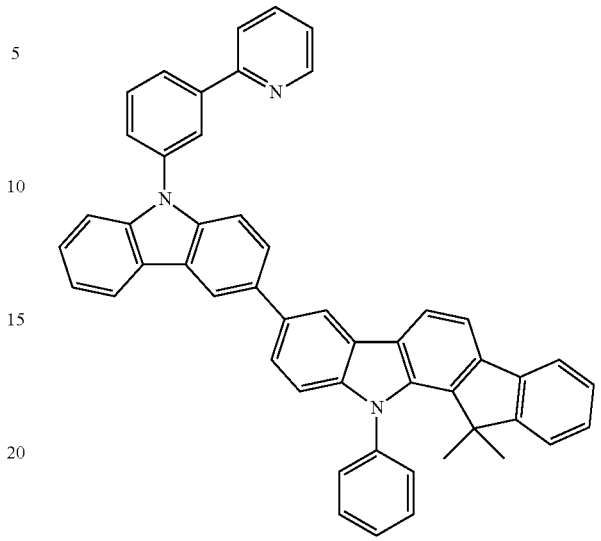
Compound H13
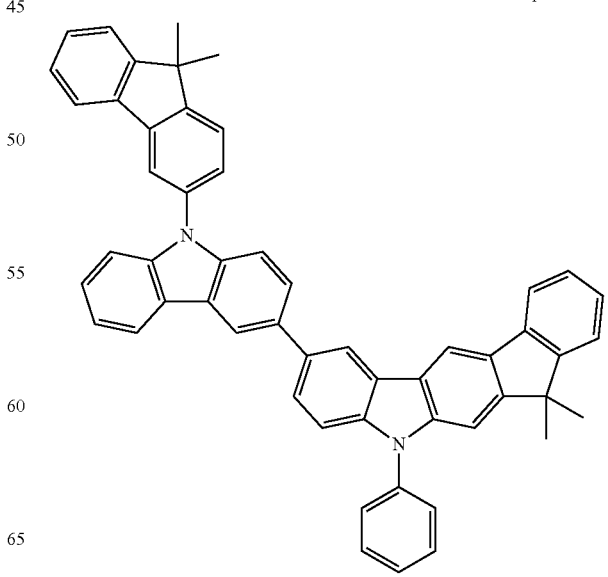
Compound H19

Compound H23
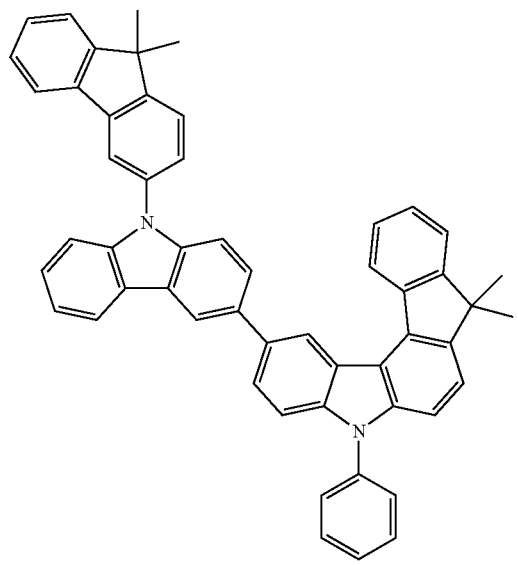
Compound H24
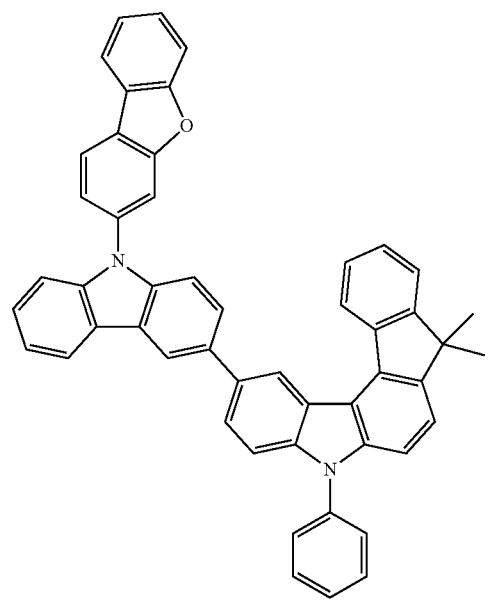
Compound H26
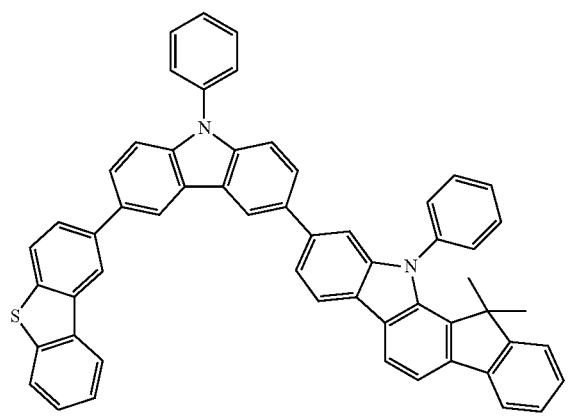
Compound H27
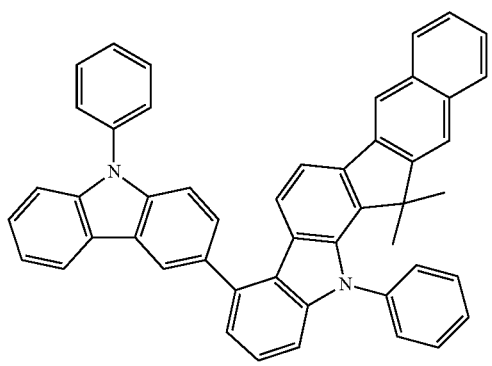
Compound 33
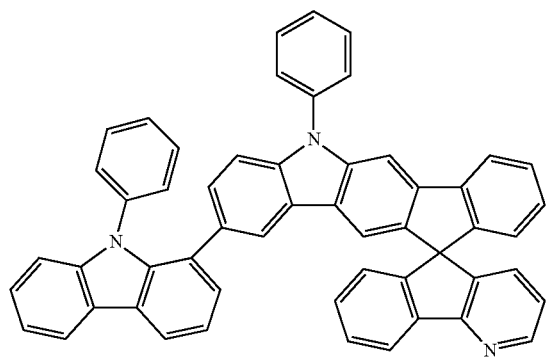
Compound H41
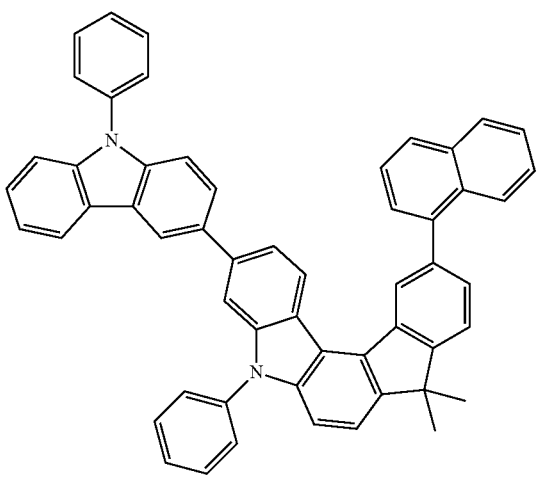

Compound H45
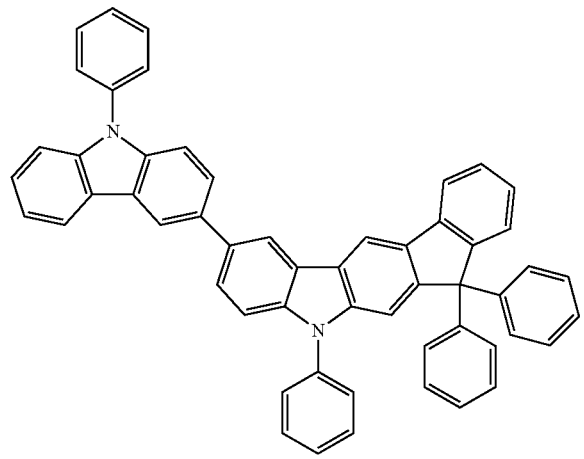
Compound H50
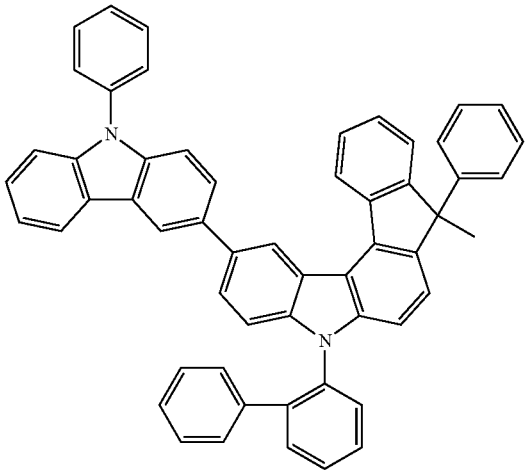
Compound H46
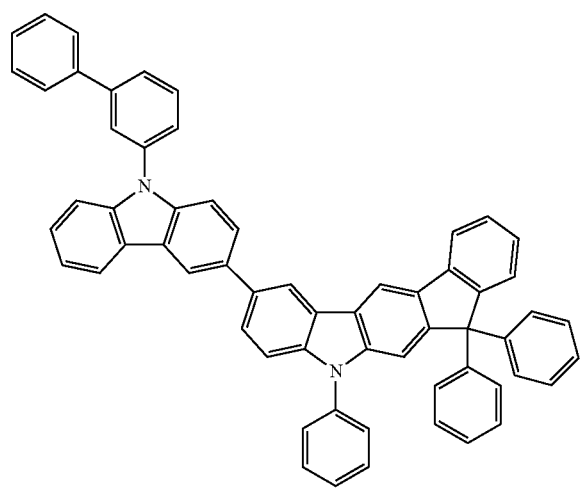
Compound H51
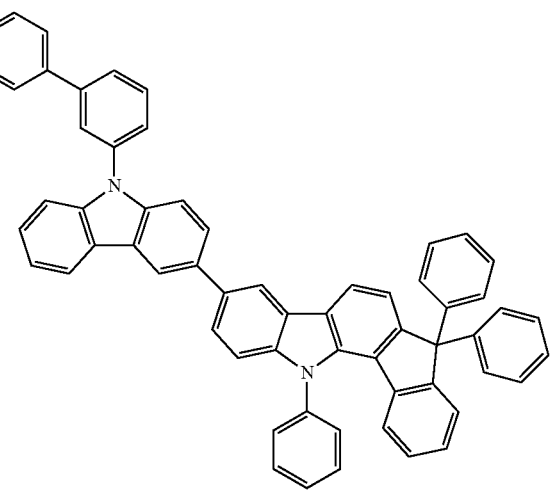
Compound H48
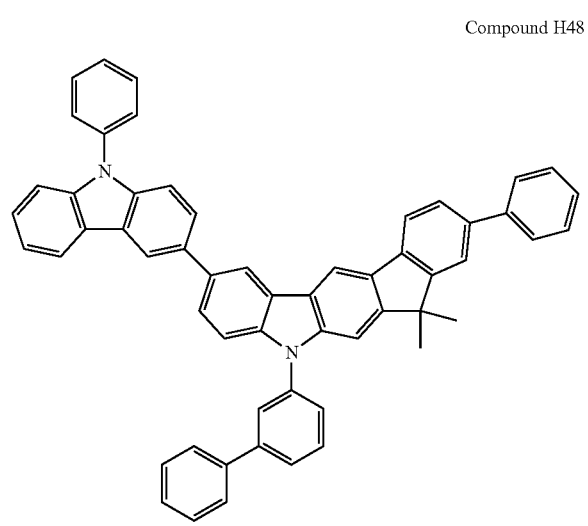 [SMILES: CC1(C)c2cc(-c3ccccc3)ccc2-c2cc3c4cc(-c5ccc6c(c5)c5ccccc5n6-c5ccccc5)ccc4n(-c4cccc(-c5ccccc5)c4)c3cc21]
Compound H52
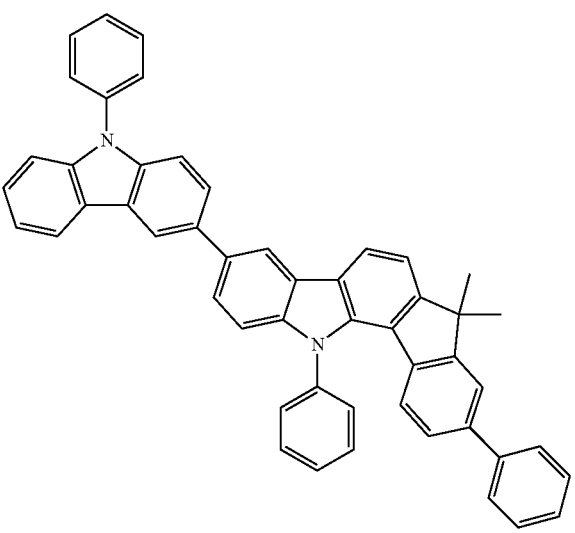

Compound H55
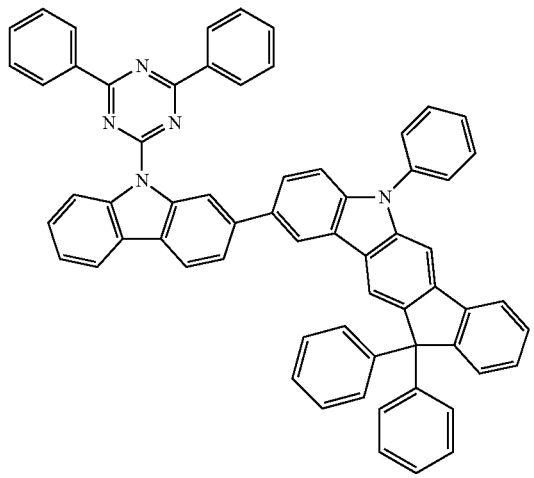
Compound H56
Compound H57
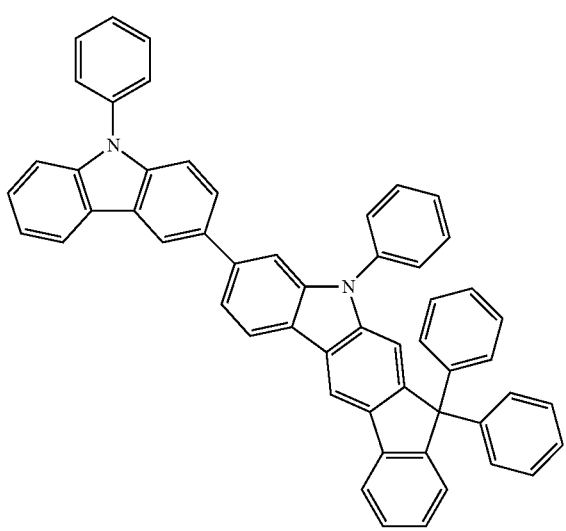
Compound H58
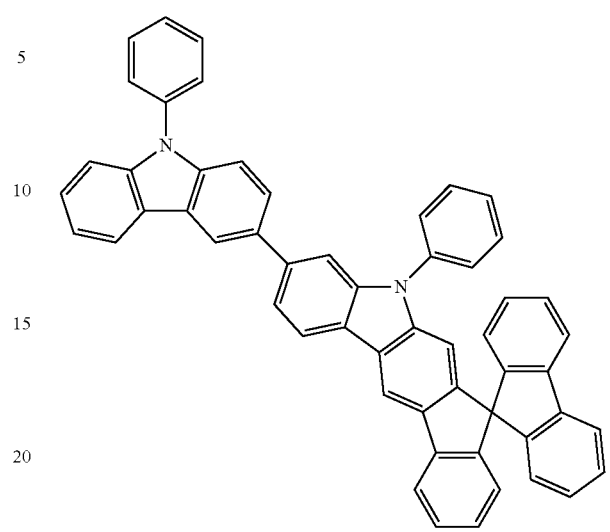
Compound H59
Compound H60
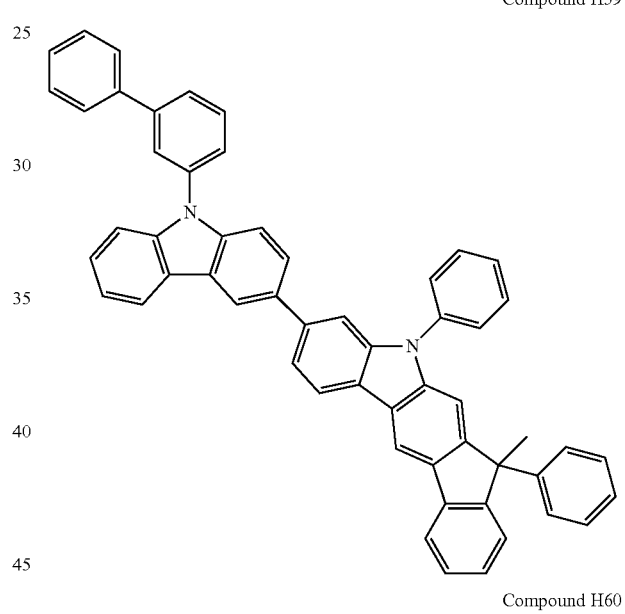
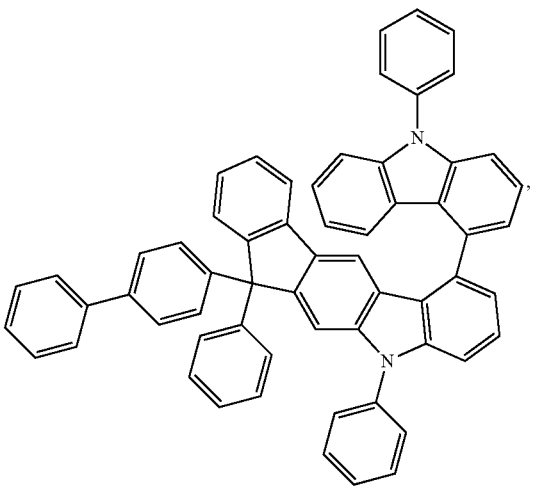

and a second compound represented by Formula B:

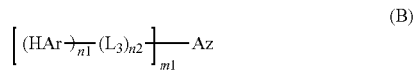
(B)

wherein HAr is selected from substituted or unsubstituted $C_6$-$C_{30}$ aryl groups and substituted or unsubstituted $C_5$-$C_{30}$ heterocyclic groups, $L_3$ is a single bond or a linker selected from substituted or unsubstituted $C_1$-$C_{60}$ alkylene groups, substituted or unsubstituted $C_2$-$C_{60}$ alkenylene groups, substituted or unsubstituted $C_2$-$C_{60}$ alkynylene groups, substituted or unsubstituted $C_3$-$C_{60}$ cycloalkylene groups, substituted or unsubstituted $C_2$-$C_{60}$ heterocycloalkylene groups, substituted or unsubstituted $C_6$-$C_{60}$ arylene groups, and substituted or unsubstituted $C_2$-$C_{60}$ heteroarylene groups, n1 and m1 are each independently an integer from 1 to 3, n2 is an integer from 0 to 3, and Az is a nitrogen-containing ring represented by Formula C:

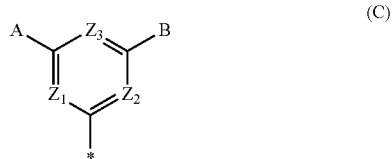
(C)

wherein $Z_1$ to $Z_3$ are identical to or different from each other and are each independently N or CR, with the proviso that at least one of $Z_1$ to $Z_3$ is N, A, B, and R are each independently selected from hydrogen, deuterium, substituted or unsubstituted $C_1$-$C_{30}$ alkyl groups, substituted or unsubstituted $C_2$-$C_{30}$ alkenyl groups, substituted or unsubstituted $C_3$-$C_{30}$ cycloalkyl groups, substituted or unsubstituted $C_5$-$C_{30}$ cycloalkenyl groups, substituted or unsubstituted $C_1$-$C_{30}$ alkoxy groups, substituted or unsubstituted $C_6$-$C_{30}$ aryloxy groups, substituted or unsubstituted $C_1$-$C_{30}$ alkylthioxy groups, substituted or unsubstituted $C_5$-$C_{30}$ arylthioxy groups, substituted or unsubstituted $C_1$-$C_{30}$ alkylamine groups, substituted or unsubstituted $C_5$-$C_{30}$ arylamine groups, substituted or unsubstituted $C_6$-$C_{50}$ aryl groups, substituted or unsubstituted $C_3$-$C_{50}$ heteroaryl groups containing O, N or S as a heteroatom, substituted or unsubstituted silyl groups, substituted or unsubstituted germanium groups, substituted or unsubstituted boron groups, substituted or unsubstituted aluminum groups, a carbonyl group, a phosphoryl group, an amino group, a nitrile group, a hydroxyl group, a nitro group, halogen groups, a selenium group, a tellurium group, an amide group, and an ester group, with the proviso that each of A, B, and R optionally forms an aliphatic, aromatic, heteroaliphatic or heteroaromatic fused ring with the adjacent group and wherein at least one of A and B are not phenyl groups.

3. The organic light emitting device according to claim 1, wherein the organic layer comprises a light emitting layer, a hole transport layer between the light emitting layer and the first electrode, and an electron transport layer between the light emitting layer and the second electrode and wherein the light emitting layer comprises the first compound represented by Formula A and the second compound represented by Formula B.

4. The organic light emitting device according to claim 1, wherein the light emitting layer comprise a dopant compound.

5. The organic light emitting device according to claim 1, wherein the first compound, the second compound, and the dopant compound are mixed in a weight ratio of 1:0.01-99: 0.01-15.

6. The organic light emitting device according to claim 1, further comprising one or more blue, red or green light emitting layers to achieve white light emission.

7. The organic light emitting device according to claim 2, wherein the organic layer comprises a light emitting layer, a hole transport layer between the light emitting layer and the first electrode, and an electron transport layer between the light emitting layer and the second electrode and wherein the light emitting layer comprises the first compound represented by Formula A and the second compound represented by Formula B.

8. The organic light emitting device according to claim 2, wherein the light emitting layer comprise a dopant compound.

9. The organic light emitting device according to claim 2, wherein the first compound, the second compound, and the dopant compound are mixed in a weight ratio of 1:0.01-99: 0.01-15.

10. The organic light emitting device according to claim 2, further comprising one or more blue, red or green light emitting layers to achieve white light emission.

11. An organic light emitting device comprising a first electrode, a second electrode opposite to the first electrode, and at least one organic layer interposed between the first and second electrodes, wherein the organic layer comprises a first compound selected from Compounds H3 to H5, H7, H13, H19, H23, H24, H26, H27, H33, H41, H45, H46, H48, H50 to H52, and H55 to H60:

Compound H3

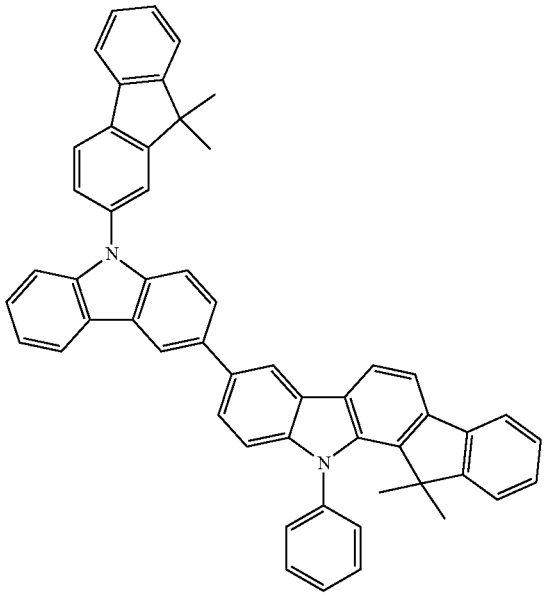

Compound H4
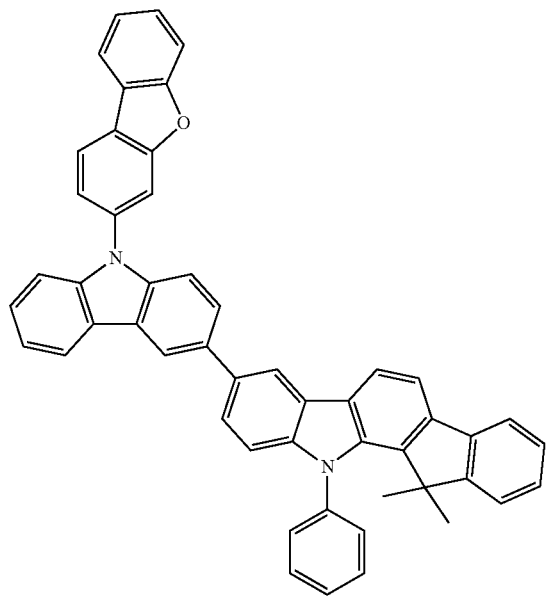
Compound H7
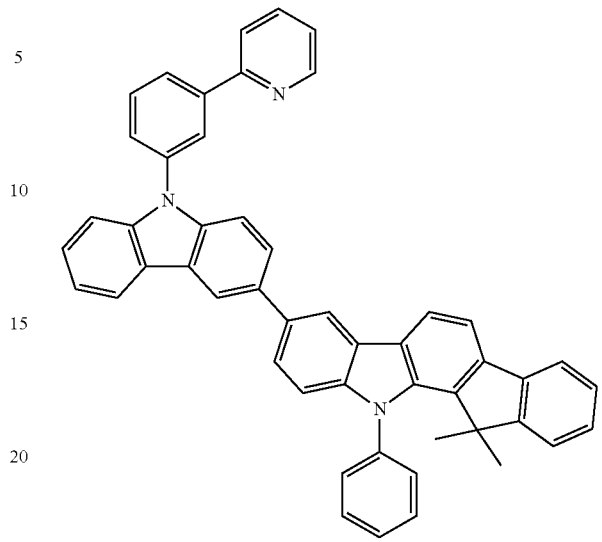
Compound H13
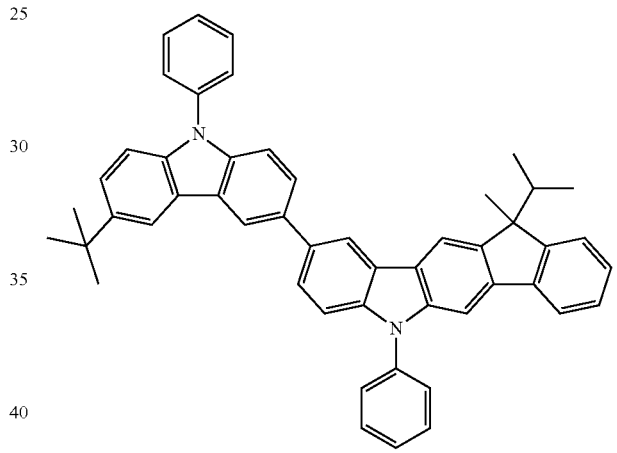
Compound H5
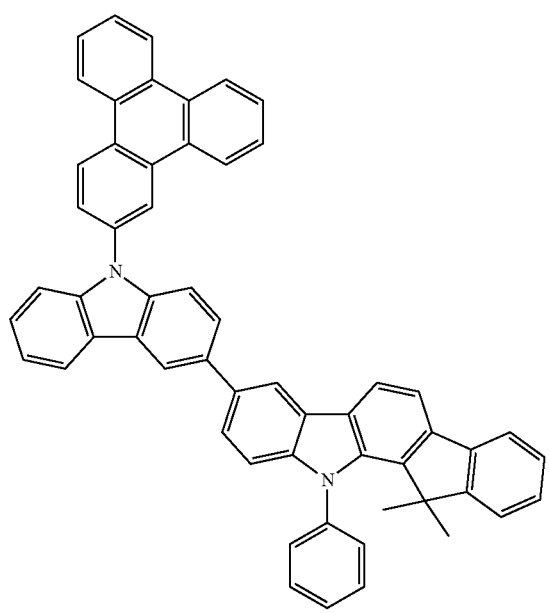
Compound H19
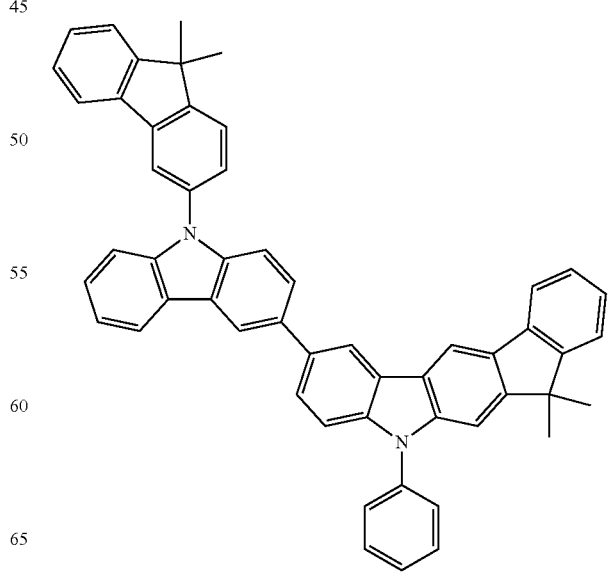

Compound H23
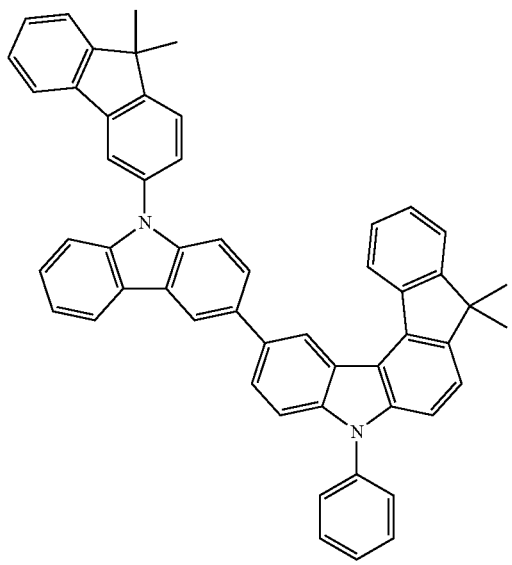
Compound H24
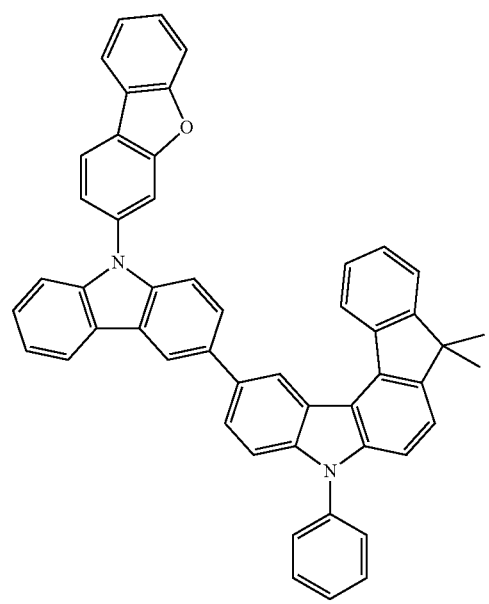
Compound H26
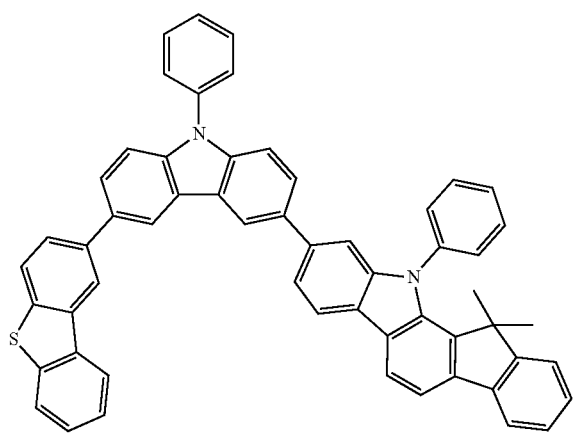
Compound H27
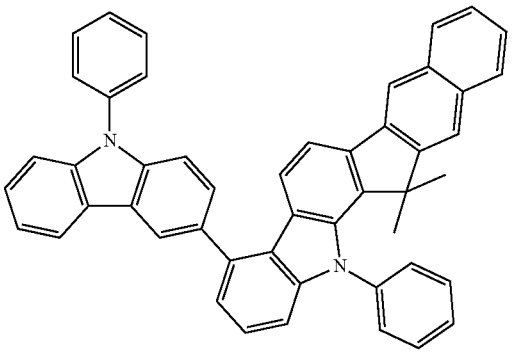
Compound H33
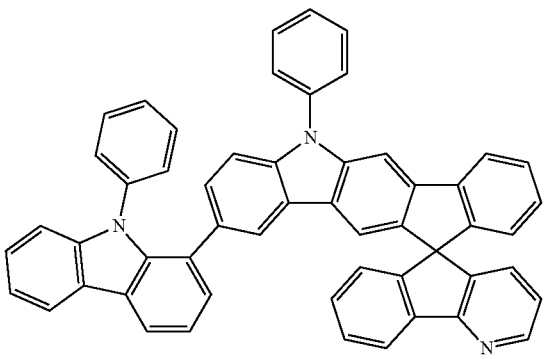
Compound H41
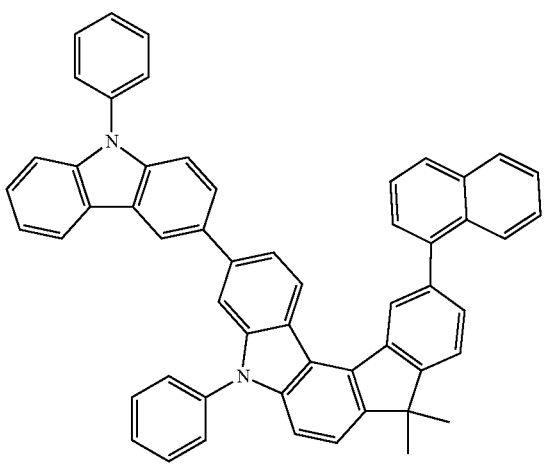

Compound H45
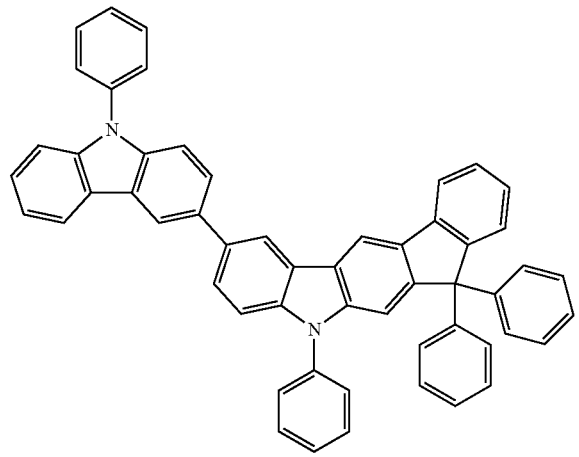
Compound H50
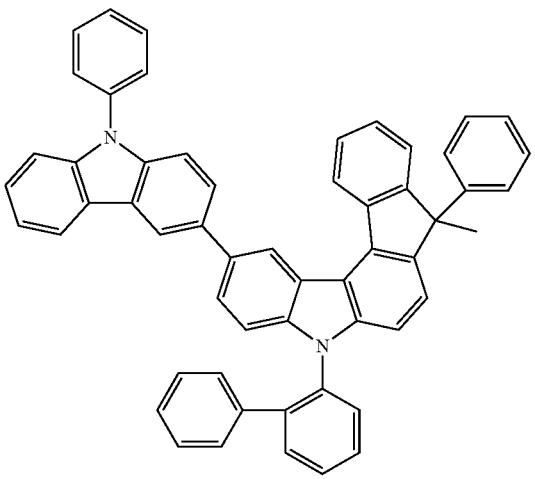
Compound H46
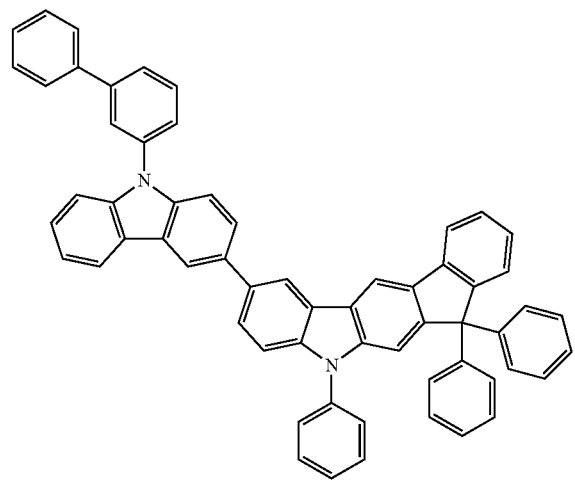
Compound H51
Compound H48
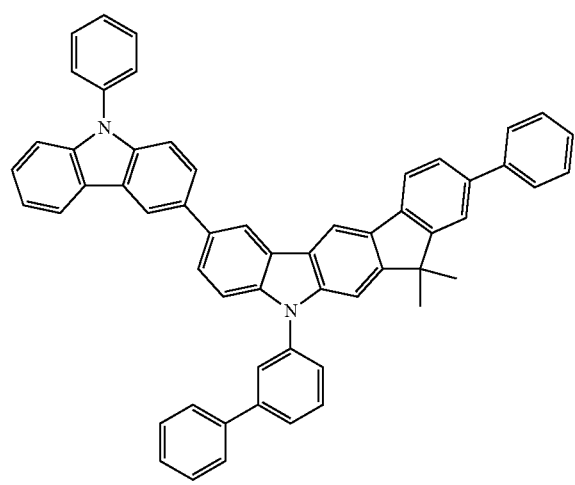
Compound H52
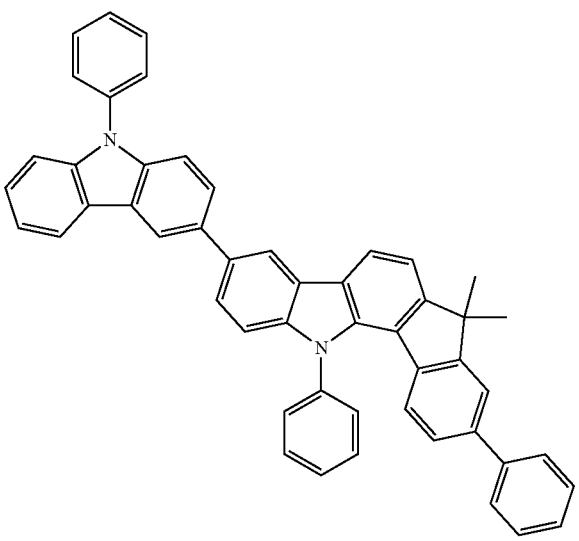

Compound H55
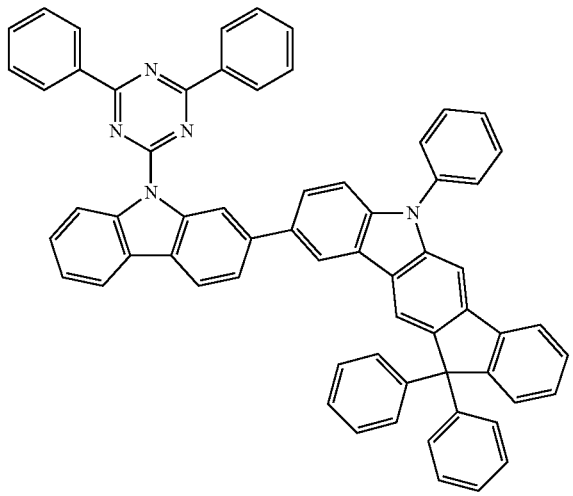
Compound H56
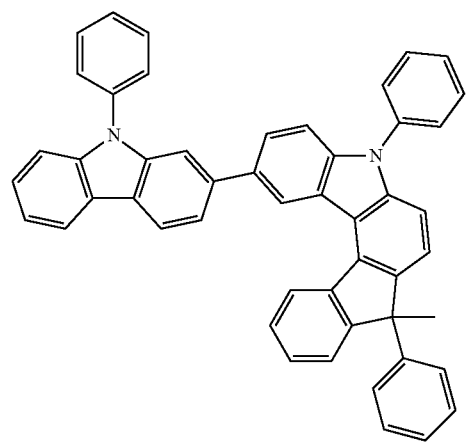
Compound H57
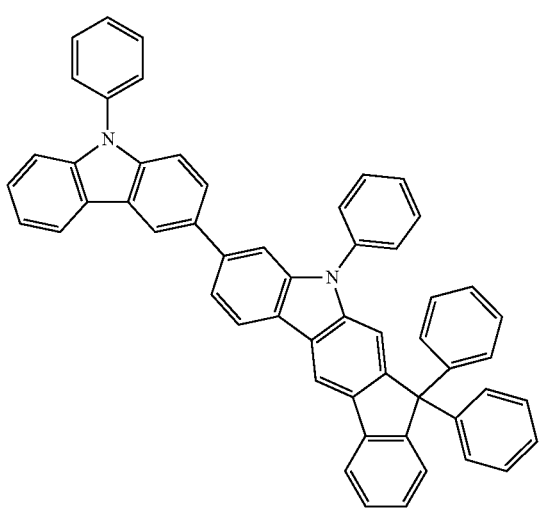
Compound H58
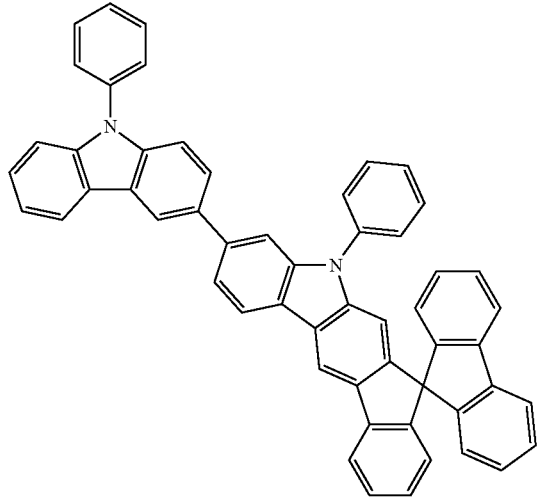
Compound H59
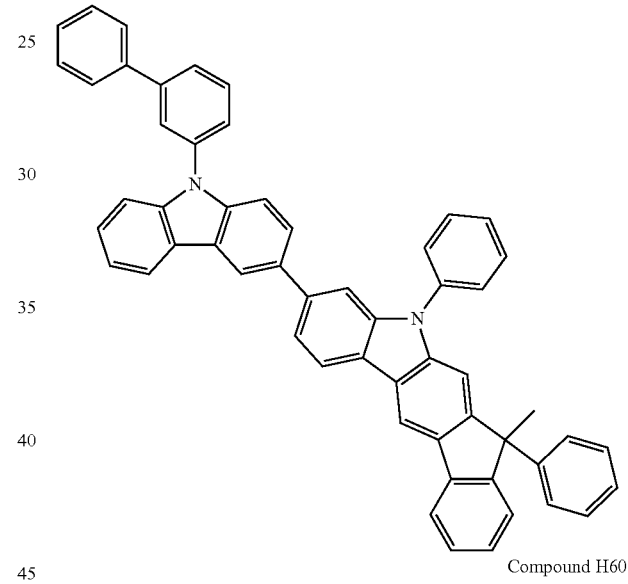
Compound H60
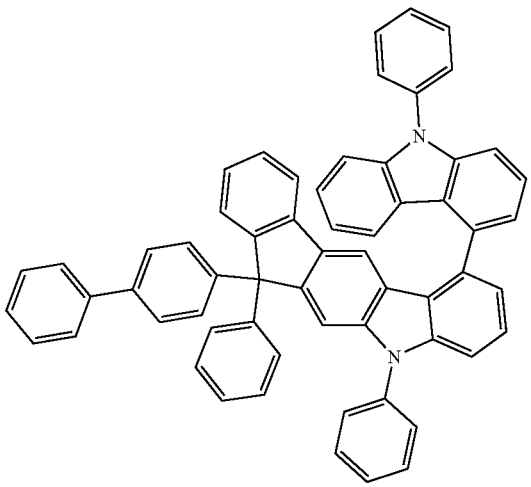
and a second compound selected from Compounds E9 to E23, and E25 to E28, and E30 to E44, and E46 to E132:

Compound E9
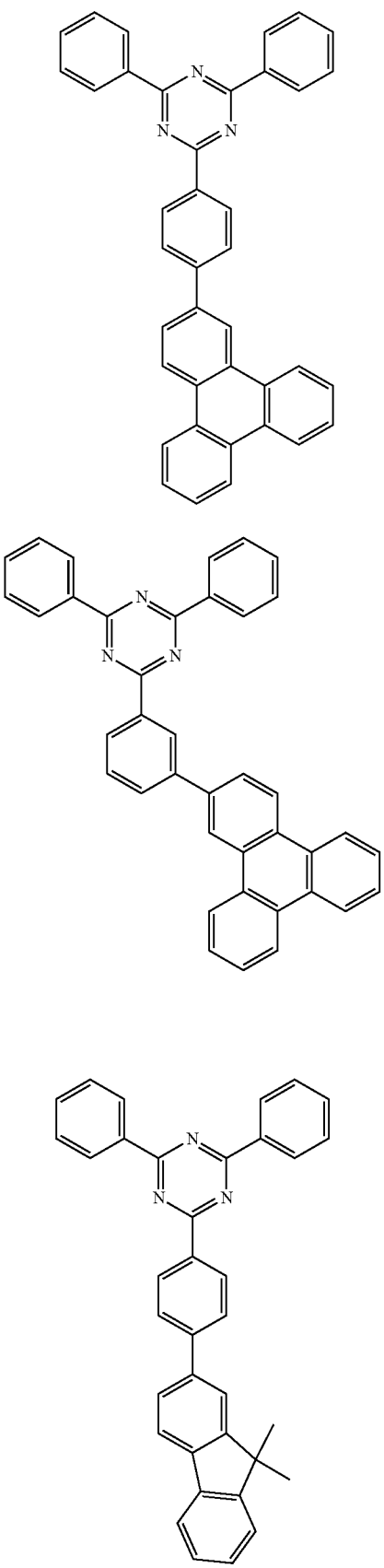
Compound E10
Compound E11
Compound E12
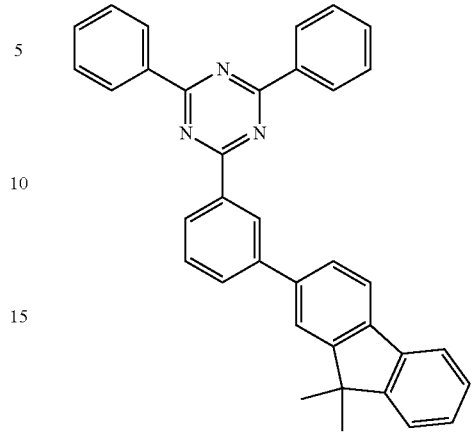
Compound E13
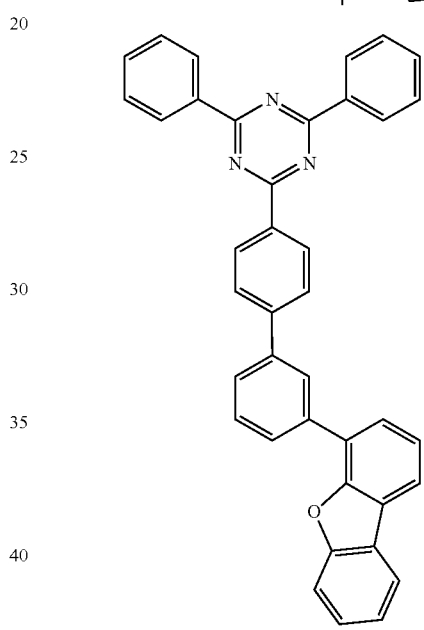
Compound E14
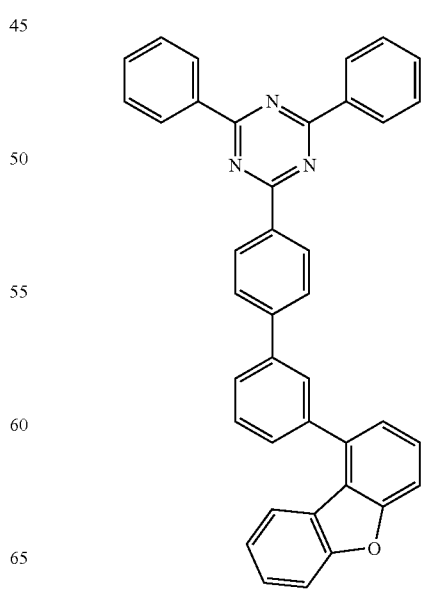

Compound E15
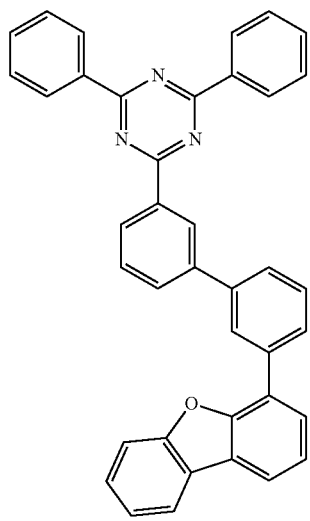
Compound E16
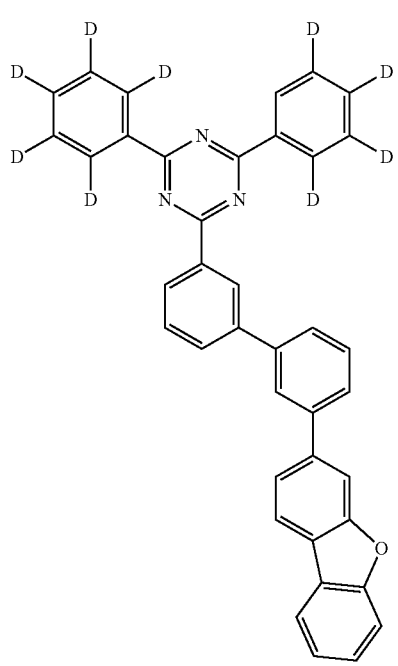
Compound E17
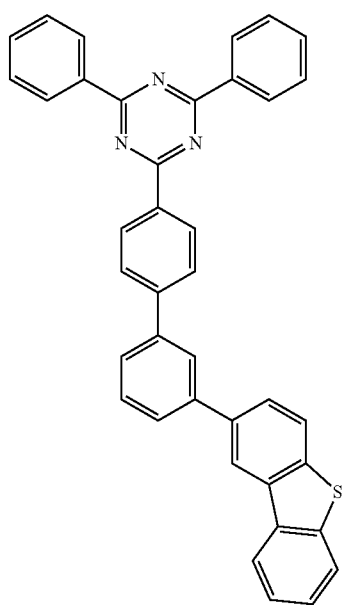
Compound E18
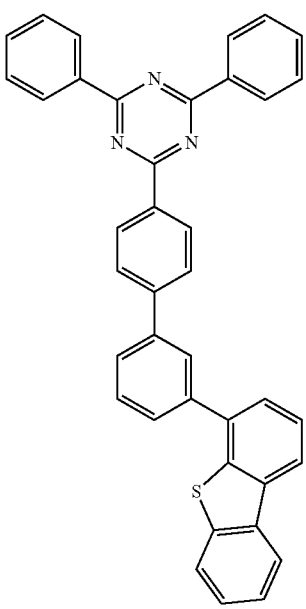

Compound E19
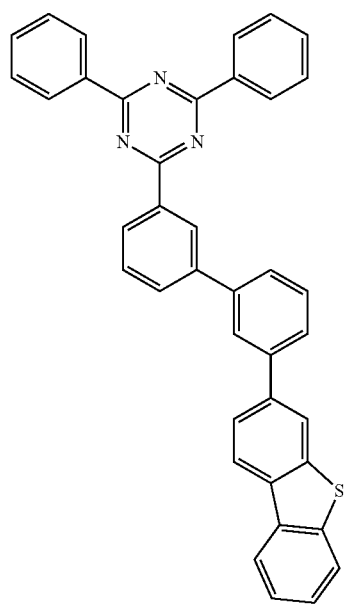
Compound E20
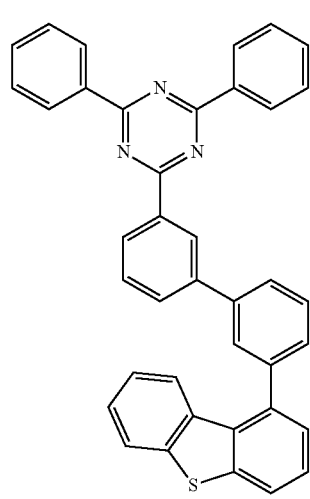
Compound E21
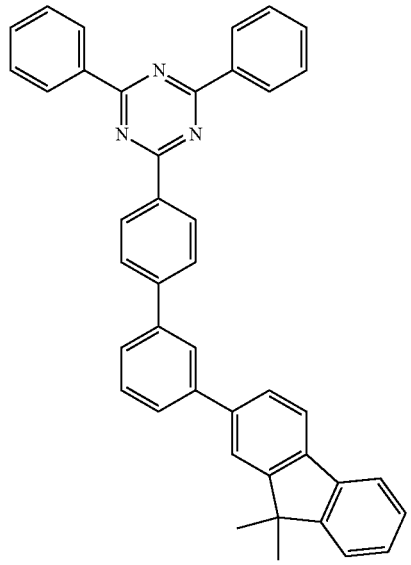
Compound E22
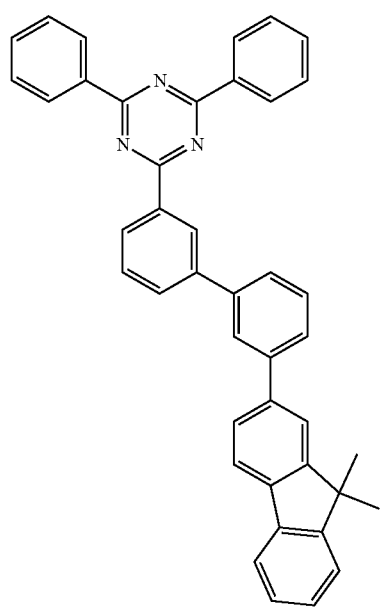

Compound E23
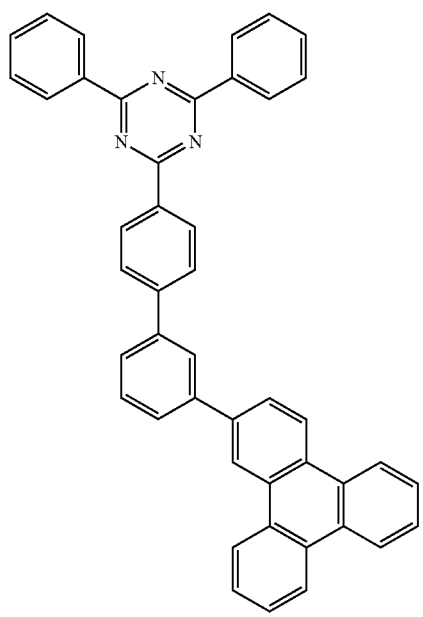
Compound E25
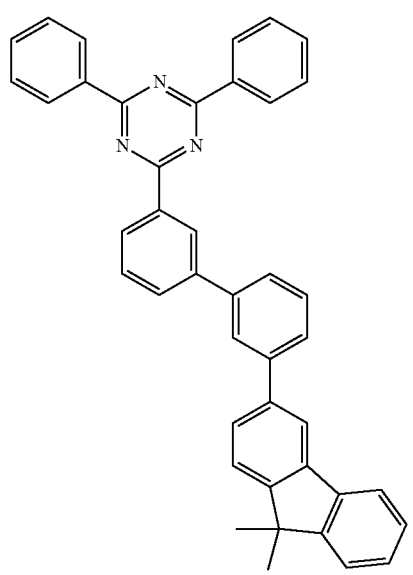
Compound E26
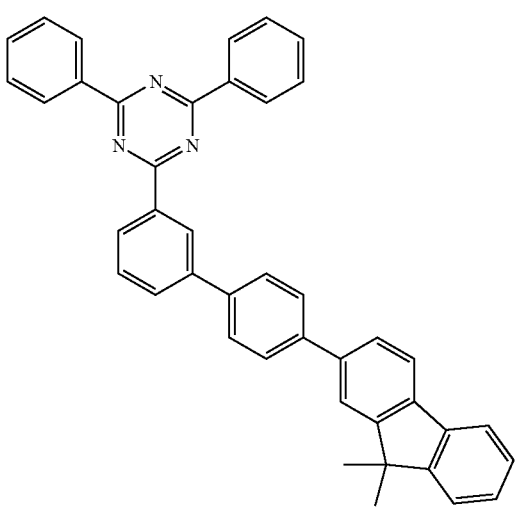
Compound E27
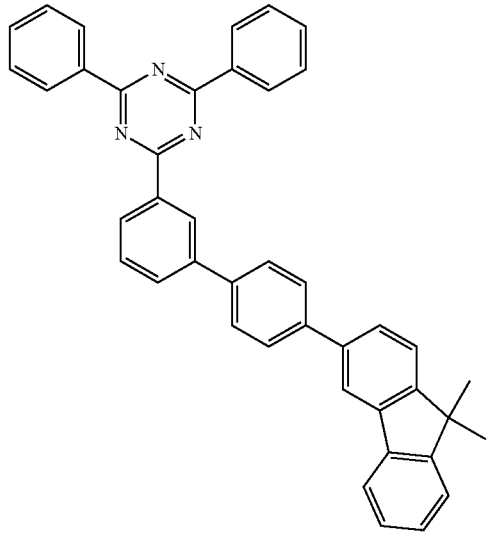

Compound E28
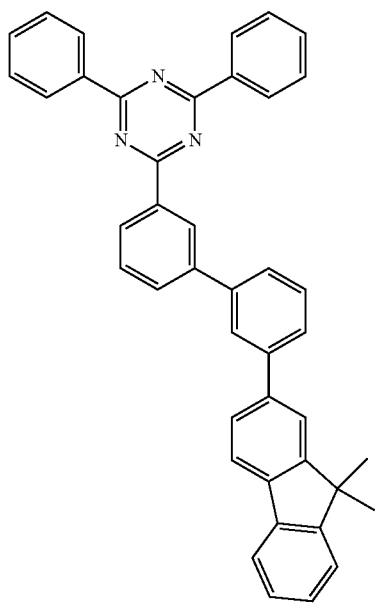
Compound E30
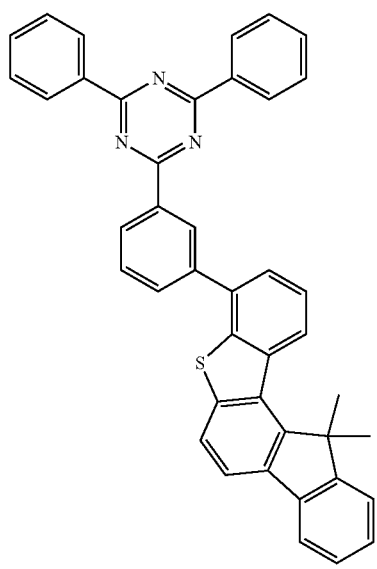
Compound E31
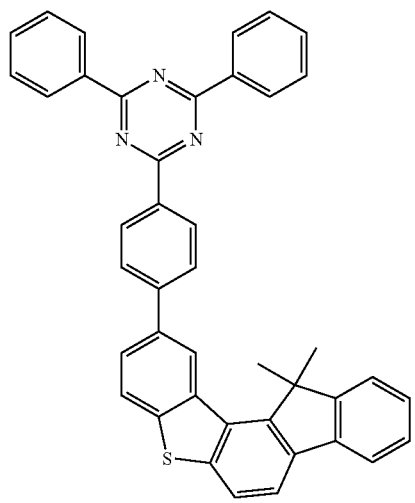
Compound E32
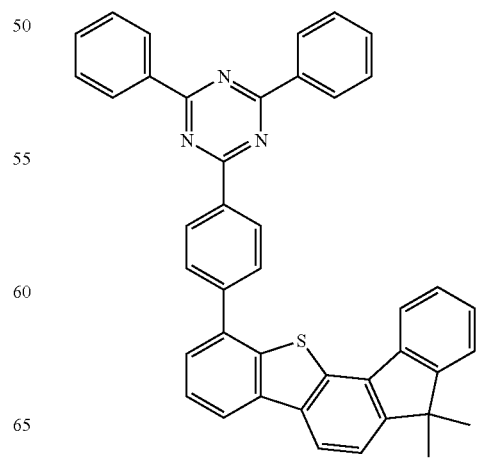
Compound E33

Compound E34
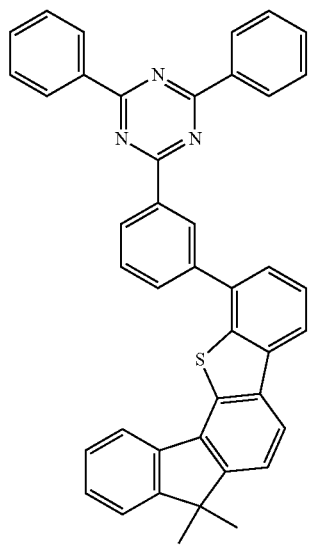
Compound E35
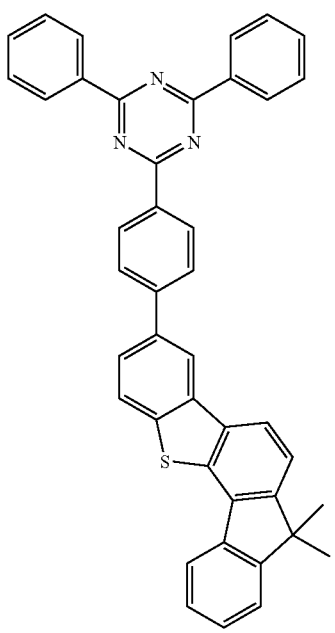
Compound E36
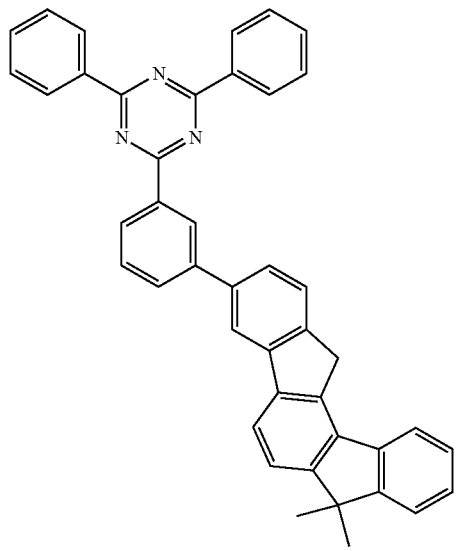
Compound E37
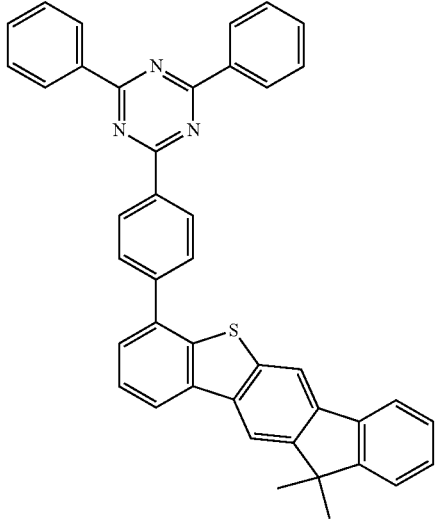

Compound E38
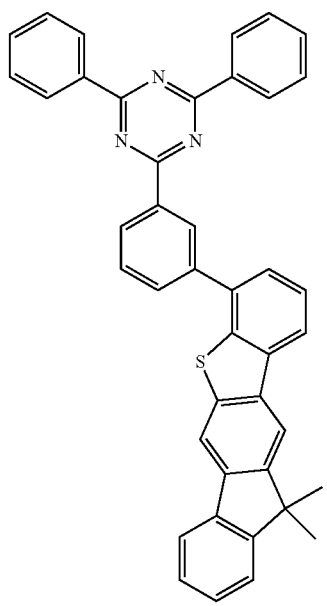
Compound E40
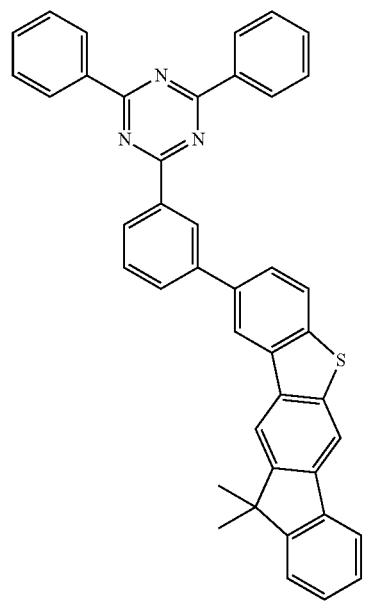
Compound E39
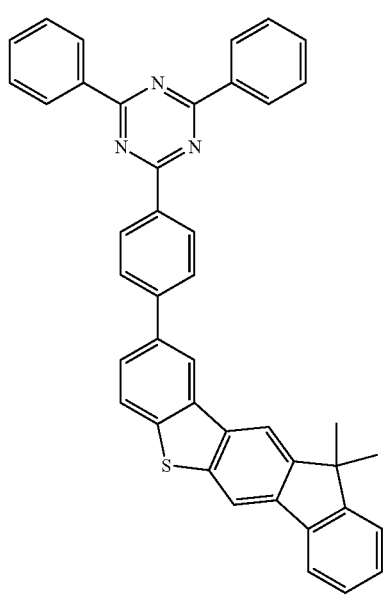
Compound E41
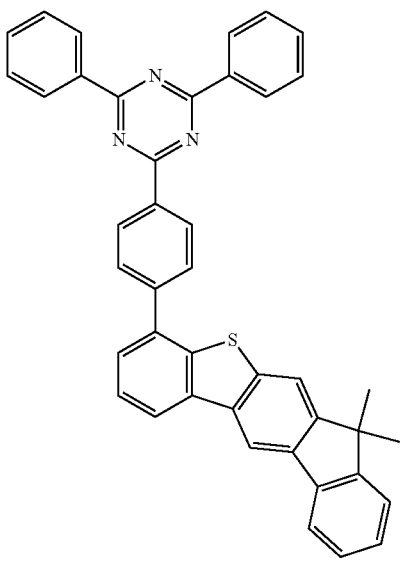

Compound E42
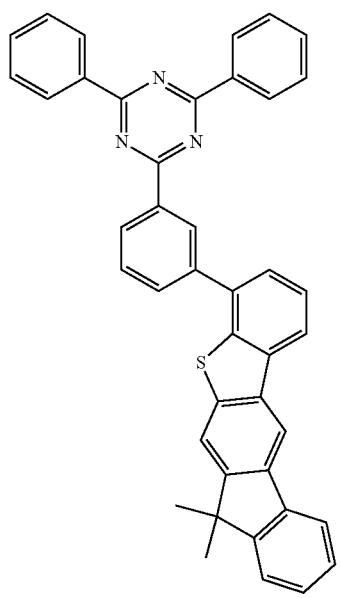
Compound E44
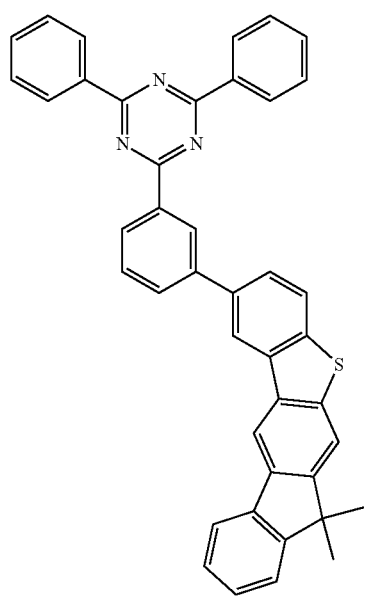
Compound E43
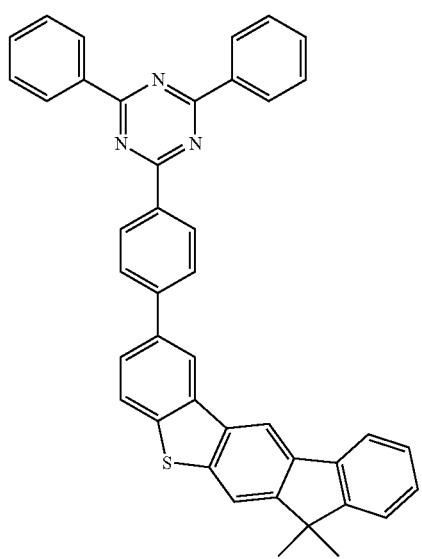
Compound E46
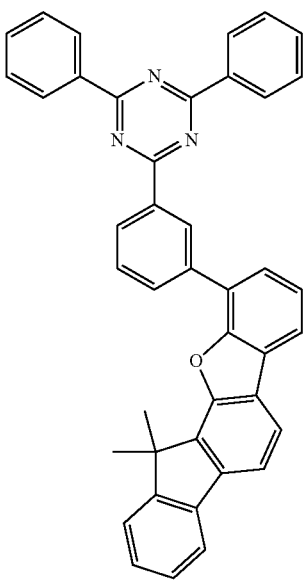

Compound E47
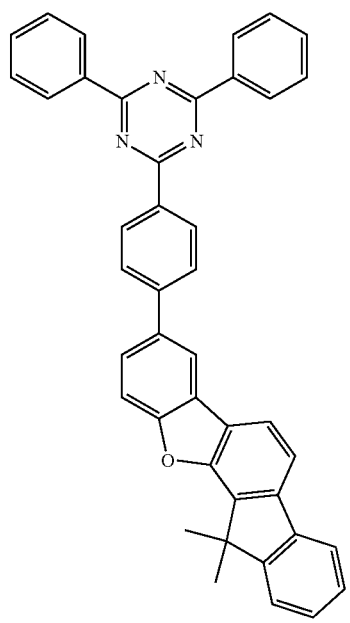
Compound E48
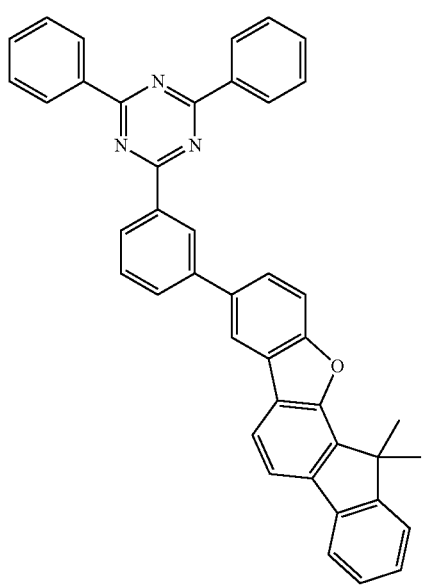
Compound E49
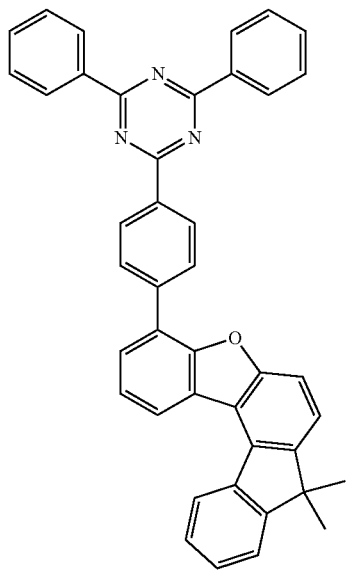
Compound E50
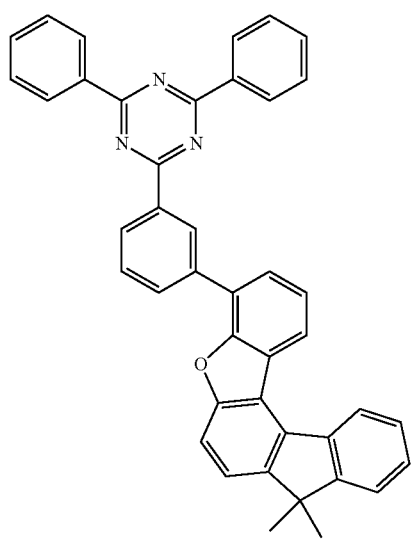
Compound E51

Compound E52
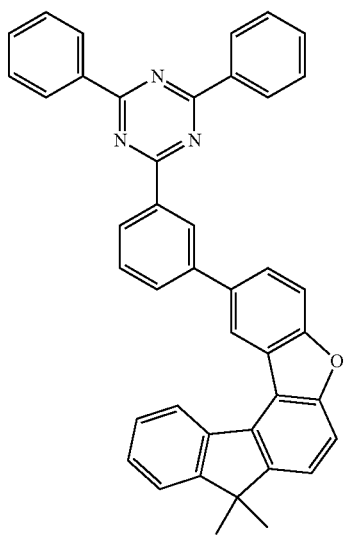
Compound E53
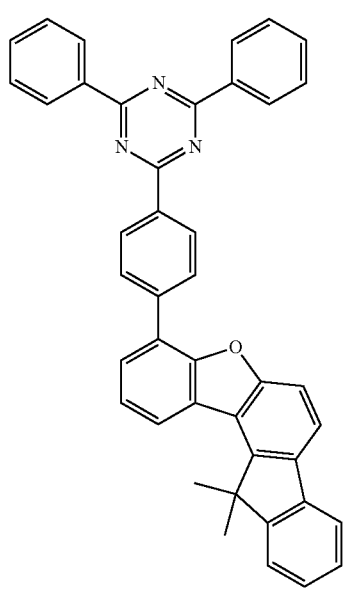
Compound E54
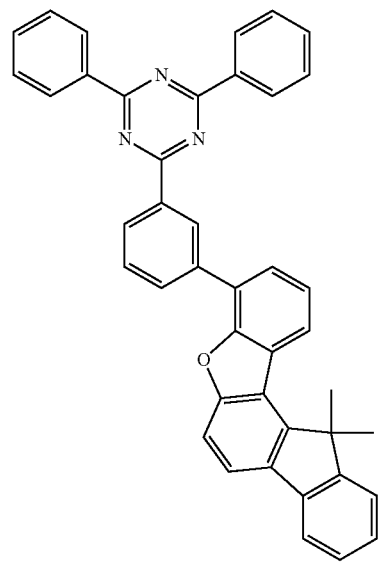
Compound E55
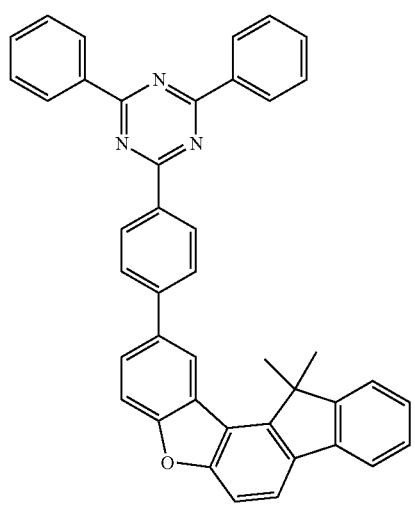
Compound E56
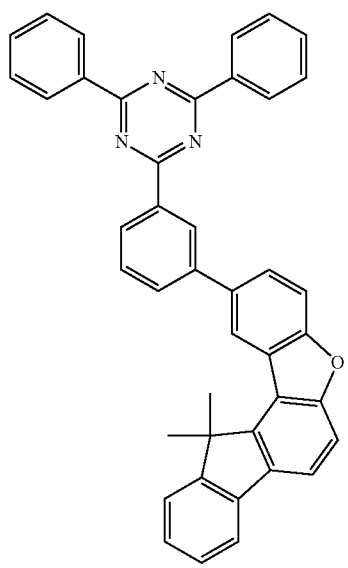

Compound E57
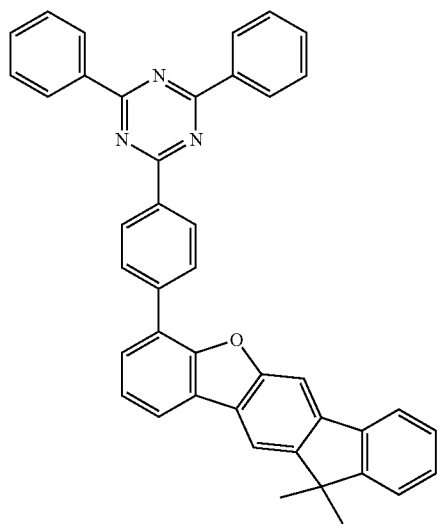
Compound E59
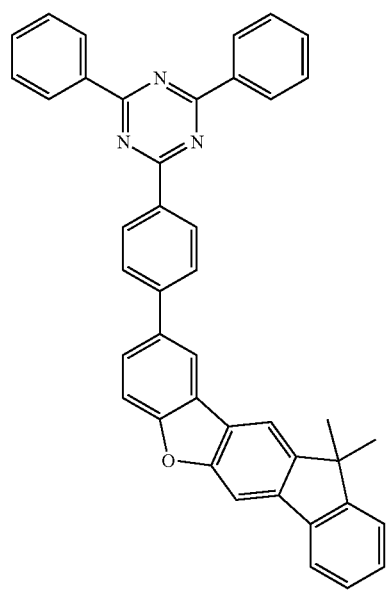
Compound E58
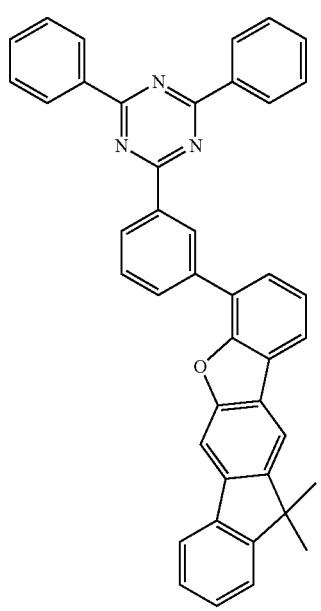
Compound E60
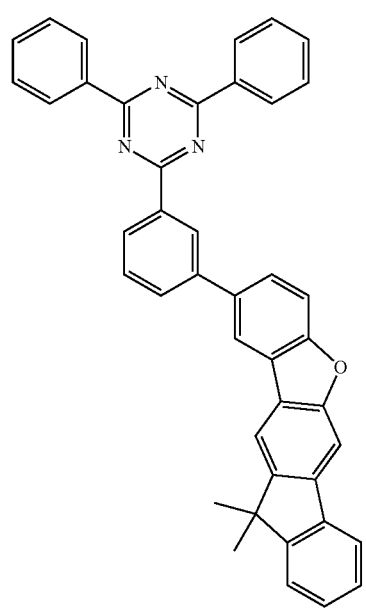

Compound E61
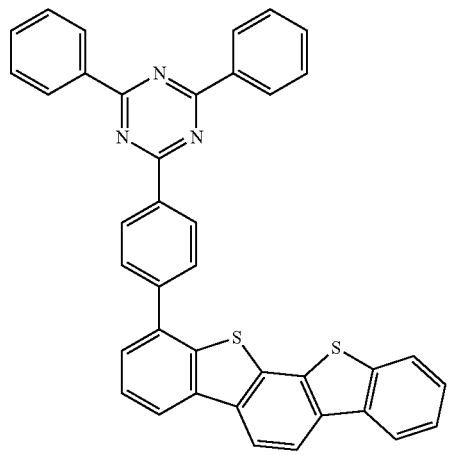
Compound E62
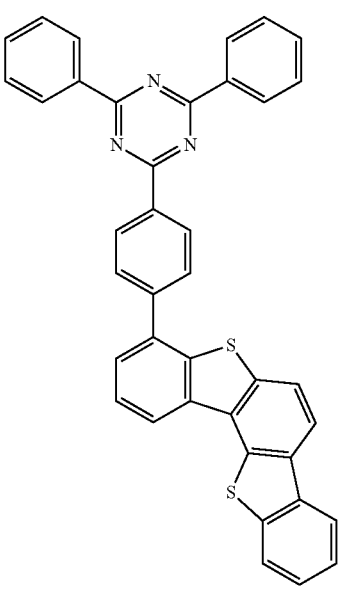
Compound E63
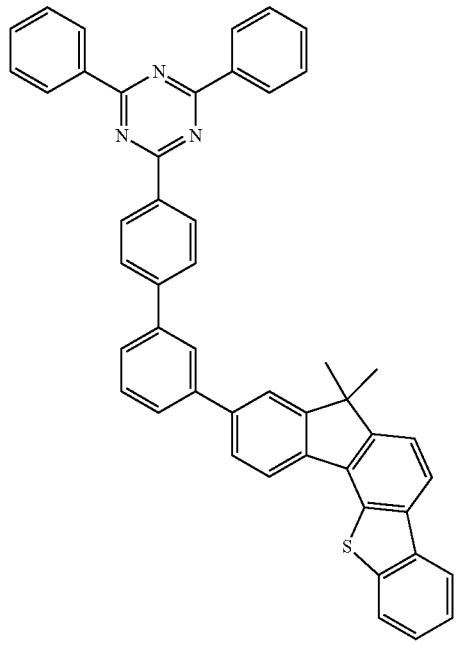
Compound E64
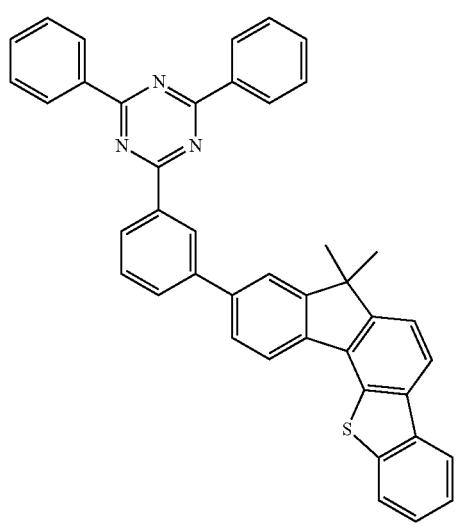
Compound E65
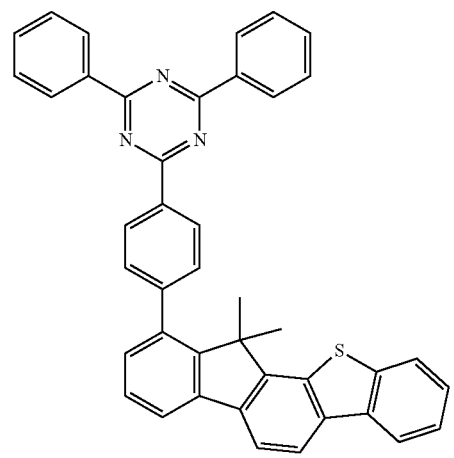

Compound E66
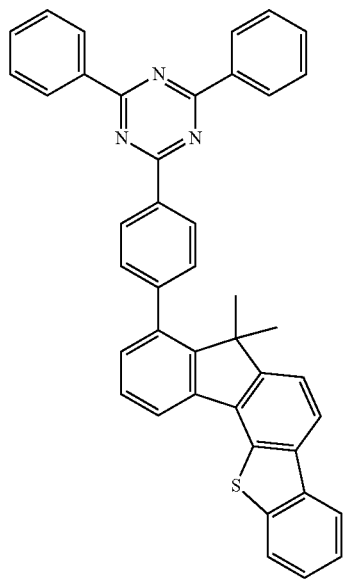
Compound E67
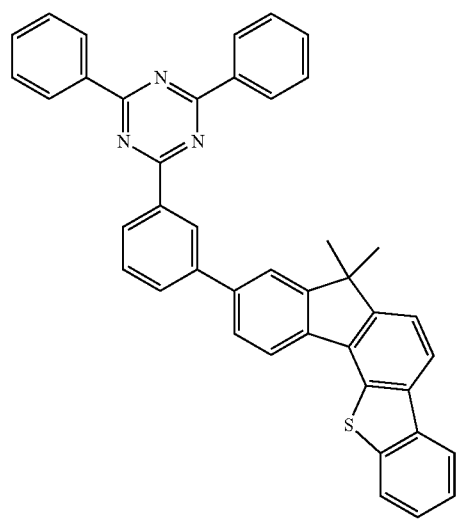
Compound E68
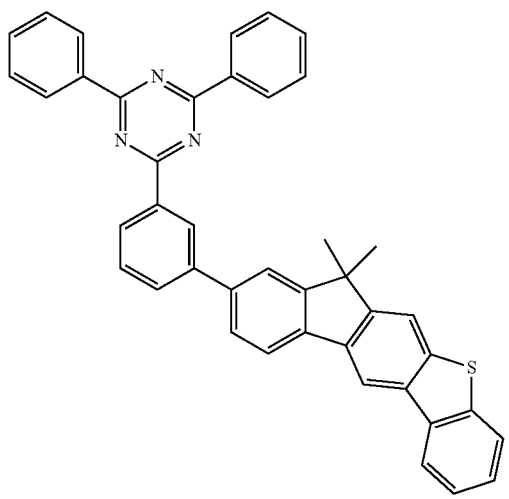
Compound E69
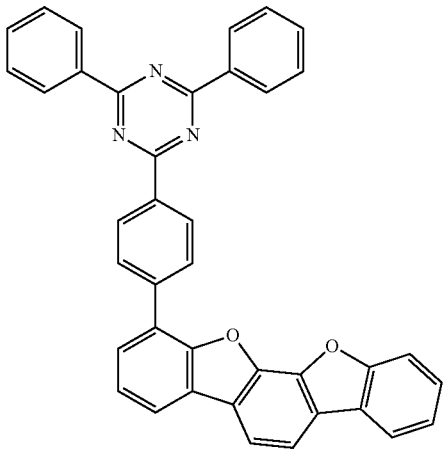
Compound E70
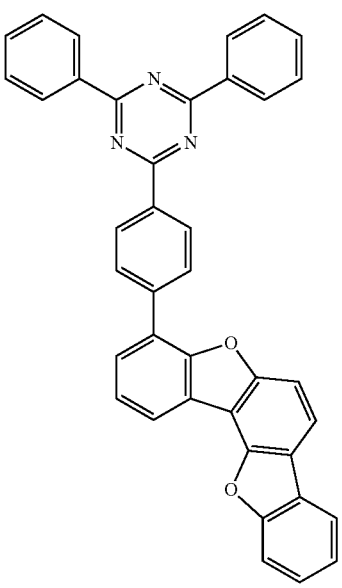

-continued
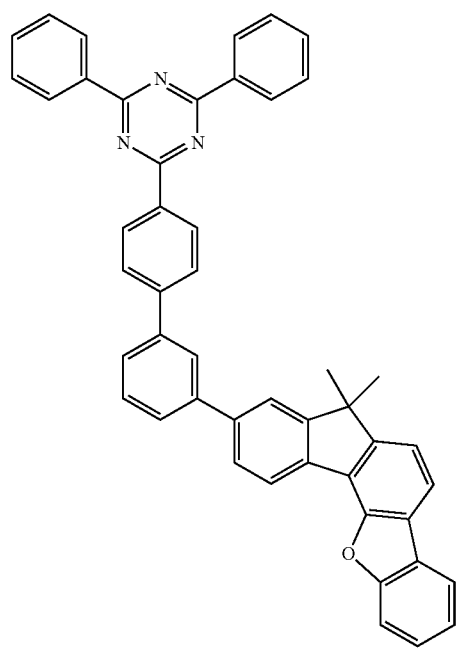
Compound E71
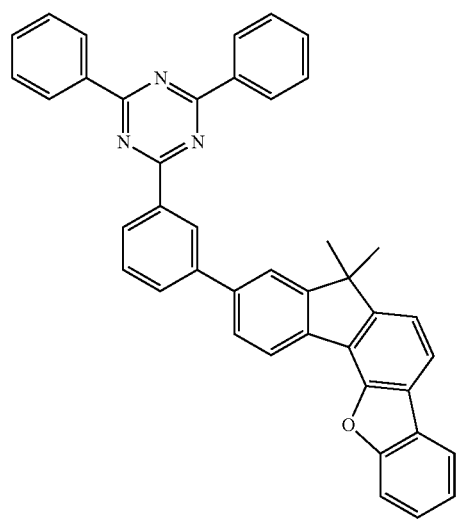
Compound E72
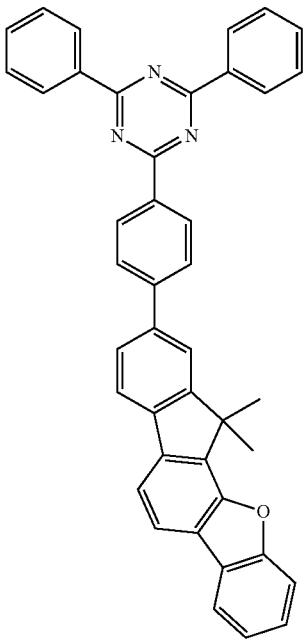
Compound E73
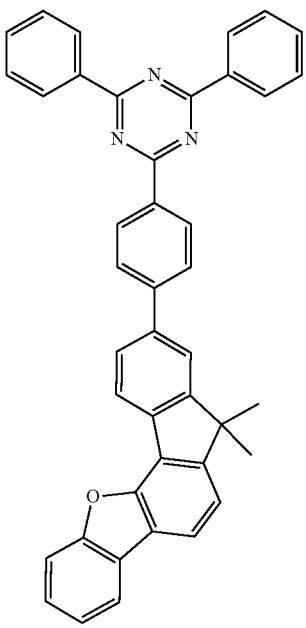
Compound E74

Compound E75
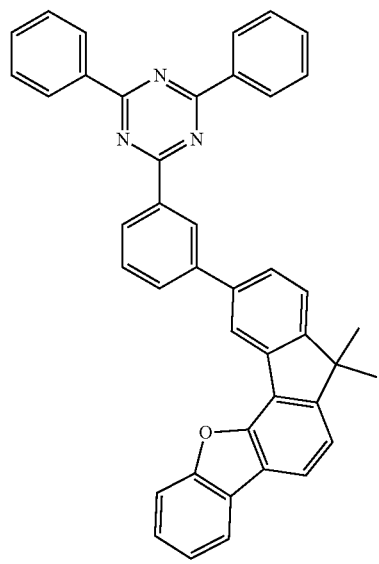
Compound E76
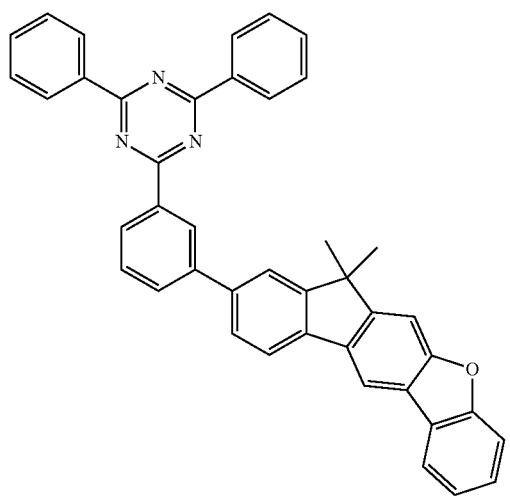
Compound E77
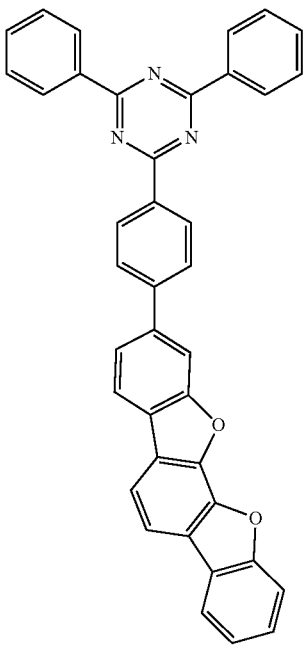
Compound E78
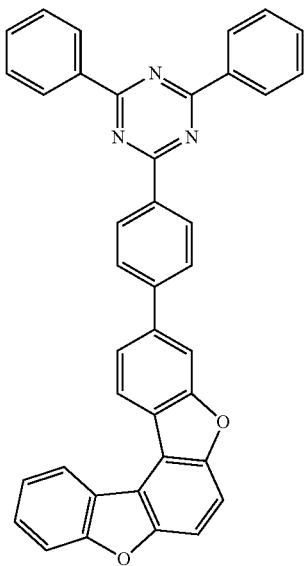

Compound E79
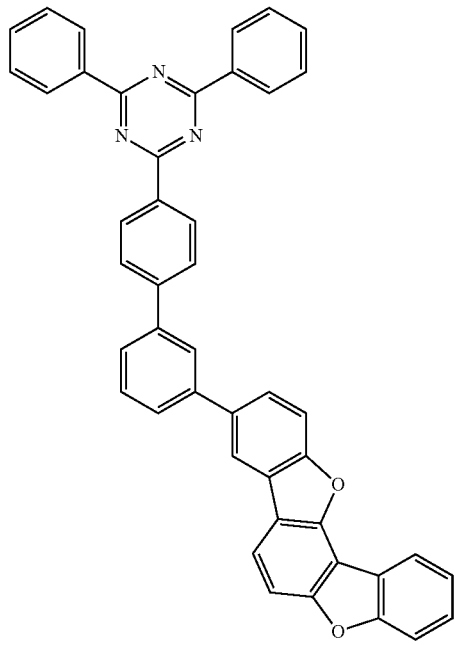
Compound E81
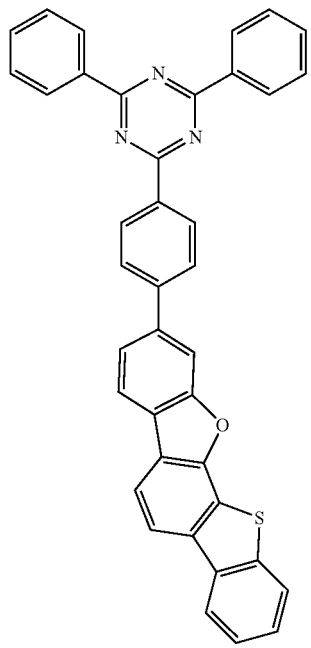
Compound E80
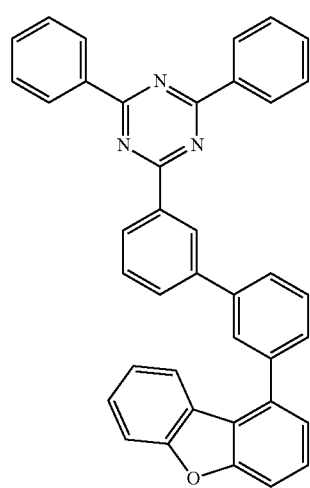
Compound E82
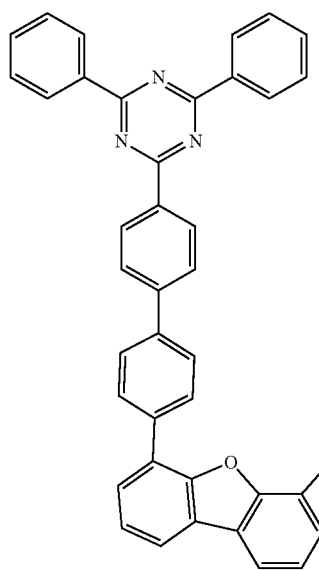

Compound E83
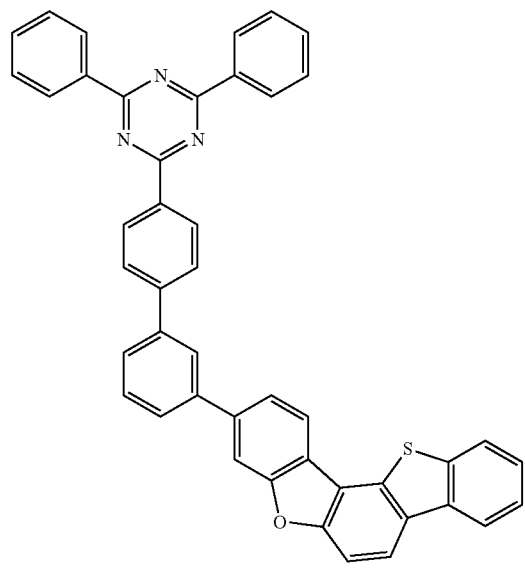
Compound E85
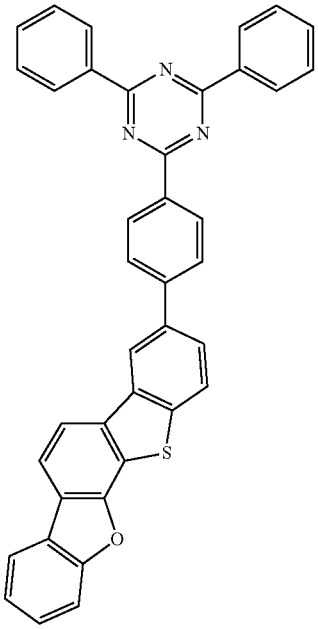
Compound E84
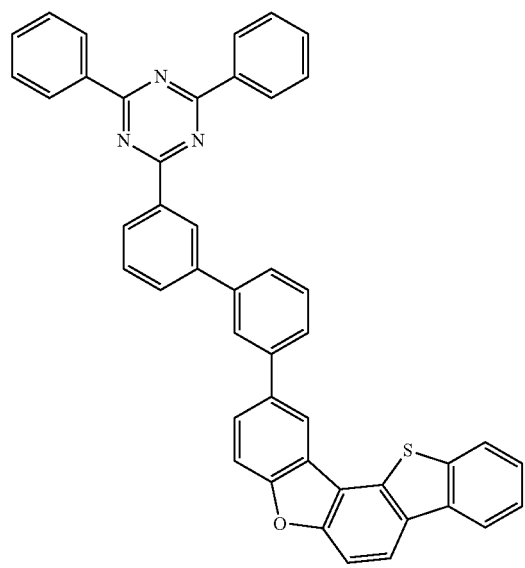
Compound E86
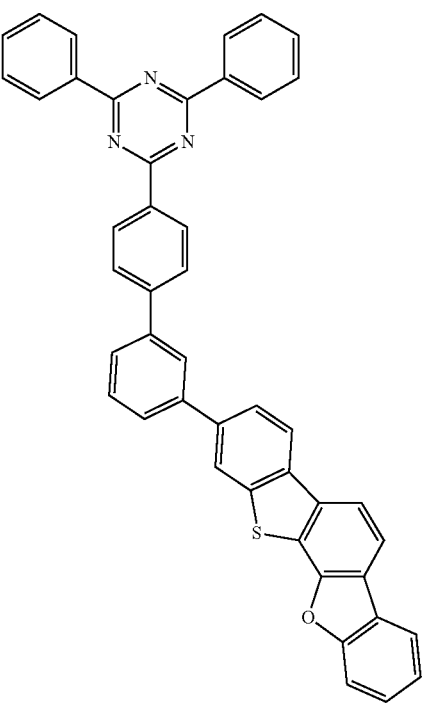

Compound E87
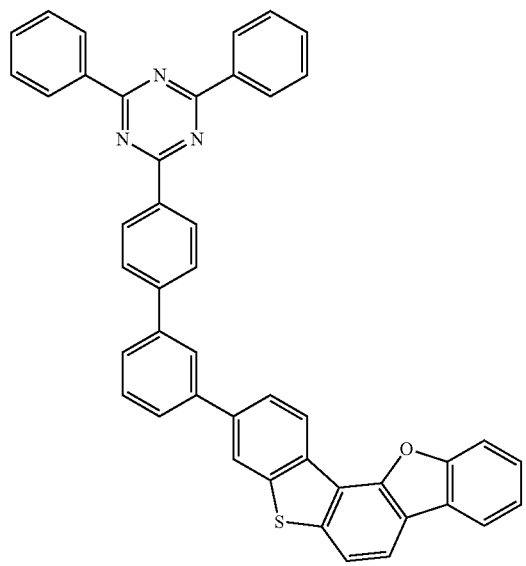
Compound E88
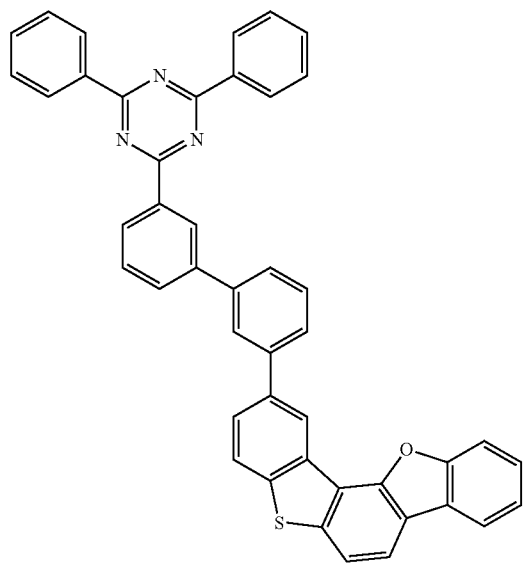
Compound E89
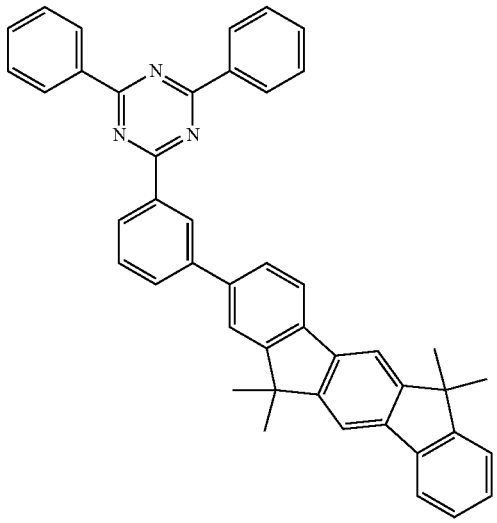
Compound E90
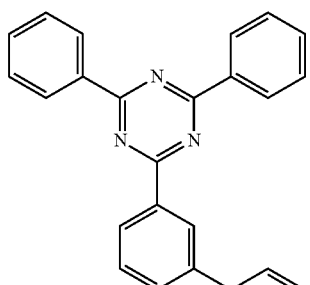
Compound E91
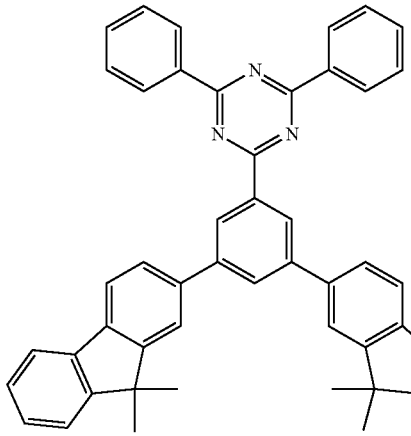

Compound E92
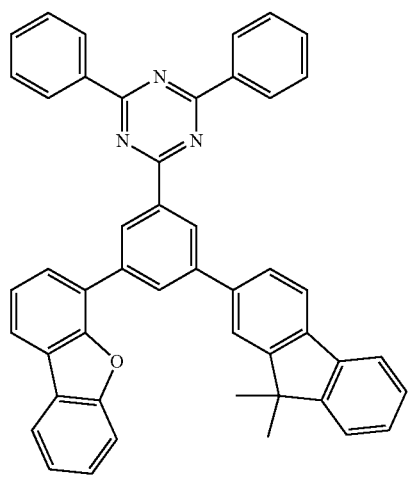
Compound E95
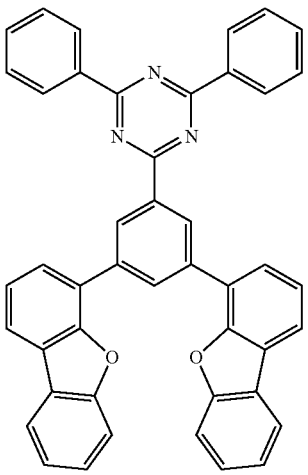
Compound E93
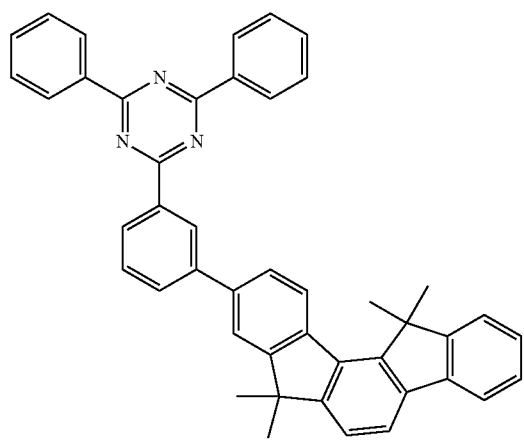
Compound E96
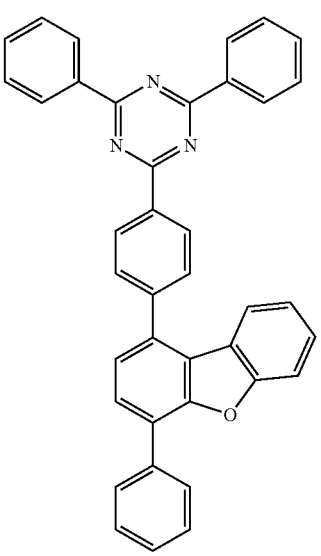
Compound E94
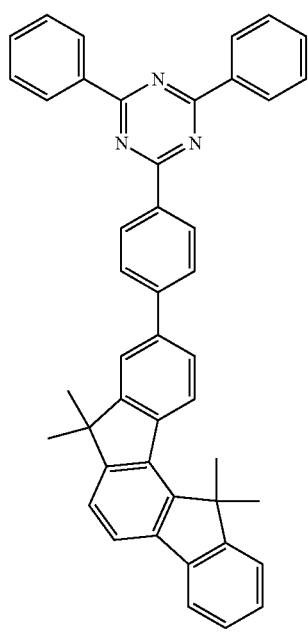
Compound E97
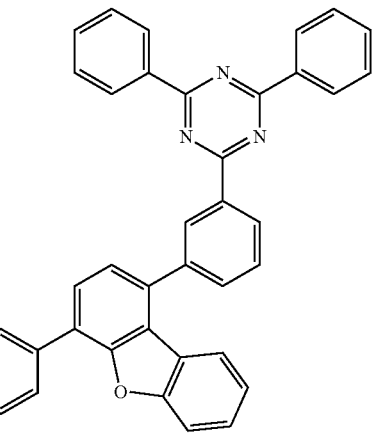

Compound E98
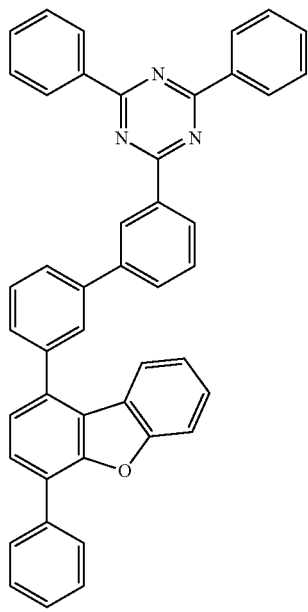
Compound E100
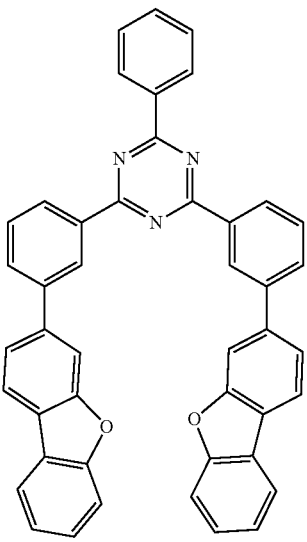
Compound E101
Compound E99
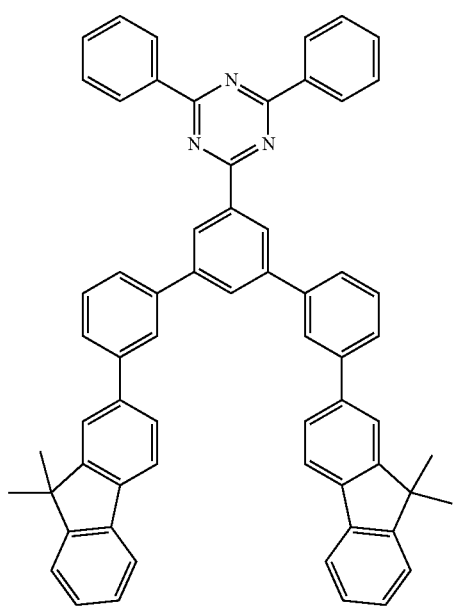
Compound E102
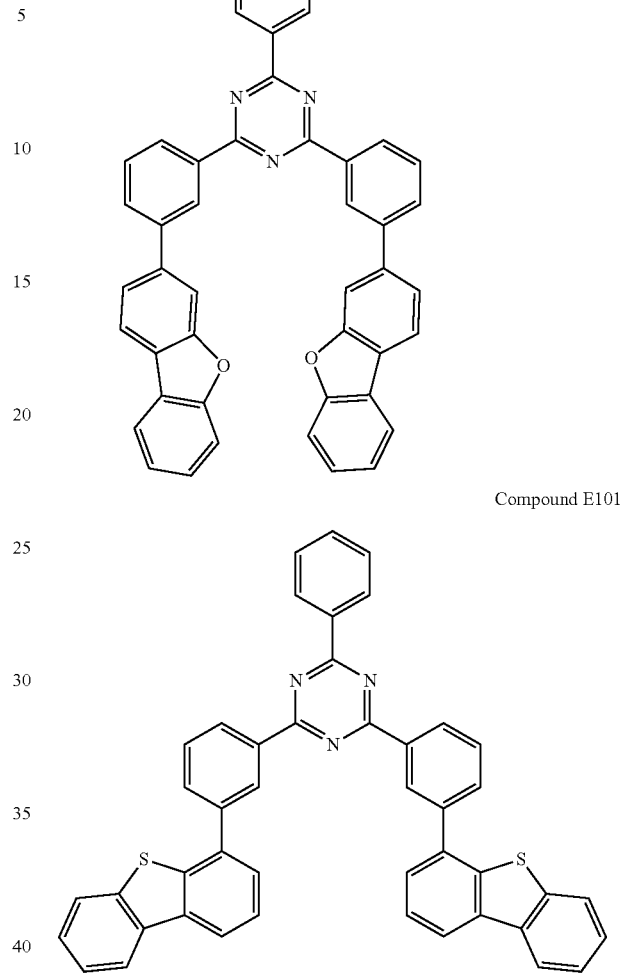
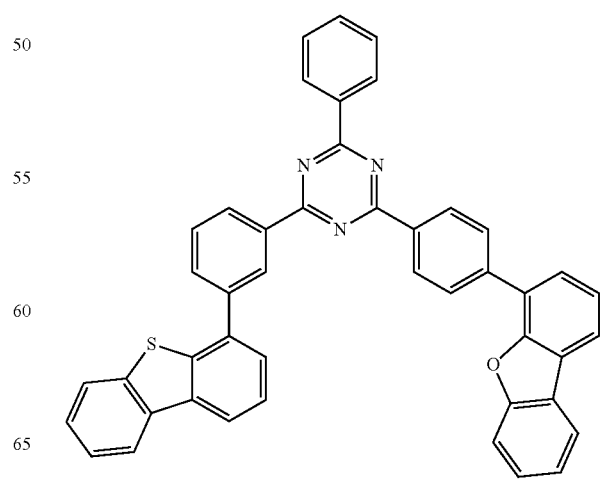

Compound E103
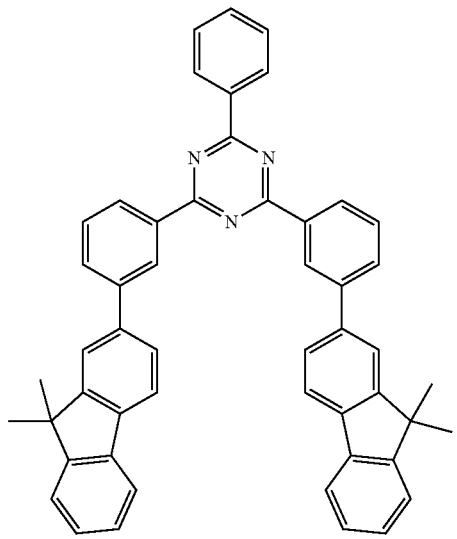
Compound E104
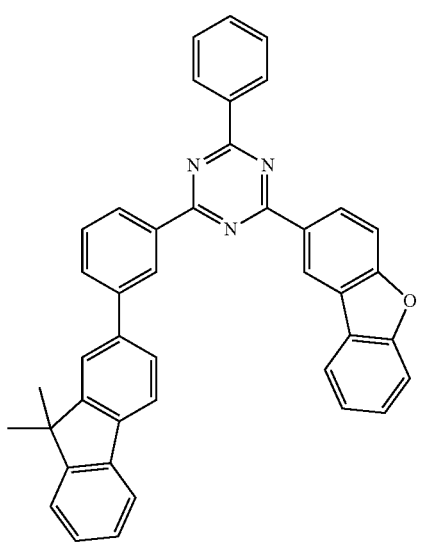
Compound E105
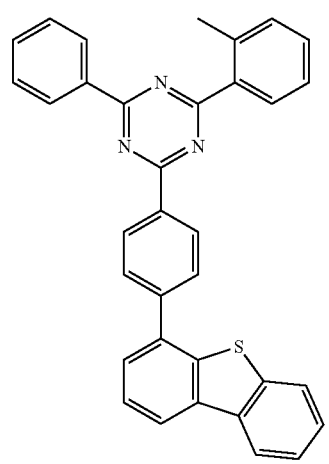
Compound E106
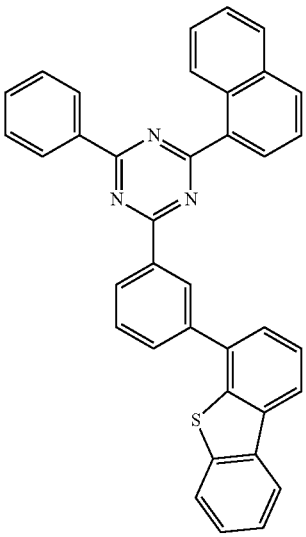
Compound E107
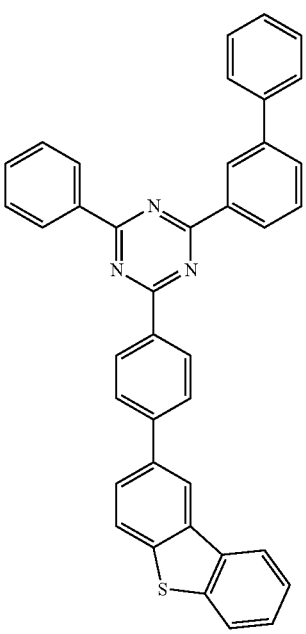

Compound E108
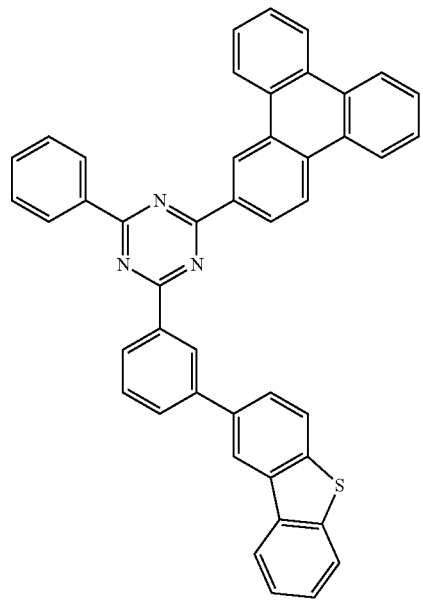
Compound E110
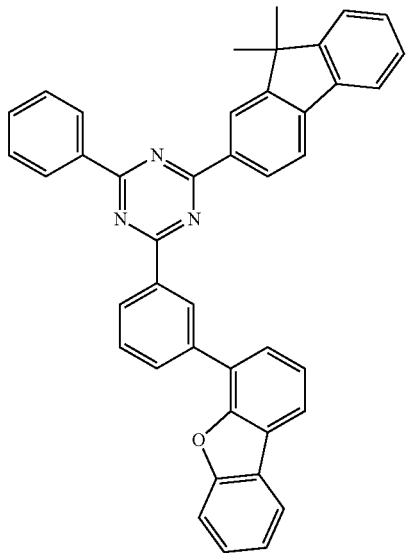
Compound E109
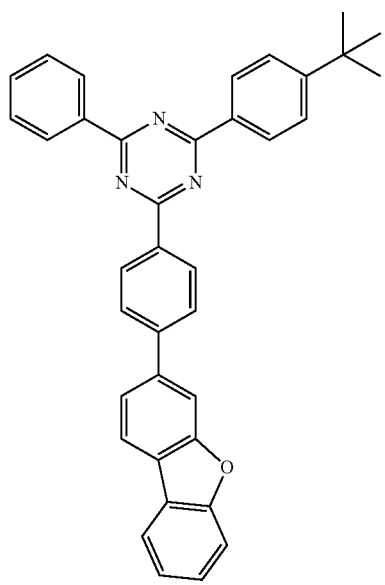
Compound E111
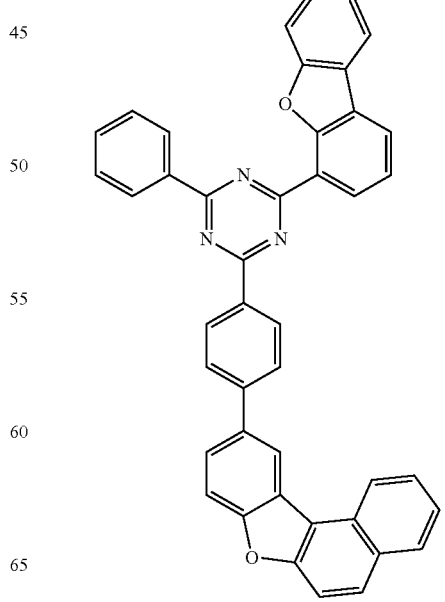

Compound E112
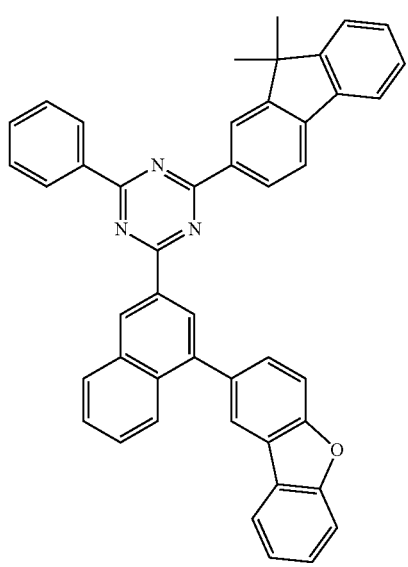
Compound E113
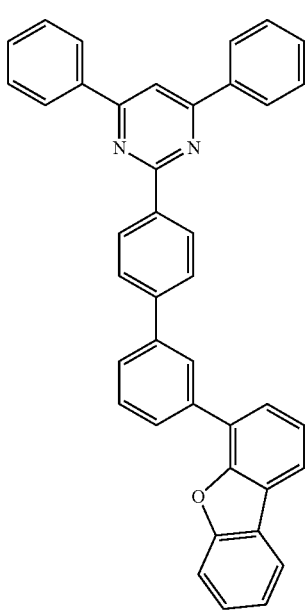
Compound E114
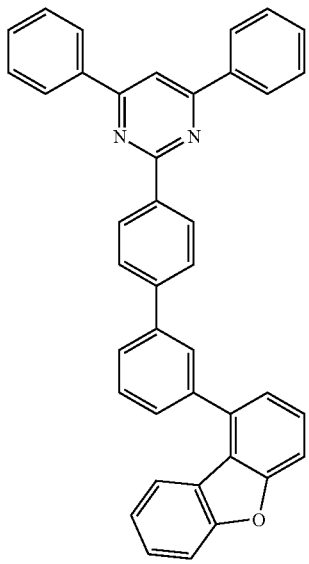
Compound E115
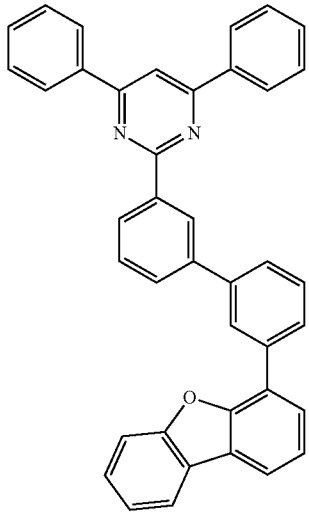

Compound E116
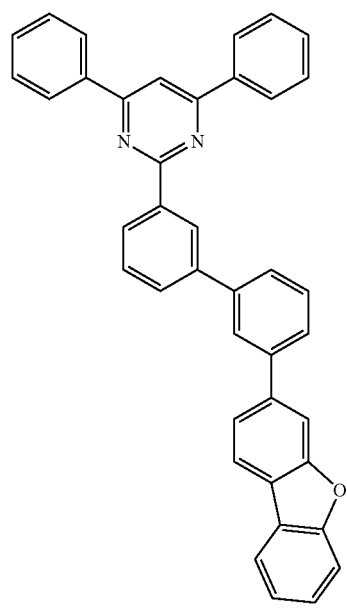
Compound E118
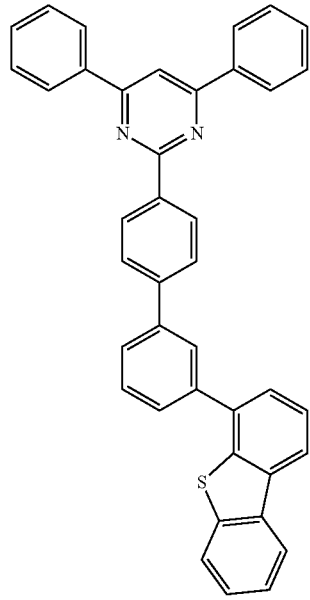
Compound E117
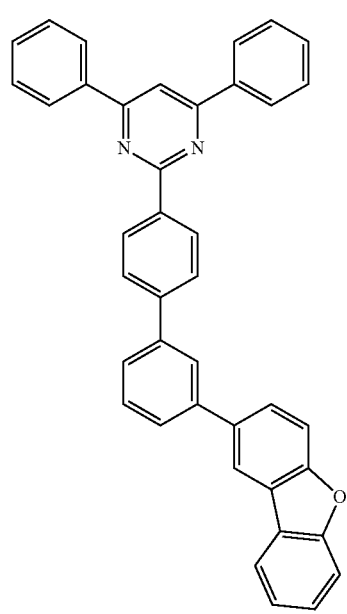
Compound E119
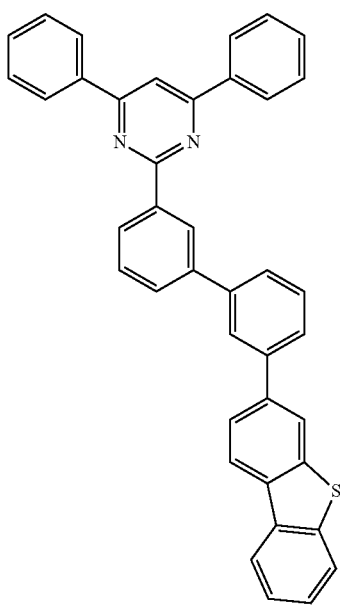

-continued
Compound E120
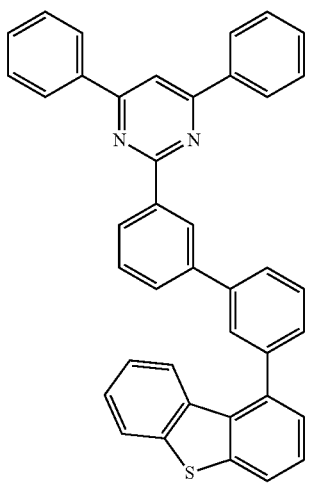
Compound E121
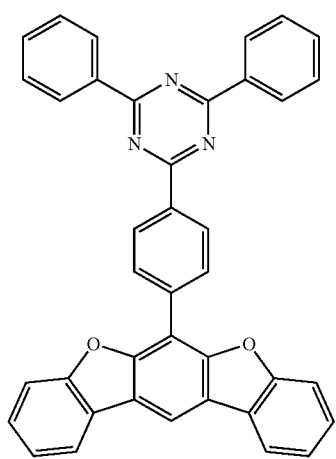
Compound E122
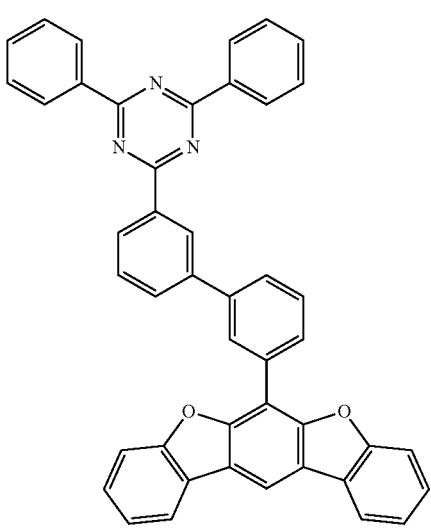
Compound E123
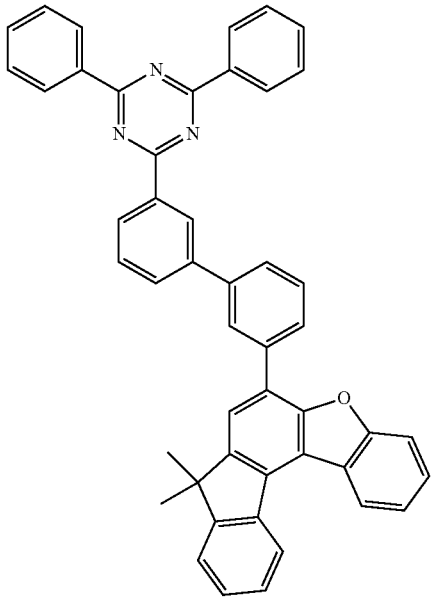
Compound E124
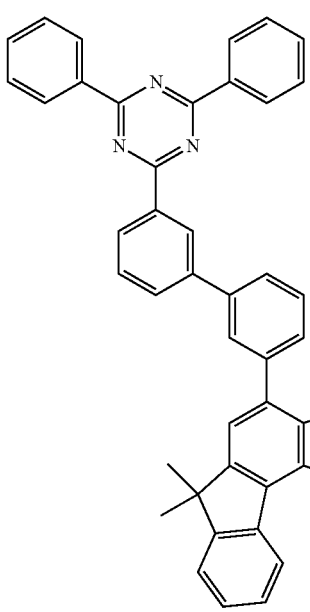

Compound E125
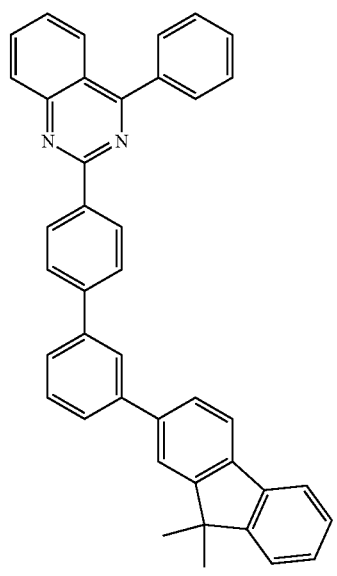
Compound E126
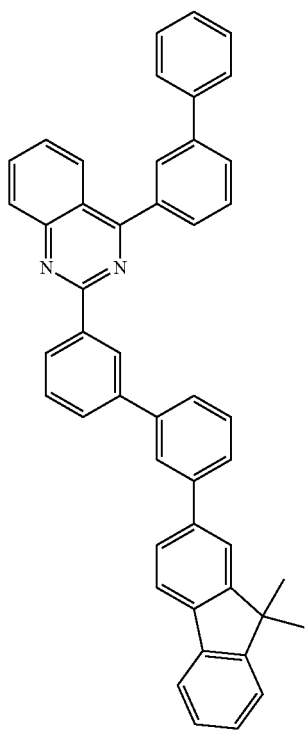
Compound E127
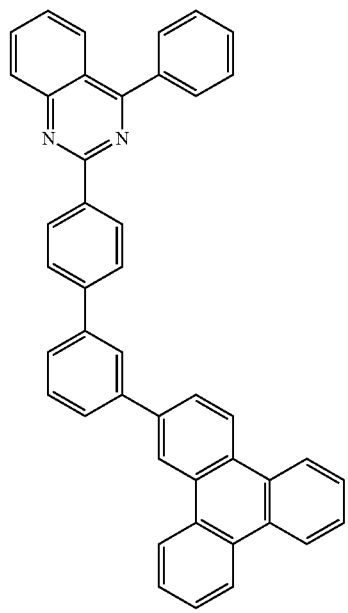
Compound E128
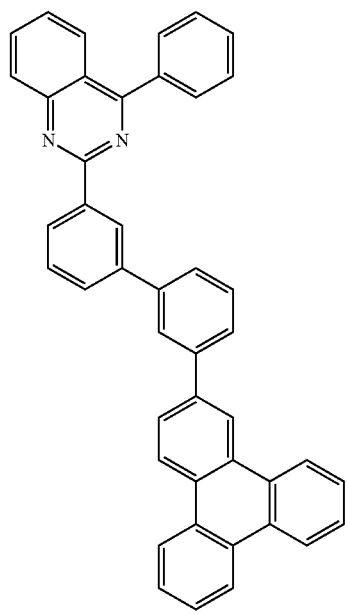

Compound E129

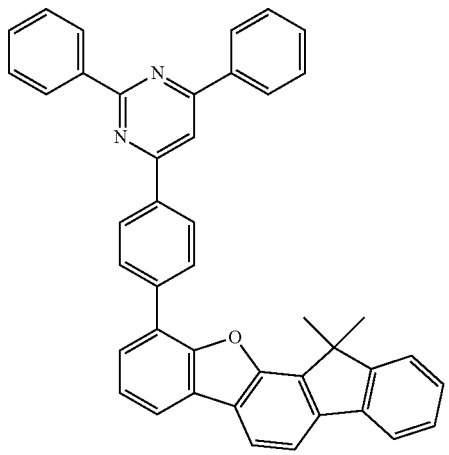

Compound E131

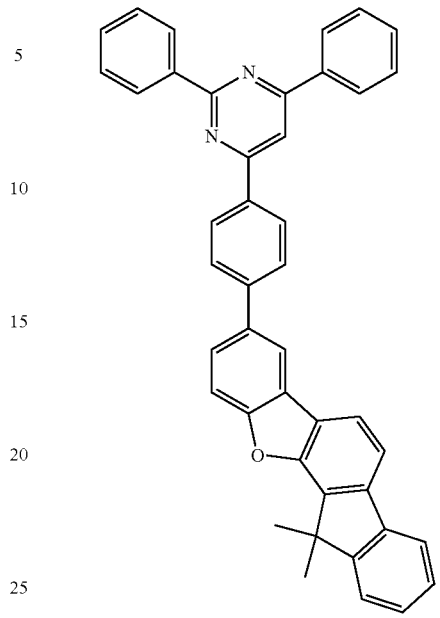

Compound E132

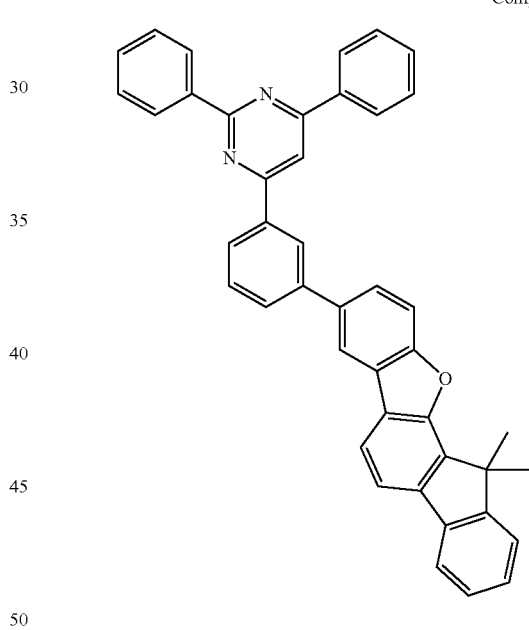

Compound E130

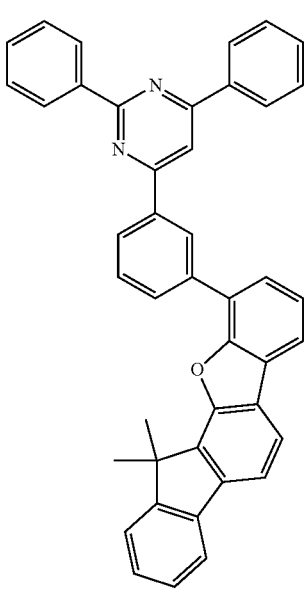

12. The organic light emitting device according to claim 11, wherein the organic layer comprises a light emitting layer, a hole transport layer between the light emitting layer and the first electrode, and an electron transport layer between the light emitting layer and the second electrode and wherein the light emitting layer comprises the first compound represented by Formula A and the second compound represented by Formula B.

13. The organic light emitting device according to claim 11, wherein the light emitting layer comprise a dopant compound.

14. The organic light emitting device according to claim 11, wherein the first compound, the second compound, and the dopant compound are mixed in a weight ratio of 1:0.01-99:0.01-15.

15. The organic light emitting device according to claim 11, further comprising one or more blue, red or green light emitting layers to achieve white light emission.

\* \* \* \* \*